US006168787B1

(12) United States Patent
Morton

(10) Patent No.: US 6,168,787 B1
(45) Date of Patent: Jan. 2, 2001

(54) PLURIPOTENT VACCINE AGAINST ENVELOPED VIRUSES

(75) Inventor: Donald L. Morton, Palisades, CA (US)

(73) Assignee: John Wayne Cancer Institute, Santa Monica, CA (US)

( * ) Notice: Under 35 U.S.C. 154(b), the term of this patent shall be extended for 0 days.

(21) Appl. No.: 08/427,034

(22) Filed: Apr. 24, 1995

(51) Int. Cl.[7] .................................................... A61K 39/00

(52) U.S. Cl. .................... 424/93.21; 424/85.1; 424/85.2; 424/85.4; 424/204.1; 424/207.1; 424/209.1; 424/211.1; 424/218.1; 424/221.1; 424/224.1; 424/229.1

(58) Field of Search .............................. 424/186.1, 199.1, 424/204.1, 209.1, 207.1, 277.1, 85.1, 85.4, 93.21, 211.1, 218.1, 221.1, 224.1, 229.1, 232.1; 530/403; 435/384, 392, 373

(56) References Cited

FOREIGN PATENT DOCUMENTS

WO93/14126 7/1993 (WO) .
WO 94/11016 5/1994 (WO) .

OTHER PUBLICATIONS

Arthur, Larry O., et al., "Cellular Proteins Bound to Immunodeficiency Viruses: Implications for Pathogenesis and Vaccines", *Science*, 258:1935–1938, Dec. 18, 1992.

Chan, Woon L., et al., "Protection in Simian Immunodeficiency Virus–vaccinated Monkeys Correlates with Anti–HLA Class I Antibody Response", *Journal Exp. Medicine*, 176:1203–1207, Oct., 1992.

Clerici, Mario, et al., "Circumvention of Defective CD4 T Helper Cell Function in HIV–Infected Individuals By Stimulation With HLA Alloantigens", *The Journal of Immunology*, 144(9):3266–3271, May 1, 1990.

Cranage, Martin, et al., "Species–Specific Responses to MHC Molecules in SIV Vaccination and Infection", Abstract No. 27, Symposium Nonhum. Primate Models Aids (US), Sep. 19–22, 1993.

Haynes, Barton F., "Scientific and Social Issues of Human Immunodeficiency Virus Vaccine Development", *Science*, 260:1279–1286, May 28, 1993.

Hoon, Dave S. B., et al., "Suppressor Cell Activity in a Randomized Trail of Patients Receiving Active Specific Immunotherapy with Melanoma Cell Vaccine and Low Dosages of Cyclophosphamide", *Cancer Research*, 50:5358–5364, Sep. 1, 1990.

Jones M.D., Peter C., et al., "Prolonged Survival for Melanoma Patients With Elevated IgM Antibody to Oncofetal Antigen", *JNCI*, 66(2):249–254, Feb. 1981.

Kion, Tracy A., et al., "Anti–HIV and Anti—Anti–MHC Antibodies in Alloimmune and Autoimmune Mice", *Science*, 253:1138–1140, Sep. 6, 1991.

Kiprov, Dobri D., et al., "Alloimmunization to Prevent Aids?", *Science*, 263:737–738, Feb. 11, 1994.

Langlois, Alphonse J., et al., "The Ability of Certain SIV Vaccines to Provoke Reactions Against Normal Cells", *Sciences*, 255:292–293, Jan. 17, 1992.

Langlois, Alphonse J., et al., "Detection of Anti–Human Cell Antibodies in Sera from Macaques Immunized With Whole Inactivated Virus", *Aids Research and Human Retroviruses*, 8(9):1641–1652, 1992.

Morton M.D., Donald L., et al., "Demonstration of Antibodies Against Human Malignant Melanoma By Immunofluroescence", *Surgery*, 64(1):233–240, Jul. 1968.

Morton M.D., Donald L., et al., "Prolongation of Survival in Metastic Melanoma After Active Specific Immunotherapy With a New POlyvalent Melanoma Vaccine", *Annals of Surgery*, 216(4):463–482, Oct. 1992.

Stott, E.J., "Anti–Cell Antibody in Macaques", Nature, 353:393, Oct. 3, 1991.

Towsend, Alain, et al., "Antigen Recognition By Class I–Restricted T Lymphocytes", *Annual Reviews Immunol*, 7:601–624, 1989.

Tsuji, Kimiyoshi, et al., "Proceedings of the Eleventh International Histocompatibility Workshop and Conference Held in Yokohama, Japan, Nov. 6–13, 1991", *Oxford University Press*, 1:10 pages, 1992.

PCT Search Report mailed Mar. 9, 1996.

June et al. "The B7 and CD28 receptor families", Immunology Today. vol. 15, No. 7, pp. 321–333, 1994.

Wolf et al. "Expression and function of th emurine B7 antigen, the major costimulatory molecule expressed by peritoneal exudate cells". PNAS., vol. 89, pp. 4210–4214, May 1992.

Takahashi et al., International Immunology, vol. 5, No. 8, pp. 849–857, 1993.

Plaskin et al., Int. J. Cancer, vol. 59, pp. 796–801, 1994.

Plaskin et al. "Effective anti–metastatic melanoma vaccination with tumor cells transfected with MHC genes and/or infected with NewCastle Disease Virus (NDV)". Int. J. Cancer., vol. 59, pp. 796–801, 1994.

Takahashi et al. "Induction of CD8+ cytotixuc T lymphocytes by immunization with syngeneic irradiated HIV–1 derived peptide–pulsed dendritic cells". International Immunology, vol. 5, No. 8, pp. 849–857, 1993.

Illustrated Dictionary of Immunology. edited by Julius Cruse et al. CRC Press, New York, 1995.

Fundamental Immunology. edited by William Paul. Raven Press, New York, 1989.

*Primary Examiner*—Donna C. Wortman
*Assistant Examiner*—Brenda G. Brumback
(74) *Attorney, Agent, or Firm*—Fulbright & Jaworski

(57) ABSTRACT

The present invention is directed to compositions and methods for the induction of immune responses in mammals against enveloped animal viruses. More particularly, the invention provides vaccine compositions containing multiple MHC allotypes. By generating an immune response against these MHC molecules, virus or virus-infected cells expressing foreign MHC molecules can be attacked prior to infection of cells in the immunized host. In some embodiments, the vaccine compositions contain viral antigens and adjuvants as well. The vaccine compositions may comprise intact cells, cell-derived membrane preparations or recombinantly or chemically produced MHC molecules or fragments thereof.

30 Claims, 50 Drawing Sheets

Figures 3, 3I, 4:
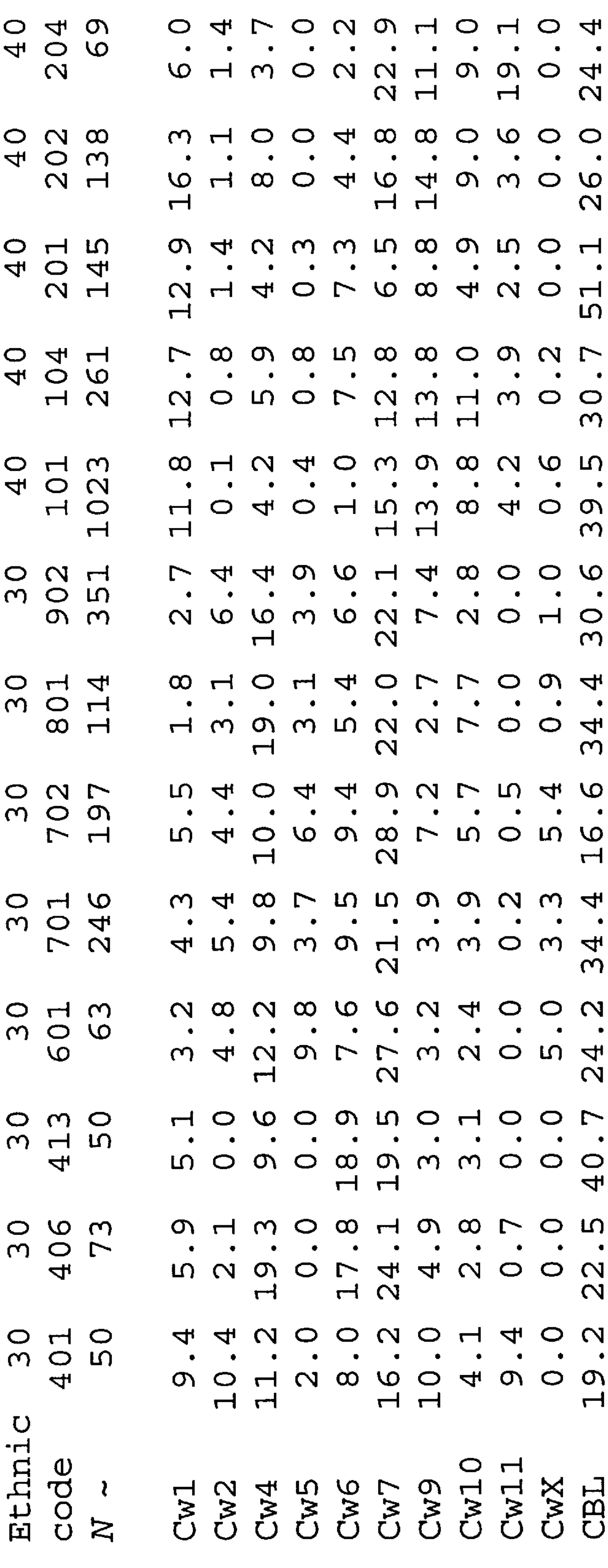
Figures 3, 3J:
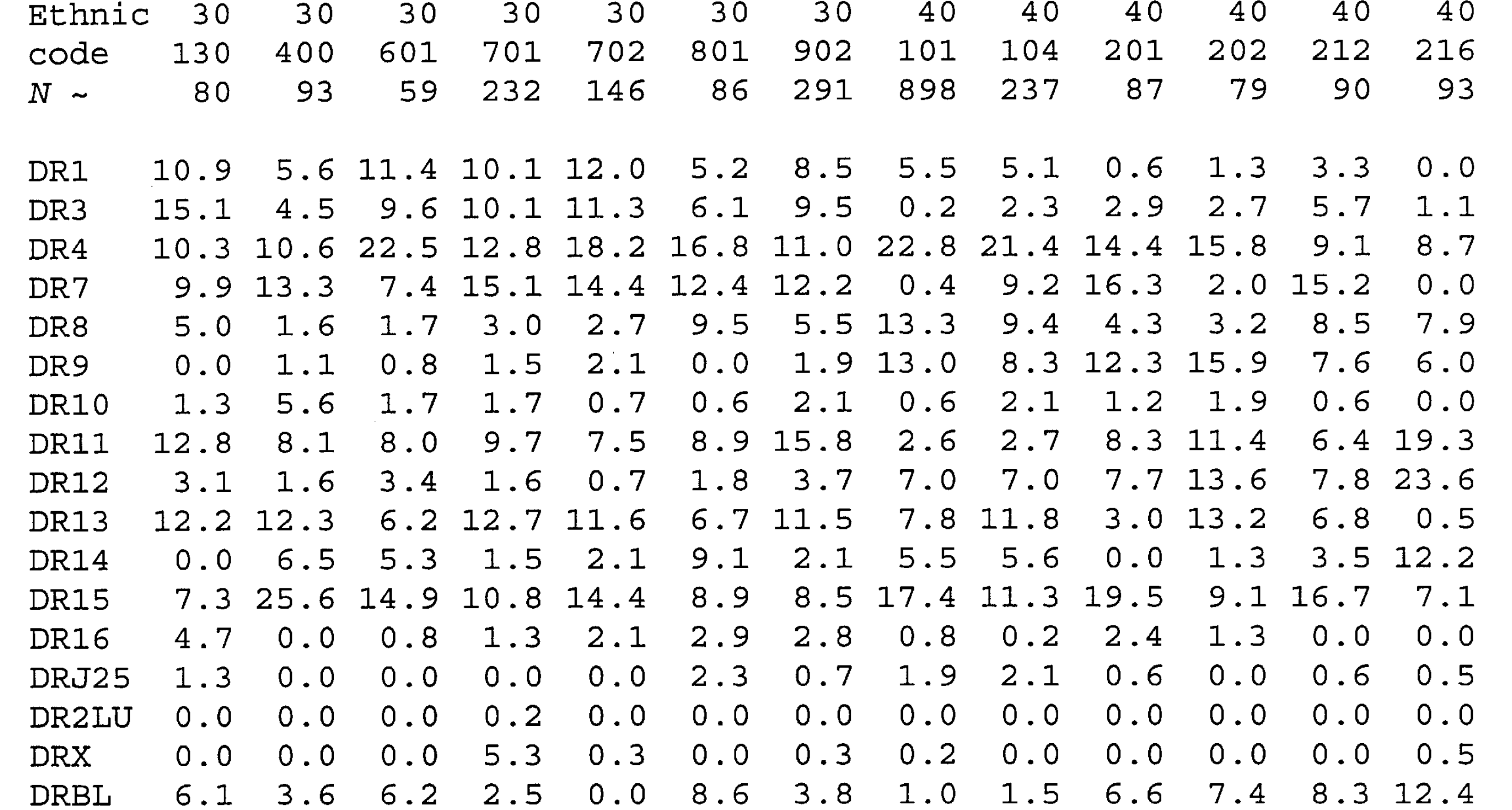

| Items | |
|---|---|
| HLA alleles (serological types) | HLA-A, -B, -C, -DR, and -DQ |
| 2-locus haplotypes | A-B |
| 2-locus haplotypes | C-B |
| 2-locus haplotypes | B-DR |
| 2 locus haplotypes | DR-DQ |
| 3-locus haplotypes | A-C-B |
| 3-locus haplotypes | A-B-DR |
| 3-locus haplotypes | B-DR-DQ |
| 5-locus haplotypes | A-C-B-DR-DQ |
| HLA alleles (DNA types) | DRB1, DRB3, DRB4, DRB5, DQA1, DQB1 DPA1, and DPB1 |
| 2-locus haploytpes | DRB1-DRB3 |
| 2-locus haplotypes | DRB1-DQB1 |
| 2-locus haplotypes | DRB1-DPB1 |
| 2-locus haplotypes | DQA1-DQB1 |
| 2-locus haplotypes | DQB1-DPB1 |
| 2-locus haplotypes | DPA1-DPB1 |
| 3-locus haplotypes | DRB1-DQB1-DPB1 |
| 3-locus haplotypes | DRB1-DRB3-DQB1 |
| 3-locus haplotypes | DRB1-DQA1-DQB1 |
| 3-locus haplotypes | DRB1-DPA1-DPB1 |
| 5-locus haplotypes | DRB1-DQA1-DQB1-DPA1-DPB1 |
| Complement alleles | Bf, C4A, and C4B |
| 3-locus haplotypes | Bf-C4A-C4B |
| 5-locus haplotypes | HLA-A-HLA-B-Bf-C4A-C4B |
| 5-locus haplotypes | HLA-B-Bf-C4A-C4B-HLA-DR |

FIG. 1

| Ethnic code | Ethnic group |
|---|---|
| 10 100 | North African (Blacks) |
| 10 102 | Senegalese |
| 10 200 | South African (Blacks) |
| 10 201 | San (Bushman) |
| 10 202 | Khol (Hottentot) |
| 10 204 | Zimbabwean |
| 10 206 | Zairean |
| 10 207 | West African (Blacks) |
| 10 210 | South African (Blacks in Cape Town) |
| 10 400 | North American (Blacks) |
| 10 600 | Brazilian (Blacks) |
| 20 100 | Australian Aborigine |
| 20 201 | Coastals (Papua New Guinea) |
| 20 202 | Highlanders (Papua New Guinea) |
| 30 101 | Albanian |
| 30 102 | Armenian |
| 30 103 | Austrian |
| 30 104 | Basque |
| 30 105 | Belgian |
| 30 106 | British |
| 30 109 | Cornish |
| 30 110 | Czech |
| 30 111 | Dane |
| 30 113 | French |
| 30 114 | German |
| 30 115 | Greek |
| 30 117 | Italian |
| 30 119 | Polish |
| 30 120 | Portuguese |
| 30 121 | Romanian |
| 30 122 | Sardinian |
| 30 124 | Spanish |
| 30 125 | Swedish |

FIG. 2A

| Ethnic code | Ethnic group |
|---|---|
| 30 127 | Ukrainian |
| 30 128 | Uralic |
| 30 129 | Yugoslavian |
| 30 130 | Hungarian |
| 30 131 | Slovak |
| 30 141 | Gypsy (Spanish) |
| 30 210 | South African (Whites) |
| 30 400 | Indian |
| 30 401 | Bhargavas |
| 30 406 | Iyers |
| 30 413 | Tribal Indian |
| 30 502 | Usbekistan |
| 30 601 | Australian (Whites) |
| 30 701 | USA (Whites) |
| 30 702 | Canadian |
| 30 801 | Mexican |
| 30 902 | Brazilian (Whites) |
| 40 101 | Japanese (Wajin) |
| 40 104 | Korean |
| 40 201 | Northern Han |
| 40 202 | Southern Han |
| 40 204 | Buyi |
| 40 207 | Miao |
| 40 209 | Yi |
| 40 210 | Uygur |
| 40 211 | Tibetan |
| 40 212 | Manchu |
| 40 213 | Orochon |
| 40 216 | Taiwan Aborigine |
| 40 217 | Dai |
| 40 218 | Hui |
| 40 219 | Li |
| 40 220 | Inner Mongolian |

FIG. 2B

| Ethnic code | Ethnic group |
|---|---|
| 40 301 | Buriat |
| 40 302 | Mongolian |
| 40 303 | Kazakhs |
| 40 401 | Thais |
| 40 402 | Thai-Chinese |
| 40 403 | Vietnamese |
| 40 404 | Filipino |
| 40 414 | Javanese |
| 40 416 | Timorese |
| 40 421 | Singapore Chinese |
| 40 602 | Maori |
| 40 800 | North American (Amerinds) |
| 40 802 | Zuni |
| 40 803 | Tlingit |
| 41 003 | Brazilian (Amerinds) |
| 41 00A | Chilean and Colombian (Amerinds) |
| 41 102 | Inuit (Eskimo) |
| 41 10A | Yakut |

FIG. 2C

| Ethnic | 10 | 10 | 10 | 10 | 10 | 10 | 10 | 10 | 10 | 10 | 10 | 20 |
|---|---|---|---|---|---|---|---|---|---|---|---|---|
| code | 100 | 102 | 200 | 201 | 202 | 204 | 206 | 207 | 210 | 400 | 600 | 100 |
| *N* ~ | 59 | 99 | 103 | 103 | 65 | 90 | 61 | 70 | 105 | 447 | 116 | 99 |
| A1 | 3.6 | 5.1 | 2.4 | 1.0 | 9.1 | 1.7 | 4.4 | 5.3 | 9.9 | 5.3 | 5.6 | 2.0 |
| A2 | 13.6 | 19.5 | 14.9 | 18.4 | 9.5 | 17.1 | 13.8 | 20.6 | 16.5 | 16.7 | 12.8 | 15.7 |
| A3 | 5.9 | 6.1 | 6.2 | 15.5 | 3.2 | 3.3 | 7.0 | 1.5 | 5.7 | 8.9 | 8.0 | 6.6 |
| A11 | 4.2 | 0.0 | 0.0 | 0.0 | 0.8 | 0.0 | 0.0 | 0.0 | 5.3 | 2.3 | 3.4 | 4.5 |
| A23 | 10.6 | 18.3 | 9.7 | 12.6 | 14.7 | 9.2 | 19.3 | 9.7 | 2.9 | 8.1 | 14.4 | 6.1 |
| A24 | 5.4 | 1.0 | 4.1 | 0.5 | 3.1 | 0.6 | 1.6 | 3.8 | 6.2 | 4.7 | 3.5 | 31.8 |
| A25 | 1.7 | 0.0 | 0.0 | 0.0 | 0.8 | 0.6 | 0.0 | 0.0 | 0.0 | 0.6 | 1.3 | 0.5 |
| A26 | 3.4 | 4.4 | 5.0 | 0.5 | 4.0 | 4.4 | 1.6 | 2.1 | 7.0 | 1.6 | 2.6 | 1.0 |
| A28 | 11.9 | 6.8 | 11.1 | 10.7 | 6.4 | 7.8 | 10.1 | 12.6 | 9.2 | 10.9 | 9.0 | 3.0 |
| A29 | 3.4 | 5.1 | 5.9 | 0.0 | 6.4 | 5.6 | 3.4 | 2.3 | 4.3 | 3.7 | 3.2 | 2.5 |
| A30 | 9.3 | 14.3 | 13.6 | 20.4 | 13.1 | 31.6 | 13.5 | 11.8 | 11.3 | 9.5 | 10.9 | 1.0 |
| A31 | 0.8 | 1.5 | 3.9 | 0.5 | 3.1 | 0.0 | 1.7 | 0.7 | 1.4 | 1.7 | 5.4 | 1.5 |
| A32 | 1.7 | 2.0 | 2.0 | 6.8 | 0.8 | 1.7 | 2.6 | 1.4 | 1.4 | 1.0 | 0.9 | 3.0 |
| A33 | 8.0 | 10.0 | 1.5 | 0.0 | 0.0 | 2.2 | 5.9 | 15.2 | 6.0 | 8.1 | 6.0 | 1.0 |
| A34 | 4.5 | 2.5 | 6.9 | 0.0 | 0.0 | 5.0 | 3.3 | 2.1 | 4.8 | 5.1 | 3.1 | 19.2 |
| A36 | 4.5 | 0.0 | 1.0 | 0.0 | 0.0 | 4.1 | 0.8 | 0.0 | 0.0 | 2.6 | 0.9 | 0.5 |
| A43 | 0.0 | 0.0 | 2.4 | 11.7 | 17.4 | 1.2 | 0.0 | 0.0 | 2.4 | 0.1 | 0.0 | 0.0 |
| AX | 1.8 | 0.0 | 0.0 | 1.5 | 0.8 | 1.1 | 1.6 | 6.4 | 3.8 | 2.5 | 0.9 | 0.0 |
| ABL | 5.7 | 3.4 | 9.4 | 0.0 | 7.0 | 2.9 | 9.2 | 4.5 | 1.9 | 6.7 | 8.1 | 0.0 |

*FIG. 3A-1*

| Ethnic | 20 | 30 | 30 | 30 | 30 | 30 | 30 | 30 | 30 | 30 | 30 | 30 |
|---|---|---|---|---|---|---|---|---|---|---|---|---|
| code | 202 | 101 | 102 | 103 | 104 | 105 | 106 | 109 | 110 | 111 | 113 | 114 |
| *N* ~ | 51 | 208 | 141 | 98 | 60 | 64 | 117 | 101 | 96 | 150 | 321 | 295 |
| A1 | 0.0 | 14.3 | 10.3 | 16.8 | 12.7 | 13.0 | 15.0 | 17.3 | 17.4 | 13.0 | 13.7 | 18.0 |
| A2 | 0.0 | 26.4 | 15.6 | 28.1 | 24.6 | 20.0 | 24.1 | 39.6 | 29.1 | 30.3 | 21.3 | 27.8 |
| A3 | 0.0 | 10.3 | 17.8 | 15.3 | 7.0 | 20.2 | 15.3 | 12.4 | 12.3 | 13.6 | 13.3 | 14.1 |
| A11 | 12.1 | 6.0 | 5.5 | 5.1 | 7.5 | 5.0 | 7.3 | 5.0 | 5.5 | 5.6 | 6.2 | 4.6 |
| A23 | 0.0 | 2.9 | 4.0 | 2.6 | 5.0 | 2.3 | 2.6 | 1.0 | 3.1 | 2.0 | 2.6 | 2.7 |
| A24 | 65.7 | 10.1 | 15.3 | 9.7 | 10.0 | 6.3 | 6.2 | 5.4 | 11.3 | 8.3 | 8.9 | 7.5 |
| A25 | 0.0 | 1.2 | 0.4 | 1.5 | 0.0 | 2.3 | 1.4 | 0.5 | 3.6 | 2.3 | 2.3 | 2.4 |
| A26 | 0.0 | 3.4 | 5.2 | 2.0 | 2.0 | 4.2 | 5.6 | 2.0 | 5.5 | 4.0 | 4.4 | 4.7 |
| A28 | 0.0 | 3.0 | 4.7 | 4.1 | 0.8 | 4.7 | 4.5 | 4.0 | 2.1 | 5.7 | 5.6 | 5.1 |
| A29 | 0.0 | 1.0 | 1.8 | 4.6 | 11.3 | 3.9 | 4.3 | 5.9 | 1.6 | 3.3 | 6.4 | 2.2 |
| A30 | 0.0 | 1.9 | 0.7 | 3.1 | 11.3 | 1.6 | 2.6 | 3.0 | 1.6 | 1.3 | 2.3 | 2.4 |
| A31 | 0.0 | 3.5 | 3.3 | 2.0 | 1.8 | 3.9 | 2.6 | 1.0 | 2.1 | 2.0 | 3.7 | 2.2 |
| A32 | 0.0 | 8.7 | 4.6 | 2.0 | 0.8 | 4.7 | 4.7 | 2.0 | 1.0 | 5.0 | 4.2 | 3.2 |
| A33 | 0.0 | 2.2 | 2.8 | 1.5 | 0.8 | 1.6 | 1.7 | 0.5 | 1.6 | 2.6 | 3.1 | 3.1 |
| A34 | 19.1 | 0.7 | 0.0 | 0.5 | 0.0 | 0.9 | 0.0 | 0.5 | 0.0 | 0.3 | 0.8 | 0.2 |
| A36 | 0.0 | 0.2 | 1.5 | 0.5 | 0.0 | 0.0 | 0.0 | 0.0 | 0.5 | 0.0 | 0.0 | 0.0 |
| A43 | 0.0 | 0.0 | 0.0 | 0.0 | 0.0 | 0.0 | 0.0 | 0.0 | 0.0 | 0.0 | 0.0 | 0.0 |
| AX | 0.0 | 0.0 | 0.4 | 0.5 | 0.0 | 1.6 | 0.0 | 0.0 | 0.0 | 0.3 | 0.3 | 0.0 |
| ABL | 3.0 | 4.2 | 6.2 | 0.0 | 4.3 | 4.0 | 2.3 | 0.0 | 1.6 | 0.2 | 0.9 | 0.0 |

FIG. 3A-2

| Ethnic code N ~ | 30 115 231 | 30 117 551 | 30 119 50 | 30 120 125 | 30 121 91 | 30 122 97 | 30 124 264 | 30 125 95 | 30 127 83 | 30 128 97 | 30 129 98 | 30 130 98 |
|---|---|---|---|---|---|---|---|---|---|---|---|---|
| A1 | 9.2 | 14.0 | 10.0 | 10.3 | 12.0 | 5.7 | 11.3 | 19.1 | 10.9 | 7.2 | 17.8 | 15.8 |
| A2 | 26.1 | 24.4 | 34.0 | 26.6 | 28.3 | 32.2 | 27.6 | 38.7 | 30.2 | 25.4 | 26.4 | 23.5 |
| A3 | 8.6 | 12.9 | 16.5 | 12.7 | 15.1 | 3.4 | 9.0 | 12.0 | 16.5 | 15.3 | 11.7 | 12.6 |
| A11 | 8.8 | 6.1 | 3.4 | 5.8 | 8.2 | 9.7 | 7.0 | 3.9 | 8.4 | 9.7 | 4.1 | 9.0 |
| A23 | 3.0 | 1.5 | 1.0 | 2.0 | 2.7 | 2.6 | 2.5 | 1.1 | 0.6 | 3.1 | 2.0 | 3.6 |
| A24 | 13.3 | 9.7 | 7.6 | 10.3 | 9.8 | 7.2 | 6.8 | 6.6 | 10.0 | 14.2 | 10.7 | 9.0 |
| A25 | 1.2 | 2.4 | 4.0 | 2.0 | 2.7 | 0.0 | 2.5 | 1.1 | 6.6 | 2.1 | 2.0 | 2.0 |
| A26 | 6.9 | 4.3 | 6.0 | 4.6 | 3.8 | 1.0 | 4.5 | 2.6 | 2.4 | 3.3 | 8.7 | 7.1 |
| A28 | 4.1 | 3.6 | 4.0 | 4.8 | 4.9 | 2.1 | 3.1 | 1.6 | 1.8 | 2.6 | 4.1 | 3.1 |
| A29 | 3.0 | 3.9 | 1.0 | 4.8 | 1.6 | 0.5 | 9.3 | 1.1 | 0.0 | 1.1 | 1.5 | 3.3 |
| A30 | 1.9 | 3.9 | 3.0 | 3.6 | 2.2 | 22.3 | 5.1 | 0.5 | 2.6 | 0.5 | 1.0 | 3.6 |
| A31 | 1.5 | 3.9 | 1.0 | 3.8 | 1.9 | 0.5 | 2.4 | 4.2 | 1.8 | 4.8 | 1.5 | 2.6 |
| A32 | 9.0 | 5.6 | 3.0 | 0.8 | 4.8 | 8.1 | 2.6 | 1.1 | 1.8 | 1.5 | 6.1 | 2.0 |
| A33 | 1.7 | 2.1 | 2.0 | 5.6 | 0.5 | 3.4 | 2.8 | 0.0 | 1.2 | 1.0 | 1.5 | 1.0 |
| A34 | 0.4 | 0.1 | 1.0 | 0.0 | 0.0 | 0.0 | 0.8 | 1.1 | 0.6 | 0.5 | 0.5 | 0.0 |
| A36 | 0.2 | 0.1 | 0.0 | 0.0 | 0.0 | 0.0 | 0.2 | 0.0 | 0.6 | 1.0 | 0.0 | 0.0 |
| A43 | 0.2 | 0.0 | 0.0 | 0.0 | 0.0 | 0.0 | 0.0 | 0.0 | 0.0 | 0.0 | 0.0 | 0.0 |
| AX | 0.0 | 0.2 | 0.0 | 0.0 | 0.0 | 0.0 | 0.8 | 1.6 | 0.0 | 0.0 | 0.0 | 0.0 |
| ABL | 0.6 | 1.3 | 2.4 | 2.2 | 1.3 | 1.4 | 1.5 | 4.0 | 4.0 | 6.7 | 0.2 | 1.7 |

FIG. 3A-3

| Ethnic | 30 | 30 | 30 | 30 | 30 | 30 | 30 | 30 | 30 | 30 | 30 | 40 |
|---|---|---|---|---|---|---|---|---|---|---|---|---|
| code | 131 | 141 | 400 | 401 | 406 | 413 | 601 | 701 | 702 | 801 | 902 | 101 |
| *N* ~ | 61 | 75 | 99 | 50 | 73 | 50 | 63 | 246 | 197 | 114 | 351 | 1023 |
| A1 | 13.9 | 28.1 | 11.1 | 20.9 | 16.5 | 12.0 | 20.3 | 16.9 | 18.6 | 5.3 | 9.9 | 0.7 |
| A2 | 29.0 | 11.8 | 12.1 | 12.0 | 7.2 | 18.5 | 26.3 | 28.3 | 26.7 | 23.2 | 26.0 | 24.4 |
| A3 | 15.2 | 5.7 | 7.9 | 19.9 | 6.8 | 6.0 | 7.8 | 12.2 | 11.3 | 7.0 | 6.9 | 0.6 |
| A11 | 1.6 | 25.6 | 15.9 | 8.8 | 8.6 | 5.0 | 1.6 | 5.5 | 4.1 | 4.8 | 4.7 | 10.4 |
| A23 | 1.6 | 2.0 | 1.0 | 7.8 | 0.0 | 6.0 | 0.8 | 1.6 | 1.0 | 3.9 | 2.9 | 0.0 |
| A24 | 9.7 | 6.1 | 18.1 | 13.6 | 18.4 | 17.2 | 7.8 | 9.6 | 11.3 | 16.7 | 9.6 | 35.1 |
| A25 | 4.3 | 2.0 | 0.5 | 1.0 | 0.0 | 0.0 | 4.0 | 3.3 | 2.3 | 2.2 | 2.5 | 0.0 |
| A26 | 3.4 | 5.0 | 6.6 | 1.0 | 3.4 | 3.0 | 4.8 | 3.9 | 5.3 | 3.5 | 5.3 | 10.9 |
| A28 | 3.3 | 1.3 | 6.1 | 0.0 | 2.7 | 8.6 | 5.6 | 4.5 | 3.6 | 9.6 | 6.4 | 0.0 |
| A29 | 0.8 | 1.3 | 3.0 | 0.0 | 0.0 | 3.0 | 4.0 | 2.6 | 1.8 | 3.9 | 4.6 | 0.0 |
| A30 | 2.6 | 2.0 | 1.1 | 3.0 | 2.9 | 1.0 | 3.2 | 2.6 | 3.3 | 5.7 | 6.0 | 0.4 |
| A31 | 3.3 | 0.0 | 2.5 | 1.0 | 5.5 | 2.0 | 0.0 | 2.0 | 2.2 | 4.4 | 4.8 | 8.0 |
| A32 | 4.3 | 6.0 | 2.0 | 0.0 | 3.4 | 7.1 | 5.6 | 5.1 | 5.8 | 3.9 | 2.9 | 0.0 |
| A33 | 0.0 | 0.7 | 9.2 | 5.0 | 17.5 | 7.5 | 0.0 | 1.0 | 1.8 | 3.5 | 2.6 | 7.7 |
| A34 | 0.0 | 0.0 | 0.0 | 0.0 | 1.4 | 0.0 | 1.8 | 0.6 | 0.3 | 1.3 | 0.9 | 0.0 |
| A36 | 0.0 | 0.0 | 0.0 | 0.0 | 0.7 | 0.0 | 0.0 | 0.2 | 0.0 | 0.0 | 0.4 | 0.0 |
| A43 | 0.0 | 0.0 | 0.0 | 0.0 | 0.7 | 0.0 | 0.0 | 0.0 | 0.0 | 0.0 | 0.0 | 0.0 |
| AX | 0.0 | 0.0 | 0.0 | 0.0 | 0.7 | 0.0 | 0.8 | 0.2 | 0.0 | 0.9 | 0.4 | 0.0 |
| ABL | 6.9 | 2.5 | 2.9 | 6.0 | 3.4 | 3.1 | 6.0 | 0.0 | 0.8 | 0.0 | 3.3 | 1.7 |

*FIG. 3A-4*

| Ethnic | 40 | 40 | 40 | 40 |
|---|---|---|---|---|
| code | 104 | 201 | 202 | 204 |
| *N* ~ | 261 | 145 | 138 | 69 |
| A1 | 2.5 | 4.7 | 0.4 | 1.4 |
| A2 | 29.3 | 36.7 | 33.7 | 42.8 |
| A3 | 1.3 | 2.4 | 1.1 | 0.7 |
| A11 | 9.4 | 20.3 | 31.9 | 29.7 |
| A23 | 0.0 | 0.7 | 0.0 | 0.0 |
| A24 | 22.8 | 12.6 | 19.9 | 16.7 |
| A25 | 0.0 | 1.1 | 0.0 | 0.7 |
| A26 | 8.1 | 2.8 | 0.7 | 3.6 |
| A28 | 0.6 | 0.3 | 0.0 | 0.0 |
| A29 | 0.4 | 1.0 | 0.0 | 0.0 |
| A30 | 4.4 | 4.4 | 2.2 | 0.0 |
| A31 | 3.9 | 3.1 | 2.9 | 0.7 |
| A32 | 1.0 | 0.7 | 0.7 | 0.7 |
| A33 | 14.9 | 3.4 | 6.5 | 2.9 |
| A34 | 0.0 | 1.1 | 0.0 | 0.0 |
| A36 | 0.0 | 0.0 | 0.0 | 0.0 |
| A43 | 0.0 | 0.0 | 0.0 | 0.0 |
| AX | 0.0 | 0.4 | 0.0 | 0.0 |
| ABL | 1.4 | 4.2 | 0.0 | 0.0 |

*FIG. 3A-5*

| Ethnic | 10 | 10 | 10 | 10 | 10 | 10 | 10 | 30 | 30 | 30 | 30 | 30 |
|---|---|---|---|---|---|---|---|---|---|---|---|---|
| code | 100 | 200 | 201 | 204 | 210 | 400 | 600 | 101 | 102 | 103 | 104 | 105 |
| *N* ~ | 56 | 89 | 54 | 79 | 96 | 318 | 112 | 153 | 105 | 94 | 57 | 55 |
| DR1 | 6.3 | 2.8 | 0.0 | 9.2 | 4.7 | 6.3 | 8.9 | 5.8 | 8.6 | 10.1 | 10.5 | 10.9 |
| DR3 | 14.0 | 29.2 | 1.9 | 15.3 | 10.4 | 14.7 | 12.4 | 8.5 | 11.7 | 12.2 | 21.9 | 8.2 |
| DR4 | 5.4 | 2.8 | 43.5 | 1.9 | 10.4 | 3.4 | 6.2 | 10.5 | 17.8 | 10.1 | 7.9 | 12.7 |
| DR7 | 10.0 | 6.8 | 7.3 | 7.6 | 14.5 | 9.5 | 8.9 | 10.1 | 7.3 | 13.3 | 28.9 | 12.7 |
| DR8 | 8.9 | 1.1 | 5.6 | 3.8 | 1.9 | 8.3 | 4.0 | 2.0 | 1.0 | 3.2 | 3.5 | 1.8 |
| DR9 | 1.8 | 1.2 | 1.9 | 0.6 | 1.0 | 2.9 | 4.3 | 2.9 | 0.0 | 2.1 | 0.0 | 1.8 |
| DR10 | 0.9 | 1.7 | 0.0 | 3.8 | 2.6 | 1.1 | 4.0 | 0.0 | 1.4 | 0.5 | 0.9 | 0.9 |
| DR11 | 11.6 | 24.7 | 6.3 | 22.7 | 18.2 | 13.5 | 13.2 | 19.1 | 26.4 | 13.8 | 8.8 | 10.0 |
| DR12 | 4.5 | 5.1 | 1.9 | 4.8 | 8.3 | 3.8 | 2.7 | 3.3 | 2.1 | 1.1 | 0.9 | 2.7 |
| DR13 | 14.9 | 14.2 | 24.5 | 12.1 | 7.8 | 13.8 | 12.7 | 10.3 | 7.1 | 11.7 | 5.3 | 15.5 |
| DR14 | 2.9 | 2.8 | 0.0 | 0.0 | 2.1 | 2.4 | 0.9 | 5.6 | 3.3 | 6.4 | 0.9 | 3.6 |
| DR15 | 12.8 | 5.1 | 1.9 | 11.8 | 9.9 | 11.7 | 16.2 | 9.5 | 11.2 | 14.9 | 9.6 | 17.3 |
| DR16 | 1.8 | 0.0 | 0.0 | 0.0 | 2.1 | 2.0 | 3.4 | 6.7 | 0.5 | 0.5 | 0.9 | 1.8 |
| DRJ25 | 0.0 | 0.0 | 0.0 | 0.0 | 0.0 | 0.5 | 0.4 | 0.0 | 0.0 | 0.0 | 0.0 | 0.0 |
| DR2LU | 0.0 | 0.0 | 0.0 | 0.0 | 3.1 | 0.3 | 0.4 | 0.0 | 0.0 | 0.0 | 0.0 | 0.0 |
| DRX | 0.9 | 0.0 | 0.9 | 1.3 | 2.6 | 2.2 | 0.0 | 1.0 | 0.0 | 0.0 | 0.0 | 0.0 |
| DRBL | 3.4 | 2.5 | 4.5 | 5.1 | 0.4 | 3.7 | 1.2 | 4.8 | 1.6 | 0.0 | 0.0 | 0.0 |

FIG. 3B-1

| Ethnic | 30 | 30 | 30 | 30 | 30 | 30 | 30 | 30 | 30 | 30 | 30 | 30 |
|---|---|---|---|---|---|---|---|---|---|---|---|---|
| code | 106 | 109 | 110 | 111 | 113 | 114 | 115 | 117 | 120 | 121 | 122 | 124 |
| *N* ~ | 101 | 101 | 79 | 124 | 285 | 256 | 181 | 507 | 85 | 82 | 76 | 219 |
| DR1 | 10.7 | 5.0 | 12.7 | 8.9 | 10.8 | 9.5 | 12.7 | 8.5 | 10.5 | 8.5 | 9.1 | 10.9 |
| DR3 | 12.4 | 11.4 | 7.0 | 8.9 | 11.0 | 10.1 | 8.2 | 10.2 | 10.3 | 11.0 | 26.2 | 11.6 |
| DR4 | 13.9 | 24.8 | 8.2 | 17.2 | 10.8 | 13.4 | 5.2 | 7.1 | 8.2 | 8.7 | 11.8 | 16.0 |
| DR7 | 20.8 | 19.3 | 14.6 | 11.9 | 13.5 | 11.3 | 6.8 | 13.7 | 18.0 | 9.1 | 5.3 | 18.6 |
| DR8 | 3.7 | 2.0 | 5.7 | 3.6 | 5.2 | 4.2 | 4.4 | 3.2 | 5.9 | 1.2 | 1.3 | 3.0 |
| DR9 | 2.0 | 2.5 | 0.6 | 2.0 | 1.4 | 1.0 | 0.0 | 0.1 | 0.0 | 0.6 | 0.7 | 1.8 |
| DR10 | 1.5 | 0.0 | 0.6 | 2.0 | 2.5 | 1.2 | 2.9 | 1.5 | 1.2 | 1.8 | 0.7 | 0.9 |
| DR11 | 6.4 | 7.9 | 17.7 | 6.9 | 9.8 | 18.1 | 27.0 | 26.1 | 9.9 | 13.9 | 14.3 | 11.1 |
| DR12 | 4.0 | 2.0 | 3.2 | 4.0 | 0.4 | 3.9 | 1.9 | 1.1 | 2.4 | 3.7 | 0.7 | 0.9 |
| DR13 | 9.8 | 12.9 | 10.1 | 14.0 | 13.2 | 10.9 | 5.1 | 9.8 | 19.0 | 11.4 | 2.0 | 9.3 |
| DR14 | 3.2 | 1.0 | 2.5 | 3.0 | 3.8 | 3.3 | 3.0 | 2.3 | 0.0 | 2.7 | 3.3 | 2.1 |
| DR15 | 10.2 | 11.4 | 10.1 | 11.6 | 11.2 | 8.8 | 6.3 | 7.4 | 5.7 | 10.0 | 7.7 | 8.4 |
| DR16 | 0.0 | 0.0 | 6.3 | 1.2 | 2.1 | 2.3 | 10.4 | 3.6 | 2.9 | 14.9 | 16.3 | 1.0 |
| DRJ25 | 0.0 | 0.0 | 0.0 | 0.8 | 0.0 | 0.6 | 0.0 | 0.1 | 0.0 | 0.0 | 0.0 | 0.0 |
| DR2LU | 0.0 | 0.0 | 0.0 | 0.8 | 0.0 | 0.2 | 0.0 | 0.0 | 0.0 | 0.0 | 0.0 | 0.0 |
| DRX | 0.0 | 0.0 | 0.6 | 0.8 | 1.2 | 0.6 | 0.0 | 0.5 | 0.0 | 0.0 | 0.0 | 2.1 |
| DRBL | 1.6 | 0.0 | 0.0 | 2.4 | 3.1 | 0.7 | 6.0 | 4.9 | 6.1 | 2.4 | 0.8 | 2.3 |

*FIG. 3B-2*

| Ethnic | 30 | 30 | 30 | 30 | 30 | 30 | 30 | 30 | 30 | 40 | 40 | 40 |
|---|---|---|---|---|---|---|---|---|---|---|---|---|
| code | 128 | 129 | 130 | 400 | 601 | 701 | 702 | 801 | 902 | 101 | 104 | 201 |
| *N* ~ | 48 | 100 | 80 | 93 | 59 | 232 | 146 | 86 | 291 | 898 | 237 | 87 |
| DR1 | 8.3 | 9.3 | 10.9 | 5.6 | 11.4 | 10.1 | 12.0 | 5.2 | 8.5 | 5.5 | 5.1 | 0.6 |
| DR3 | 10.4 | 11.5 | 15.1 | 4.5 | 9.6 | 10.1 | 11.3 | 6.1 | 9.5 | 0.2 | 2.3 | 2.9 |
| DR4 | 16.4 | 10.3 | 10.3 | 10.6 | 22.5 | 12.8 | 18.2 | 16.8 | 11.0 | 22.8 | 21.4 | 14.4 |
| DR7 | 13.8 | 8.8 | 9.9 | 13.3 | 7.4 | 15.1 | 14.4 | 12.4 | 12.2 | 0.4 | 9.2 | 16.3 |
| DR8 | 7.3 | 4.5 | 5.0 | 1.6 | 1.7 | 3.0 | 2.7 | 9.5 | 5.5 | 13.3 | 9.4 | 4.3 |
| DR9 | 7.9 | 0.5 | 0.0 | 1.1 | 0.8 | 1.5 | 2.1 | 0.0 | 1.9 | 13.0 | 8.3 | 12.3 |
| DR10 | 0.0 | 1.5 | 1.3 | 5.6 | 1.7 | 1.7 | 0.7 | 0.6 | 2.1 | 0.6 | 2.1 | 1.2 |
| DR11 | 13.5 | 15.9 | 12.8 | 8.1 | 8.0 | 9.7 | 7.5 | 8.9 | 15.8 | 2.6 | 2.7 | 8.3 |
| DR12 | 4.2 | 2.0 | 3.1 | 1.6 | 3.4 | 1.6 | 0.7 | 1.8 | 3.7 | 7.0 | 7.0 | 7.7 |
| DR13 | 3.1 | 12.4 | 12.2 | 12.3 | 6.2 | 12.7 | 11.6 | 6.7 | 11.5 | 7.8 | 11.8 | 3.0 |
| DR14 | 3.6 | 2.0 | 0.0 | 6.5 | 5.3 | 1.5 | 2.1 | 9.1 | 2.1 | 5.5 | 5.6 | 0.0 |
| DR15 | 9.0 | 8.3 | 7.3 | 25.6 | 14.9 | 10.8 | 14.4 | 8.9 | 8.5 | 17.4 | 11.3 | 19.5 |
| DR16 | 0.0 | 8.3 | 4.7 | 0.0 | 0.8 | 1.3 | 2.1 | 2.9 | 2.8 | 0.8 | 0.2 | 2.4 |
| DRJ25 | 0.0 | 0.0 | 1.3 | 0.0 | 0.0 | 0.0 | 0.0 | 2.3 | 0.7 | 1.9 | 2.1 | 0.6 |
| DR2LU | 0.0 | 1.0 | 0.0 | 0.0 | 0.0 | 0.2 | 0.0 | 0.0 | 0.0 | 0.0 | 0.0 | 0.0 |
| DRX | 0.0 | 1.0 | 0.0 | 0.0 | 0.0 | 5.3 | 0.3 | 0.0 | 0.3 | 0.2 | 0.0 | 0.0 |
| DRBL | 2.4 | 2.6 | 6.1 | 3.6 | 6.2 | 2.5 | 0.0 | 8.6 | 3.8 | 1.0 | 1.5 | 6.6 |

FIG. 3B-3

| Ethnic | 40 | 40 | 40 | 40 | 40 | 40 | 40 | 40 | 40 | 40 | 40 | 40 |
|---|---|---|---|---|---|---|---|---|---|---|---|---|
| code | 202 | 212 | 216 | 219 | 220 | 302 | 401 | 402 | 403 | 414 | 416 | 421 |
| *N* ~ | 79 | 90 | 93 | 72 | 54 | 101 | 238 | 70 | 142 | 61 | 49 | 77 |
| DR1 | 1.3 | 3.3 | 0.0 | 16.1 | 7.7 | 4.0 | 0.2 | 0.0 | 1.4 | 0.0 | 1.0 | 0.6 |
| DR3 | 2.7 | 5.7 | 1.1 | 21.5 | 8.9 | 9.1 | 4.8 | 7.1 | 4.0 | 0.8 | 5.2 | 5.2 |
| DR4 | 15.8 | 9.1 | 8.7 | 9.0 | 12.4 | 13.4 | 9.0 | 16.4 | 8.7 | 4.1 | 5.2 | 19.5 |
| DR7 | 2.0 | 15.2 | 0.0 | 2.1 | 11.8 | 13.4 | 8.3 | 6.4 | 5.8 | 3.5 | 0.0 | 1.9 |
| DR8 | 3.2 | 8.5 | 7.9 | 2.8 | 4.6 | 7.9 | 4.0 | 4.3 | 6.7 | 6.9 | 3.2 | 6.5 |
| DR9 | 15.9 | 7.6 | 6.0 | 17.0 | 7.4 | 5.9 | 11.9 | 9.3 | 11.5 | 2.5 | 0.0 | 16.9 |
| DR10 | 1.9 | 0.6 | 0.0 | 1.4 | 2.9 | 2.0 | 2.5 | 2.1 | 5.7 | 0.0 | 1.0 | 1.3 |
| DR11 | 11.4 | 6.4 | 19.3 | 8.1 | 12.9 | 8.0 | 4.2 | 6.4 | 2.1 | 3.5 | 12.3 | 13.6 |
| DR12 | 13.6 | 7.8 | 23.6 | 2.1 | 2.8 | 8.4 | 13.7 | 12.1 | 29.7 | 49.7 | 7.5 | 13.6 |
| DR13 | 13.2 | 6.8 | 0.5 | 2.1 | 5.8 | 5.4 | 3.6 | 5.7 | 4.2 | 3.3 | 3.1 | 1.3 |
| DR14 | 1.3 | 3.5 | 12.2 | 3.5 | 0.9 | 2.0 | 7.1 | 6.4 | 5.6 | 0.8 | 3.1 | 3.2 |
| DR15 | 9.1 | 16.7 | 7.1 | 4.3 | 11.5 | 13.0 | 20.6 | 17.1 | 9.5 | 20.6 | 42.0 | 9.7 |
| DR16 | 1.3 | 0.0 | 0.0 | 2.9 | 0.0 | 2.8 | 4.5 | 2.9 | 2.1 | 0.0 | 0.0 | 3.2 |
| DRJ25 | 0.0 | 0.6 | 0.5 | 0.0 | 0.0 | 1.5 | 0.2 | 0.0 | 0.4 | 0.0 | 0.0 | 0.0 |
| DR2LU | 0.0 | 0.0 | 0.0 | 0.0 | 0.0 | 0.0 | 1.7 | 2.1 | 0.0 | 0.0 | 0.0 | 3.2 |
| DRX | 0.0 | 0.0 | 0.5 | 0.0 | 0.0 | 0.0 | 0.2 | 1.4 | 0.4 | 0.0 | 0.0 | 0.0 |
| DRBL | 7.4 | 8.3 | 12.4 | 7.1 | 10.6 | 3.3 | 3.4 | 0.1 | 2.1 | 4.2 | 16.2 | 0.0 |

FIG. 3B-4

| Ethnic | 40 | 40 | 41 | 41 |
|---|---|---|---|---|
| code | 602 | 803 | 00A | 102 |
| *N* ~ | 51 | 57 | 65 | 145 |
| DR1 | 2.9 | 0.9 | 2.3 | 0.7 |
| DR3 | 2.9 | 0.9 | 2.3 | 3.9 |
| DR4 | 20.0 | 10.9 | 41.7 | 38.3 |
| DR7 | 0.0 | 1.8 | 0.8 | 0.7 |
| DR8 | 9.8 | 7.0 | 4.7 | 3.8 |
| DR9 | 11.3 | 3.5 | 13.7 | 5.3 |
| DR10 | 0.0 | 0.9 | 0.0 | 0.0 |
| DR11 | 9.8 | 0.0 | 12.1 | 11.2 |
| DR12 | 21.2 | 1.8 | 0.8 | 0.7 |
| DR13 | 1.0 | 4.4 | 4.6 | 7.5 |
| DR14 | 9.8 | 60.2 | 1.5 | 10.8 |
| DR15 | 9.6 | 4.9 | 2.3 | 1.4 |
| DR16 | 0.0 | 0.0 | 0.8 | 1.4 |
| DRJ25 | 0.0 | 0.9 | 0.8 | 5.2 |
| DR2LU | 0.0 | 0.0 | 0.0 | 0.3 |
| DRX | 0.0 | 0.0 | 0.0 | 0.3 |
| DRBL | 1.6 | 2.1 | 11.5 | 8.4 |

FIG. 3B-5

| Ethnic | 10 | 10 | 10 | 10 | 10 | 10 | 10 | 30 | 30 | 30 | 30 | 30 |
|---|---|---|---|---|---|---|---|---|---|---|---|---|
| code | 100 | 200 | 201 | 204 | 210 | 400 | 600 | 101 | 102 | 103 | 104 | 105 |
| *N* ~ | 56 | 89 | 54 | 79 | 96 | 318 | 112 | 153 | 105 | 94 | 57 | 55 |
| DQ1 | 50.9 | 42.2 | 31.3 | 59.1 | 40.8 | 45.1 | 47.8 | 40.9 | 31.5 | 39.9 | 28.9 | 49.2 |
| DQ2 | 21.4 | 16.9 | 10.2 | 15.5 | 19.3 | 19.8 | 17.1 | 16.8 | 16.7 | 19.7 | 50.0 | 16.1 |
| DQ3 | 2.7 | 1.7 | 28.3 | 3.8 | 6.9 | 5.0 | 4.4 | 5.2 | 8.3 | 7.2 | 9.6 | 11.6 |
| DQ4 | 5.4 | 22.5 | 5.8 | 7.3 | 4.7 | 10.0 | 5.8 | 2.3 | 1.0 | 5.2 | 4.4 | 2.7 |
| DQ7 | 19.6 | 16.3 | 15.0 | 11.6 | 25.5 | 18.6 | 18.3 | 29.6 | 38.2 | 24.6 | 7.0 | 18.8 |
| DQX | 0.0 | 0.0 | 0.0 | 0.0 | 0.5 | 0.0 | 0.0 | 0.0 | 0.0 | 0.0 | 0.0 | 0.0 |
| DQBL | 0.0 | 0.0 | 9.4 | 2.7 | 2.4 | 1.5 | 6.5 | 5.3 | 4.2 | 3.4 | 0.0 | 1.6 |

| Ethnic | 30 | 30 | 30 | 30 | 30 | 30 | 30 | 30 | 30 | 30 | 30 | 30 |
|---|---|---|---|---|---|---|---|---|---|---|---|---|
| code | 106 | 109 | 110 | 111 | 113 | 114 | 115 | 117 | 120 | 121 | 122 | 124 |
| *N* ~ | 101 | 101 | 79 | 124 | 285 | 256 | 181 | 507 | 85 | 82 | 76 | 219 |
| DQ1 | 36.9 | 28.7 | 40.8 | 43.9 | 45.9 | 36.3 | 45.5 | 35.4 | 43.0 | 50.6 | 38.0 | 34.3 |
| DQ2 | 26.2 | 25.7 | 16.3 | 16.8 | 21.4 | 19.1 | 14.3 | 22.0 | 20.2 | 19.5 | 27.3 | 25.4 |
| DQ3 | 11.0 | 20.8 | 9.1 | 11.4 | 10.0 | 11.1 | 10.1 | 7.3 | 7.6 | 9.8 | 12.9 | 13.9 |
| DQ4 | 3.1 | 2.0 | 4.4 | 4.8 | 4.5 | 6.1 | 3.9 | 2.3 | 6.6 | 0.6 | 0.7 | 3.9 |
| DQ7 | 19.4 | 22.8 | 23.9 | 21.0 | 16.2 | 27.3 | 19.9 | 29.1 | 14.4 | 19.5 | 15.4 | 19.0 |
| DQX | 0.0 | 0.0 | 0.0 | 0.0 | 0.0 | 0.0 | 0.0 | 0.0 | 0.0 | 0.0 | 0.0 | 0.2 |
| DQBL | 3.2 | 0.0 | 5.5 | 2.2 | 2.1 | 0.0 | 6.2 | 3.9 | 8.2 | 0.0 | 5.7 | 3.4 |

*FIG. 3C-1*

| Ethnic | 30 | 30 | 30 | 30 | 30 | 30 | 30 | 30 | 30 | 40 | 40 | 40 |
|---|---|---|---|---|---|---|---|---|---|---|---|---|
| code | 128 | 129 | 130 | 400 | 601 | 701 | 702 | 801 | 902 | 101 | 104 | 201 |
| *N* ~ | 48 | 100 | 80 | 93 | 59 | 232 | 146 | 86 | 291 | 898 | 237 | 87 |
| DQ1 | 32.1 | 44.5 | 35.9 | 56.1 | 37.8 | 43.7 | 41.5 | 26.6 | 38.1 | 45.6 | 40.6 | 35.3 |
| DQ2 | 17.5 | 19.0 | 22.6 | 13.2 | 14.4 | 22.9 | 21.8 | 16.7 | 18.2 | 0.6 | 10.2 | 12.6 |
| DQ3 | 2.1 | 11.5 | 8.8 | 13.4 | 15.9 | 12.1 | 11.6 | 11.8 | 7.1 | 18.8 | 17.0 | 9.2 |
| DQ4 | 5.5 | 4.0 | 2.5 | 1.6 | 3.4 | 2.4 | 3.1 | 7.7 | 6.6 | 14.9 | 8.3 | 4.1 |
| DQ7 | 36.7 | 21.0 | 17.4 | 12.0 | 21.8 | 16.3 | 21.4 | 25.1 | 24.3 | 15.2 | 15.8 | 19.6 |
| DQX | 0.0 | 0.0 | 0.0 | 0.0 | 0.0 | 0.0 | 0.0 | 0.0 | 0.0 | 0.1 | 0.0 | 0.0 |
| DQBL | 6.2 | 0.0 | 12.8 | 3.7 | 6.7 | 2.7 | 0.6 | 12.2 | 5.7 | 4.8 | 8.1 | 19.3 |

| Ethnic | 40 | 40 | 40 | 40 | 40 | 40 | 40 | 40 | 40 | 40 | 40 | 40 |
|---|---|---|---|---|---|---|---|---|---|---|---|---|
| code | 202 | 212 | 216 | 219 | 220 | 302 | 401 | 402 | 403 | 414 | 416 | 421 |
| *N* ~ | 79 | 90 | 93 | 72 | 54 | 101 | 238 | 70 | 142 | 61 | 49 | 77 |
| DQ1 | 39.4 | 34.4 | 33.5 | 39.2 | 31.1 | 36.3 | 48.4 | 37.6 | 33.7 | 33.5 | 59.0 | 26.6 |
| DQ2 | 5.4 | 17.2 | 1.1 | 16.6 | 14.0 | 20.8 | 11.5 | 10.0 | 9.8 | 4.9 | 11.1 | 8.4 |
| DQ3 | 8.2 | 11.1 | 1.6 | 21.4 | 12.4 | 2.5 | 18.6 | 22.9 | 16.9 | 9.8 | 6.1 | 27.3 |
| DQ4 | 6.3 | 3.3 | 1.6 | 5.6 | 3.7 | 1.5 | 3.7 | 4.6 | 4.2 | 9.8 | 2.0 | 7.1 |
| DQ7 | 37.8 | 19.4 | 48.2 | 8.6 | 27.2 | 25.7 | 17.0 | 21.2 | 35.1 | 41.8 | 21.4 | 30.5 |
| DQX | 0.0 | 0.0 | 0.5 | 0.0 | 0.0 | 0.0 | 0.0 | 0.0 | 0.0 | 0.0 | 0.0 | 0.0 |
| DQBL | 2.9 | 14.5 | 13.4 | 8.6 | 11.5 | 13.3 | 0.8 | 3.7 | 0.3 | 0.2 | 0.3 | 0.0 |

FIG. 3C-2

| Ethnic | 40 | 40 | 41 | 41 |
| --- | --- | --- | --- | --- |
| code | 602 | 803 | 00A | 102 |
| *N* ~ | 51 | 57 | 65 | 145 |
| DQ1 | 31.8 | 11.0 | 6.6 | 13.4 |
| DQ2 | 4.9 | 1.8 | 3.1 | 1.7 |
| DQ3 | 20.2 | 6.0 | 31.8 | 5.3 |
| DQ4 | 10.8 | 8.8 | 12.0 | 5.7 |
| DQ7 | 30.9 | 67.9 | 31.7 | 70.4 |
| DQX | 0.0 | 0.0 | 0.0 | 0.0 |
| DQBL | 1.4 | 4.6 | 14.9 | 3.5 |

*FIG. 3C-3*

| Ethnic | 40 | 40 | 40 | 40 | 40 | 40 | 40 | 40 | 40 | 40 | 40 | 40 |
|---|---|---|---|---|---|---|---|---|---|---|---|---|
| code | 207 | 210 | 211 | 212 | 213 | 216 | 218 | 219 | 220 | 301 | 302 | 303 |
| *N* ~ | 70 | 60 | 99 | 187 | 73 | 165 | 87 | 79 | 104 | 89 | 138 | 59 |
| A1 | 1.4 | 7.0 | 3.0 | 4.6 | 3.4 | 0.0 | 4.8 | 1.3 | 6.0 | 8.4 | 8.3 | 11.4 |
| A2 | 30.7 | 17.2 | 32.7 | 34.2 | 22.6 | 18.1 | 23.5 | 26.4 | 23.1 | 27.5 | 23.1 | 29.2 |
| A3 | 0.7 | 17.6 | 2.0 | 5.2 | 1.4 | 0.0 | 7.6 | 4.4 | 7.8 | 4.1 | 4.8 | 8.0 |
| A11 | 42.1 | 5.8 | 13.6 | 14.6 | 2.7 | 11.3 | 18.1 | 29.1 | 8.8 | 8.0 | 8.7 | 9.2 |
| A23 | 0.7 | 0.8 | 0.0 | 1.1 | 0.0 | 0.0 | 0.0 | 4.4 | 2.0 | 5.1 | 2.2 | 0.8 |
| A24 | 16.4 | 14.8 | 32.2 | 17.1 | 43.8 | 61.0 | 14.1 | 9.5 | 15.0 | 21.3 | 18.6 | 20.4 |
| A25 | 0.0 | 1.7 | 1.5 | 0.3 | 0.0 | 0.3 | 0.0 | 1.6 | 0.5 | 0.6 | 0.7 | 0.8 |
| A26 | 0.7 | 7.7 | 2.0 | 1.4 | 6.8 | 4.7 | 1.7 | 6.3 | 6.0 | 3.9 | 5.8 | 5.3 |
| A28 | 0.7 | 1.7 | 0.0 | 0.8 | 0.0 | 0.0 | 0.0 | 1.3 | 0.5 | 1.7 | 0.7 | 1.7 |
| A29 | 0.0 | 0.9 | 0.0 | 0.0 | 0.7 | 0.0 | 0.0 | 0.6 | 1.9 | 1.1 | 1.4 | 0.0 |
| A30 | 1.4 | 2.5 | 3.5 | 5.6 | 1.4 | 0.3 | 7.2 | 5.1 | 3.6 | 0.0 | 4.3 | 0.8 |
| A31 | 0.7 | 1.7 | 4.9 | 4.0 | 15.1 | 0.0 | 3.5 | 3.8 | 9.8 | 5.2 | 4.2 | 4.2 |
| A32 | 0.0 | 4.2 | 0.0 | 1.4 | 0.7 | 0.0 | 0.0 | 0.0 | 0.0 | 0.0 | 1.8 | 0.0 |
| A33 | 4.3 | 0.0 | 0.0 | 4.8 | 0.7 | 1.2 | 7.4 | 1.9 | 4.5 | 3.4 | 6.3 | 1.7 |
| A34 | 0.0 | 0.0 | 0.0 | 0.0 | 0.0 | 0.3 | 0.0 | 3.0 | 0.5 | 0.0 | 1.4 | 0.0 |
| A36 | 0.0 | 2.6 | 0.0 | 0.3 | 0.7 | 0.0 | 0.0 | 0.6 | 0.5 | 0.6 | 3.1 | 0.0 |
| A43 | 0.0 | 0.0 | 0.5 | 0.5 | 0.0 | 0.0 | 0.0 | 0.0 | 0.0 | 0.0 | 0.0 | 0.0 |
| AX | 0.0 | 0.0 | 0.0 | 0.0 | 0.0 | 0.0 | 0.0 | 0.0 | 0.0 | 0.0 | 0.0 | 0.0 |
| ABL | 0.0 | 14.0 | 3.9 | 4.1 | 0.0 | 2.7 | 12.1 | 0.7 | 9.7 | 9.1 | 4.3 | 6.4 |

*FIG. 3D-1*

| Ethnic | 40 | 40 | 40 | 40 | 40 | 40 | 40 | 40 | 40 | 41 | 41 | 41 | 41 |
|---|---|---|---|---|---|---|---|---|---|---|---|---|---|
| code | 401 | 402 | 403 | 414 | 416 | 421 | 602 | 800 | 803 | 003 | 00A | 102 | 10A |
| *N* ~ | 242 | 71 | 149 | 68 | 51 | 73 | 53 | 51 | 56 | 61 | 72 | 156 | 79 |
| A1 | 2.3 | 2.8 | 3.7 | 1.6 | 5.3 | 0.7 | 0.9 | 4.9 | 3.6 | 0.8 | 6.9 | 1.6 | 12.7 |
| A2 | 25.5 | 25.0 | 25.9 | 14.8 | 11.0 | 37.0 | 24.5 | 25.5 | 42.0 | 32.0 | 37.1 | 16.7 | 13.3 |
| A3 | 1.5 | 2.1 | 1.7 | 1.5 | 0.0 | 0.7 | 0.9 | 2.9 | 2.7 | 0.9 | 3.9 | 1.6 | 9.5 |
| A11 | 32.5 | 28.6 | 26.3 | 14.5 | 10.8 | 26.0 | 10.4 | 1.0 | 0.9 | 0.8 | 0.0 | 1.0 | 5.7 |
| A23 | 0.0 | 0.0 | 0.3 | 0.0 | 0.0 | 0.0 | 0.0 | 1.0 | 1.8 | 0.0 | 0.0 | 0.3 | 2.5 |
| A24 | 14.6 | 16.7 | 13.5 | 39.1 | 43.7 | 16.4 | 41.5 | 19.6 | 26.8 | 0.8 | 33.7 | 63.8 | 25.3 |
| A25 | 0.4 | 0.0 | 0.0 | 0.0 | 0.0 | 0.0 | 0.9 | 0.0 | 0.9 | 0.0 | 0.7 | 0.0 | 0.0 |
| A26 | 1.9 | 1.4 | 2.1 | 5.4 | 7.2 | 0.7 | 0.9 | 2.0 | 0.0 | 0.0 | 0.7 | 0.3 | 2.5 |
| A28 | 0.8 | 0.0 | 0.7 | 0.0 | 0.0 | 0.7 | 1.9 | 6.9 | 12.5 | 2.6 | 6.8 | 12.5 | 1.9 |
| A29 | 0.6 | 0.0 | 8.8 | 0.0 | 0.0 | 2.1 | 0.9 | 2.0 | 0.0 | 0.0 | 2.8 | 0.3 | 0.6 |
| A30 | 1.1 | 1.4 | 3.0 | 0.0 | 0.0 | 0.0 | 0.0 | 2.0 | 0.0 | 0.8 | 0.0 | 0.0 | 0.6 |
| A31 | 1.7 | 1.4 | 2.3 | 0.7 | 3.0 | 3.4 | 0.9 | 27.5 | 3.6 | 43.6 | 1.4 | 0.0 | 19.6 |
| A32 | 0.2 | 0.0 | 0.0 | 0.0 | 0.0 | 0.0 | 0.0 | 2.0 | 2.7 | 0.0 | 0.7 | 1.0 | 0.6 |
| A33 | 13.6 | 18.7 | 7.9 | 6.9 | 0.0 | 8.2 | 3.8 | 1.0 | 1.8 | 12.3 | 2.1 | 1.0 | 5.1 |
| A34 | 1.3 | 0.7 | 0.0 | 2.3 | 1.0 | 4.1 | 12.3 | 0.0 | 0.9 | 0.0 | 0.7 | 0.0 | 0.0 |
| A36 | 0.2 | 0.0 | 0.0 | 0.0 | 1.0 | 0.0 | 0.0 | 0.0 | 0.0 | 0.0 | 0.0 | 0.0 | 0.0 |
| A43 | 0.4 | 0.0 | 0.0 | 0.0 | 0.0 | 0.0 | 0.0 | 0.0 | 0.0 | 0.0 | 0.0 | 0.0 | 0.0 |
| AX | 0.0 | 0.0 | 0.3 | 0.0 | 0.0 | 0.0 | 0.0 | 2.0 | 0.0 | 0.0 | 0.0 | 0.0 | 0.0 |
| ABL | 1.5 | 1.1 | 3.5 | 13.3 | 17.0 | 0.0 | 0.0 | 0.0 | 0.0 | 5.3 | 1.2 | 0.0 | 0.0 |

*FIG. 3D-2*

| Ethnic | 10 | 10 | 10 | 10 | 10 | 10 | 10 | 10 | 10 | 10 | 10 | 20 | 20 |
|---|---|---|---|---|---|---|---|---|---|---|---|---|---|
| code | 100 | 102 | 200 | 201 | 202 | 204 | 206 | 207 | 210 | 400 | 600 | 100 | 202 |
| *N* ~ | 59 | 99 | 103 | 103 | 65 | 90 | 61 | 70 | 105 | 447 | 116 | 99 | 51 |
| B7 | 4.2 | 4.5 | 8.1 | 12.8 | 12.3 | 7.8 | 6.2 | 6.7 | 4.3 | 8.3 | 9.6 | 1.5 | 0.0 |
| B8 | 3.4 | 6.3 | 9.8 | 13.3 | 0.0 | 3.5 | 2.8 | 2.9 | 5.7 | 3.2 | 2.2 | 1.0 | 0.0 |
| B13 | 0.0 | 0.0 | 2.4 | 0.5 | 0.8 | 1.7 | 1.0 | 0.0 | 2.4 | 0.9 | 1.8 | 7.5 | 12.7 |
| B14 | 3.6 | 1.7 | 3.9 | 2.4 | 4.6 | 3.9 | 4.9 | 3.0 | 4.3 | 3.0 | 2.6 | 3.0 | 0.0 |
| B18 | 6.7 | 4.7 | 1.9 | 7.1 | 4.6 | 7.0 | 4.1 | 2.3 | 5.7 | 3.3 | 3.4 | 0.0 | 0.0 |
| B27 | 1.7 | 2.0 | 0.0 | 0.0 | 4.6 | 0.0 | 0.8 | 2.1 | 2.9 | 1.6 | 0.4 | 6.6 | 5.6 |
| B35 | 4.8 | 13.1 | 0.5 | 0.0 | 0.8 | 2.2 | 3.3 | 13.6 | 4.8 | 7.7 | 10.0 | 3.5 | 0.0 |
| B37 | 0.8 | 1.0 | 0.0 | 0.0 | 0.8 | 0.0 | 1.6 | 0.7 | 2.4 | 0.9 | 0.9 | 0.5 | 0.0 |
| B38 | 0.8 | 0.0 | 0.0 | 0.0 | 0.0 | 0.0 | 0.0 | 0.0 | 1.9 | 0.2 | 0.9 | 2.0 | 0.0 |
| B39 | 4.5 | 3.0 | 1.0 | 0.0 | 3.8 | 0.6 | 2.5 | 0.0 | 1.4 | 0.8 | 1.3 | 1.5 | 2.0 |
| B41 | 0.0 | 0.0 | 1.5 | 4.1 | 10.3 | 2.2 | 4.9 | 0.0 | 1.9 | 1.8 | 0.0 | 0.5 | 0.0 |
| B42 | 5.9 | 3.0 | 12.8 | 1.5 | 2.3 | 7.5 | 3.3 | 4.3 | 3.8 | 4.7 | 6.6 | 0.0 | 0.0 |
| B44 | 5.1 | 5.6 | 7.1 | 2.4 | 6.9 | 5.8 | 5.7 | 2.9 | 8.6 | 6.2 | 7.0 | 6.6 | 1.0 |
| B45 | 3.4 | 1.0 | 2.4 | 0.5 | 3.1 | 10.0 | 2.8 | 4.5 | 2.4 | 3.8 | 2.6 | 0.0 | 0.0 |
| B46 | 0.0 | 0.0 | 0.0 | 0.0 | 0.0 | 0.0 | 0.0 | 0.0 | 0.5 | 0.0 | 0.0 | 0.0 | 0.0 |
| B47 | 0.0 | 1.5 | 0.0 | 0.0 | 1.5 | 0.0 | 0.8 | 0.0 | 1.9 | 0.1 | 0.0 | 0.0 | 0.0 |
| B48 | 0.8 | 0.0 | 1.0 | 0.0 | 0.0 | 0.0 | 0.0 | 0.0 | 0.5 | 0.2 | 0.9 | 0.0 | 0.0 |
| B49 | 5.1 | 5.6 | 0.5 | 0.5 | 0.0 | 1.1 | 5.7 | 3.7 | 1.4 | 2.7 | 3.1 | 0.0 | 0.0 |
| B50 | 1.7 | 0.5 | 0.0 | 0.0 | 0.0 | 0.0 | 0.0 | 0.7 | 0.5 | 1.0 | 1.7 | 0.0 | 1.0 |
| B51 | 2.5 | 2.1 | 0.0 | 0.5 | 1.5 | 0.6 | 2.5 | 7.1 | 6.2 | 3.2 | 1.7 | 2.5 | 0.0 |
| B52 | 2.5 | 5.1 | 0.0 | 0.0 | 0.8 | 0.0 | 0.0 | 3.9 | 1.4 | 1.1 | 3.6 | 0.0 | 0.0 |

FIG. 3E-1-1

| Ethnic | 30 | 30 | 30 | 30 | 30 | 30 | 30 | 30 | 30 | 30 | 30 | 30 | 30 |
|---|---|---|---|---|---|---|---|---|---|---|---|---|---|
| code | 101 | 102 | 103 | 104 | 105 | 106 | 109 | 110 | 111 | 113 | 114 | 115 | 117 |
| *N* ~ | 208 | 141 | 98 | 60 | 64 | 117 | 101 | 96 | 150 | 321 | 295 | 231 | 551 |
| B7 | 7.7 | 9.0 | 15.8 | 9.2 | 10.2 | 8.5 | 13.9 | 9.7 | 9.2 | 7.5 | 10.7 | 5.9 | 5.8 |
| B8 | 4.7 | 2.9 | 9.2 | 5.8 | 5.5 | 13.7 | 11.4 | 8.9 | 8.9 | 6.8 | 9.8 | 3.6 | 6.8 |
| B13 | 3.1 | 1.1 | 5.0 | 2.5 | 2.3 | 1.3 | 1.5 | 8.3 | 2.0 | 3.0 | 3.2 | 2.6 | 3.9 |
| B14 | 4.4 | 3.7 | 2.0 | 3.3 | 4.7 | 5.6 | 4.5 | 3.1 | 1.4 | 7.2 | 3.7 | 2.8 | 3.6 |
| B18 | 10.8 | 3.7 | 6.1 | 16.7 | 7.0 | 3.4 | 5.4 | 4.9 | 4.0 | 4.8 | 3.4 | 6.3 | 9.6 |
| B27 | 0.7 | 1.8 | 3.1 | 6.7 | 1.6 | 3.8 | 4.0 | 3.5 | 3.0 | 3.6 | 4.6 | 2.4 | 2.2 |
| B35 | 10.3 | 11.6 | 11.7 | 5.0 | 6.3 | 8.5 | 5.4 | 8.1 | 6.0 | 8.4 | 7.6 | 18.3 | 15.4 |
| B37 | 1.9 | 0.7 | 0.5 | 0.0 | 1.6 | 2.1 | 0.0 | 2.1 | 2.4 | 2.3 | 2.0 | 1.7 | 1.4 |
| B38 | 6.0 | 4.6 | 0.5 | 0.0 | 3.1 | 1.3 | 0.0 | 4.2 | 3.2 | 3.0 | 1.9 | 2.4 | 3.5 |
| B39 | 2.9 | 1.1 | 2.0 | 0.8 | 2.3 | 2.1 | 0.0 | 2.1 | 3.3 | 2.5 | 1.9 | 2.2 | 3.3 |
| B41 | 1.2 | 2.1 | 1.5 | 0.0 | 0.8 | 1.3 | 2.0 | 1.0 | 2.0 | 1.6 | 1.7 | 3.1 | 1.6 |
| B42 | 0.0 | 0.0 | 0.0 | 0.0 | 0.0 | 0.0 | 0.0 | 0.0 | 0.0 | 0.0 | 0.2 | 0.2 | 0.0 |
| B44 | 10.9 | 5.4 | 9.6 | 21.7 | 10.2 | 10.3 | 20.8 | 12.5 | 12.9 | 10.8 | 9.2 | 9.4 | 9.2 |
| B45 | 0.0 | 1.8 | 0.5 | 0.0 | 0.0 | 1.3 | 1.0 | 0.0 | 0.7 | 0.6 | 0.8 | 0.2 | 1.0 |
| B46 | 0.0 | 0.0 | 0.0 | 0.0 | 0.0 | 0.0 | 0.0 | 0.0 | 0.0 | 0.0 | 0.2 | 0.0 | 0.1 |
| B47 | 1.0 | 0.0 | 1.5 | 0.8 | 0.0 | 2.1 | 0.0 | 0.5 | 0.7 | 0.2 | 0.7 | 0.4 | 0.5 |
| B48 | 0.0 | 0.0 | 0.0 | 0.0 | 0.0 | 0.0 | 0.0 | 0.0 | 0.7 | 0.0 | 0.2 | 0.0 | 0.1 |
| B49 | 1.9 | 8.0 | 2.0 | 0.8 | 3.9 | 1.3 | 1.0 | 1.6 | 1.0 | 3.0 | 1.5 | 3.5 | 2.9 |
| B50 | 1.4 | 3.9 | 0.0 | 0.8 | 0.0 | 1.3 | 2.0 | 1.6 | 0.7 | 1.5 | 1.0 | 0.4 | 1.8 |
| B51 | 8.9 | 9.6 | 7.6 | 6.7 | 7.0 | 5.1 | 2.5 | 5.7 | 5.7 | 6.9 | 4.9 | 14.4 | 8.4 |
| B52 | 4.2 | 8.0 | 1.0 | 1.7 | 3.9 | 0.9 | 0.5 | 1.0 | 0.7 | 2.5 | 1.0 | 2.5 | 2.6 |

*FIG. 3E-1-2*

| Ethnic | 10 | 10 | 10 | 10 | 10 | 10 | 10 | 10 | 10 | 10 | 10 | 20 | 20 |
|---|---|---|---|---|---|---|---|---|---|---|---|---|---|
| code | 100 | 102 | 200 | 201 | 202 | 204 | 206 | 207 | 210 | 400 | 600 | 100 | 202 |
| *N* ~ | 59 | 99 | 103 | 103 | 65 | 90 | 61 | 70 | 105 | 447 | 116 | 99 | 51 |
| B53 | 7.6 | 4.2 | 1.0 | 1.9 | 0.0 | 7.0 | 9.8 | 11.0 | 1.0 | 12.8 | 4.4 | 0.0 | 0.0 |
| B54 | 0.0 | 0.0 | 0.0 | 0.0 | 0.0 | 0.0 | 0.0 | 0.0 | 0.0 | 0.0 | 0.0 | 0.0 | 0.0 |
| B55 | 0.8 | 0.0 | 0.0 | 0.0 | 0.9 | 0.0 | 0.8 | 0.0 | 0.5 | 0.8 | 3.1 | 1.0 | 0.0 |
| B56 | 0.0 | 4.0 | 0.0 | 0.0 | 0.0 | 0.0 | 0.0 | 0.0 | 0.5 | 0.0 | 0.4 | 17.2 | 22.5 |
| B57 | 4.2 | 1.0 | 2.1 | 2.6 | 5.8 | 9.6 | 3.3 | 2.9 | 4.8 | 4.2 | 3.1 | 3.5 | 0.0 |
| B58 | 6.3 | 8.6 | 17.2 | 35.6 | 11.1 | 11.8 | 4.9 | 7.9 | 11.0 | 6.9 | 1.7 | 1.0 | 0.0 |
| B59 | 0.0 | 0.0 | 0.0 | 0.0 | 0.0 | 0.0 | 0.0 | 0.0 | 0.0 | 0.1 | 0.4 | 0.0 | 0.0 |
| B60 | 0.0 | 0.0 | 0.0 | 0.0 | 0.0 | 0.0 | 0.0 | 0.0 | 2.9 | 1.3 | 0.9 | 10.0 | 15.5 |
| B61 | 0.8 | 0.0 | 0.0 | 0.5 | 0.0 | 0.0 | 0.0 | 0.0 | 0.0 | 0.2 | 1.3 | 19.6 | 2.9 |
| B62 | 1.8 | 0.0 | 0.0 | 0.5 | 0.8 | 0.0 | 0.8 | 0.7 | 2.4 | 1.4 | 1.7 | 7.1 | 28.3 |
| B63 | 3.4 | 0.0 | 1.0 | 0.0 | 0.0 | 0.6 | 4.9 | 0.0 | 0.0 | 2.8 | 0.9 | 0.0 | 0.0 |
| B67 | 0.0 | 0.0 | 0.5 | 0.0 | 0.0 | 0.0 | 0.0 | 0.7 | 0.0 | 0.7 | 0.4 | 0.0 | 0.0 |
| B70 | 8.5 | 9.4 | 22.6 | 10.4 | 18.8 | 13.5 | 16.8 | 8.1 | 8.6 | 8.2 | 2.2 | 0.0 | 0.0 |
| B73 | 0.0 | 0.0 | 0.0 | 0.0 | 0.0 | 0.0 | 0.0 | 0.7 | 0.0 | 0.2 | 0.0 | 0.0 | 0.0 |
| B75 | 1.7 | 0.0 | 0.0 | 0.0 | 0.0 | 0.0 | 0.0 | 0.7 | 2.4 | 0.3 | 0.0 | 3.4 | 6.7 |
| B76 | 0.0 | 0.0 | 0.0 | 0.0 | 0.0 | 0.0 | 0.0 | 0.0 | 0.0 | 0.0 | 0.0 | 0.0 | 0.0 |
| B77 | 0.0 | 0.0 | 0.0 | 0.0 | 0.0 | 0.0 | 2.5 | 0.0 | 1.0 | 0.0 | 0.4 | 0.0 | 1.0 |
| B5102 | 0.8 | 2.6 | 0.0 | 0.0 | 0.0 | 0.0 | 0.8 | 1.4 | 0.0 | 0.2 | 4.1 | 0.0 | 0.0 |
| B7801 | 0.0 | 5.2 | 0.0 | 0.0 | 0.0 | 0.0 | 0.0 | 1.4 | 0.0 | 0.2 | 0.0 | 0.0 | 0.0 |
| BX | 1.7 | 0.0 | 0.0 | 0.5 | 1.5 | 0.6 | 0.0 | 0.0 | 0.5 | 1.1 | 5.8 | 0.0 | 0.0 |
| BBL | 4.4 | 4.0 | 2.8 | 2.4 | 2.5 | 3.0 | 2.5 | 6.0 | 0.0 | 3.6 | 8.7 | 0.4 | 0.9 |

FIG. 3E-2-1

| Ethnic | 30 | 30 | 30 | 30 | 30 | 30 | 30 | 30 | 30 | 30 | 30 | 30 | 30 |
|---|---|---|---|---|---|---|---|---|---|---|---|---|---|
| code | 101 | 102 | 103 | 104 | 105 | 106 | 109 | 110 | 111 | 113 | 114 | 115 | 117 |
| *N* ~ | 208 | 141 | 98 | 60 | 64 | 117 | 101 | 96 | 150 | 321 | 295 | 231 | 551 |
| B53 | 1.0 | 2.6 | 0.5 | 0.0 | 1.6 | 0.9 | 0.0 | 1.0 | 1.0 | 1.2 | 0.8 | 0.9 | 1.0 |
| B54 | 0.2 | 0.0 | 0.0 | 0.0 | 1.6 | 0.0 | 0.0 | 0.0 | 0.0 | 0.0 | 0.0 | 0.2 | 0.0 |
| B55 | 1.9 | 3.3 | 0.5 | 0.8 | 4.7 | 3.4 | 2.0 | 1.6 | 2.0 | 3.7 | 1.5 | 2.9 | 1.8 |
| B56 | 0.5 | 0.0 | 1.0 | 0.0 | 2.3 | 1.3 | 0.5 | 1.0 | 1.7 | 0.8 | 1.5 | 1.1 | 0.4 |
| B57 | 1.9 | 1.1 | 4.1 | 5.8 | 3.1 | 5.6 | 4.5 | 1.6 | 2.4 | 1.9 | 6.3 | 0.0 | 2.0 |
| B58 | 1.4 | 0.7 | 1.0 | 2.5 | 0.8 | 0.9 | 0.5 | 1.0 | 1.3 | 1.9 | 3.4 | 1.8 | 1.8 |
| B59 | 0.0 | 0.4 | 0.0 | 0.0 | 0.0 | 0.0 | 0.0 | 0.0 | 0.0 | 0.0 | 0.0 | 0.0 | 0.0 |
| B60 | 1.7 | 1.4 | 4.5 | 0.8 | 3.9 | 3.8 | 5.0 | 5.1 | 8.6 | 3.0 | 4.6 | 1.7 | 0.5 |
| B61 | 1.7 | 1.1 | 1.0 | 0.0 | 3.1 | 1.7 | 1.0 | 1.6 | 1.7 | 2.7 | 2.5 | 1.8 | 1.4 |
| B62 | 1.9 | 0.7 | 5.1 | 5.0 | 4.7 | 6.0 | 9.9 | 2.1 | 6.8 | 5.3 | 4.9 | 1.7 | 2.8 |
| B63 | 0.7 | 1.1 | 1.5 | 1.7 | 0.8 | 1.3 | 0.5 | 2.9 | 0.0 | 0.9 | 1.7 | 0.6 | 1.7 |
| B67 | 0.0 | 0.0 | 0.0 | 0.0 | 0.0 | 0.0 | 0.0 | 0.0 | 0.0 | 0.0 | 0.0 | 0.0 | 0.2 |
| B70 | 0.7 | 2.1 | 0.5 | 0.8 | 2.3 | 0.9 | 0.5 | 0.0 | 0.7 | 0.6 | 1.4 | 0.9 | 0.3 |
| B73 | 0.0 | 0.4 | 0.0 | 0.0 | 0.0 | 0.0 | 0.0 | 0.0 | 0.3 | 0.3 | 0.2 | 0.0 | 0.1 |
| B75 | 0.7 | 0.7 | 0.0 | 0.0 | 0.0 | 0.4 | 0.0 | 0.0 | 0.0 | 0.0 | 0.3 | 0.0 | 0.1 |
| B76 | 0.0 | 0.0 | 0.0 | 0.0 | 0.0 | 0.0 | 0.0 | 0.0 | 0.0 | 0.0 | 0.0 | 0.0 | 0.1 |
| B77 | 0.2 | 0.0 | 0.0 | 0.0 | 0.0 | 0.0 | 0.0 | 0.0 | 0.0 | 0.2 | 0.2 | 0.0 | 0.0 |
| B5102 | 0.5 | 1.4 | 0.0 | 0.0 | 0.0 | 0.0 | 0.0 | 0.0 | 0.0 | 0.0 | 0.0 | 0.2 | 0.2 |
| B7801 | 0.0 | 0.0 | 0.0 | 0.0 | 0.0 | 0.0 | 0.0 | 0.0 | 0.0 | 0.0 | 0.0 | 0.0 | 0.0 |
| BX | 0.0 | 0.0 | 0.0 | 0.0 | 0.8 | 0.0 | 0.0 | 0.0 | 1.7 | 0.3 | 0.5 | 0.0 | 0.0 |
| BBL | 2.7 | 4.2 | 0.4 | 0.0 | 0.0 | 0.0 | 0.0 | 3.2 | 3.4 | 0.9 | 0.0 | 4.0 | 1.9 |

FIG. 3E-2-2

| Ethnic | 30 | 30 | 30 | 30 | 30 | 30 | 30 | 30 | 30 | 30 | 30 | 30 | 30 |
|---|---|---|---|---|---|---|---|---|---|---|---|---|---|
| code | 119 | 120 | 121 | 122 | 124 | 125 | 127 | 128 | 129 | 130 | 131 | 141 | 400 |
| *N* ~ | 50 | 125 | 91 | 97 | 264 | 95 | 83 | 97 | 98 | 98 | 61 | 75 | 99 |
| B7 | 8.0 | 7.9 | 6.3 | 1.0 | 7.6 | 15.7 | 10.0 | 16.0 | 8.2 | 5.5 | 9.0 | 4.7 | 9.5 |
| B8 | 6.0 | 7.5 | 4.9 | 1.5 | 6.4 | 16.0 | 8.5 | 4.6 | 10.7 | 13.7 | 13.3 | 1.3 | 3.8 |
| B13 | 6.0 | 1.6 | 5.2 | 1.5 | 2.5 | 1.1 | 3.6 | 10.3 | 2.0 | 4.6 | 6.6 | 0.0 | 1.0 |
| B14 | 2.0 | 5.6 | 2.7 | 5.9 | 6.9 | 1.1 | 3.0 | 2.6 | 0.0 | 2.9 | 0.0 | 1.3 | 2.0 |
| B18 | 3.0 | 2.8 | 9.1 | 28.5 | 5.5 | 1.1 | 5.5 | 1.0 | 11.2 | 4.6 | 5.7 | 8.7 | 2.5 |
| B27 | 5.6 | 2.8 | 4.4 | 0.5 | 2.8 | 8.8 | 4.2 | 7.2 | 7.1 | 5.6 | 4.9 | 7.3 | 2.8 |
| B35 | 13.8 | 12.8 | 9.7 | 12.7 | 8.4 | 8.7 | 7.7 | 8.2 | 9.7 | 11.7 | 12.3 | 12.7 | 12.0 |
| B37 | 0.0 | 0.8 | 4.4 | 1.0 | 1.4 | 1.1 | 0.6 | 0.0 | 2.0 | 1.5 | 0.0 | 4.0 | 3.8 |
| B38 | 6.0 | 2.8 | 2.9 | 0.5 | 3.0 | 0.0 | 1.2 | 1.5 | 6.1 | 6.1 | 5.2 | 0.0 | 0.0 |
| B39 | 1.0 | 2.0 | 3.3 | 3.6 | 0.6 | 0.5 | 2.5 | 6.2 | 0.0 | 1.0 | 0.9 | 4.0 | 1.5 |
| B41 | 2.0 | 1.2 | 0.5 | 0.0 | 1.6 | 0.5 | 2.5 | 2.1 | 0.5 | 1.5 | 1.8 | 0.0 | 0.0 |
| B42 | 0.0 | 0.4 | 0.0 | 0.0 | 0.0 | 0.0 | 0.0 | 0.0 | 0.0 | 0.0 | 0.0 | 0.0 | 0.0 |
| B44 | 13.6 | 14.3 | 7.7 | 4.6 | 17.0 | 11.1 | 11.1 | 5.7 | 15.3 | 8.7 | 9.0 | 5.3 | 7.1 |
| B45 | 1.3 | 1.2 | 0.5 | 3.1 | 1.4 | 1.1 | 0.6 | 0.0 | 0.0 | 1.5 | 1.6 | 0.7 | 0.0 |
| B46 | 0.0 | 0.0 | 0.0 | 0.0 | 0.0 | 0.0 | 0.6 | 0.0 | 0.0 | 0.0 | 0.0 | 0.0 | 0.0 |
| B47 | 0.0 | 0.4 | 1.6 | 0.0 | 0.8 | 0.5 | 0.0 | 0.0 | 0.0 | 0.5 | 0.8 | 0.0 | 0.0 |
| B48 | 0.0 | 0.0 | 0.0 | 0.0 | 0.0 | 0.5 | 0.0 | 1.5 | 0.5 | 0.0 | 0.0 | 0.0 | 0.5 |
| B49 | 1.0 | 3.2 | 3.3 | 6.5 | 3.7 | 0.0 | 1.8 | 2.1 | 1.0 | 2.0 | 0.8 | 4.0 | 1.5 |
| B50 | 0.0 | 2.2 | 1.1 | 1.5 | 2.7 | 0.0 | 0.6 | 0.0 | 0.5 | 0.5 | 0.0 | 0.0 | 1.5 |
| B51 | 7.0 | 11.4 | 12.6 | 5.9 | 7.8 | 2.6 | 5.0 | 3.1 | 9.7 | 6.0 | 3.3 | 9.3 | 7.6 |
| B52 | 1.0 | 1.6 | 2.9 | 0.5 | 2.0 | 0.0 | 3.1 | 0.5 | 1.5 | 1.0 | 0.8 | 4.7 | 6.1 |

*FIG. 3F-1-1*

| Ethnic | 30 | 30 | 30 | 30 | 30 | 30 | 30 | 30 | 40 | 40 | 40 | 40 | 40 |
|---|---|---|---|---|---|---|---|---|---|---|---|---|---|
| code | 401 | 406 | 413 | 601 | 701 | 702 | 801 | 902 | 101 | 104 | 201 | 202 | 204 |
| *N* ~ | 50 | 73 | 50 | 63 | 246 | 197 | 114 | 351 | 1023 | 261 | 145 | 138 | 69 |
| B7 | 8.0 | 8.9 | 2.3 | 10.3 | 10.0 | 11.1 | 6.6 | 5.1 | 5.0 | 4.1 | 3.1 | 0.0 | 0.0 |
| B8 | 0.0 | 3.4 | 9.6 | 12.8 | 10.0 | 11.1 | 3.9 | 4.9 | 0.0 | 0.6 | 0.0 | 0.0 | 0.0 |
| B13 | 2.0 | 4.5 | 2.3 | 3.4 | 3.0 | 2.5 | 0.9 | 1.7 | 1.8 | 6.3 | 16.4 | 8.5 | 13.0 |
| B14 | 0.0 | 0.0 | 0.0 | 4.0 | 4.1 | 6.5 | 6.1 | 5.0 | 0.1 | 0.8 | 0.0 | 0.4 | 0.0 |
| B18 | 7.6 | 0.0 | 5.0 | 5.1 | 4.9 | 5.8 | 5.7 | 5.3 | 0.0 | 0.0 | 0.0 | 0.0 | 0.0 |
| B27 | 4.0 | 0.7 | 0.0 | 3.2 | 4.1 | 4.3 | 1.8 | 3.1 | 0.4 | 3.0 | 1.4 | 1.8 | 2.2 |
| B35 | 12.7 | 14.3 | 10.7 | 7.1 | 8.5 | 7.6 | 14.5 | 13.7 | 8.1 | 7.0 | 3.6 | 2.9 | 1.4 |
| B37 | 1.0 | 3.4 | 4.0 | 0.8 | 2.2 | 1.8 | 0.4 | 0.9 | 0.7 | 1.9 | 2.1 | 0.0 | 0.0 |
| B38 | 0.0 | 0.7 | 0.0 | 1.6 | 4.1 | 1.5 | 1.3 | 3.6 | 0.3 | 1.3 | 1.0 | 2.9 | 10.9 |
| B39 | 0.0 | 0.0 | 0.0 | 0.0 | 1.8 | 2.0 | 6.6 | 4.9 | 4.5 | 1.7 | 1.7 | 2.9 | 3.6 |
| B41 | 2.0 | 1.4 | 4.0 | 3.2 | 1.0 | 0.8 | 1.8 | 1.1 | 0.0 | 0.0 | 0.3 | 0.0 | 0.0 |
| B42 | 2.0 | 0.0 | 0.0 | 0.8 | 0.0 | 0.0 | 0.4 | 0.6 | 0.0 | 0.0 | 0.0 | 0.0 | 0.0 |
| B44 | 15.5 | 10.0 | 10.0 | 15.6 | 10.4 | 13.3 | 11.4 | 10.6 | 7.4 | 9.9 | 4.1 | 1.1 | 0.7 |
| B45 | 0.0 | 0.0 | 0.0 | 0.8 | 0.6 | 0.3 | 1.3 | 2.1 | 0.0 | 0.0 | 0.7 | 0.0 | 0.0 |
| B46 | 0.0 | 0.0 | 0.0 | 0.0 | 0.0 | 0.3 | 0.0 | 0.0 | 4.4 | 4.0 | 2.8 | 15.4 | 21.6 |
| B47 | 0.0 | 1.4 | 0.0 | 0.0 | 0.6 | 0.0 | 0.4 | 0.0 | 0.1 | 0.0 | 0.0 | 1.1 | 0.0 |
| B48 | 0.0 | 0.0 | 0.0 | 0.0 | 0.2 | 0.0 | 2.6 | 0.0 | 3.2 | 4.0 | 2.8 | 0.7 | 0.0 |
| B49 | 2.0 | 2.1 | 0.0 | 0.0 | 2.2 | 2.0 | 2.2 | 3.0 | 0.0 | 0.2 | 0.3 | 0.0 | 0.0 |
| B50 | 0.0 | 0.0 | 6.0 | 0.0 | 2.2 | 1.3 | 3.5 | 1.9 | 0.0 | 0.0 | 0.0 | 0.0 | 0.0 |
| B51 | 2.0 | 10.1 | 6.0 | 2.4 | 3.7 | 4.0 | 3.9 | 7.1 | 9.3 | 7.8 | 11.8 | 4.3 | 5.8 |
| B52 | 6.0 | 6.2 | 11.3 | 0.8 | 1.2 | 0.8 | 3.5 | 1.5 | 10.7 | 2.4 | 2.1 | 1.8 | 0.7 |

FIG. 3F-1-2

| Ethnic | 30 | 30 | 30 | 30 | 30 | 30 | 30 | 30 | 30 | 30 | 30 | 30 | 30 |
|---|---|---|---|---|---|---|---|---|---|---|---|---|---|
| code | 119 | 120 | 121 | 122 | 124 | 125 | 127 | 128 | 129 | 130 | 131 | 141 | 400 |
| *N* ~ | 50 | 125 | 91 | 97 | 264 | 95 | 83 | 97 | 98 | 98 | 61 | 75 | 99 |
| B53 | 0.0 | 0.4 | 0.5 | 0.0 | 0.8 | 0.5 | 1.2 | 2.6 | 1.0 | 1.5 | 0.0 | 0.0 | 1.0 |
| B54 | 0.0 | 0.0 | 0.5 | 0.0 | 0.0 | 0.0 | 0.6 | 0.0 | 0.0 | 0.0 | 0.0 | 0.0 | 0.0 |
| B55 | 1.0 | 1.2 | 2.2 | 1.5 | 2.0 | 0.0 | 1.2 | 0.5 | 1.5 | 1.5 | 1.6 | 2.0 | 2.5 |
| B56 | 2.0 | 0.4 | 0.0 | 0.5 | 0.4 | 0.5 | 0.0 | 0.0 | 0.5 | 1.5 | 0.9 | 0.0 | 1.5 |
| B57 | 1.0 | 3.1 | 1.1 | 2.2 | 2.0 | 0.5 | 0.6 | 1.5 | 3.1 | 4.1 | 3.3 | 4.7 | 3.5 |
| B58 | 5.0 | 1.6 | 1.1 | 9.1 | 1.9 | 2.4 | 1.2 | 5.2 | 1.0 | 1.5 | 0.8 | 2.0 | 2.5 |
| B59 | 0.0 | 0.0 | 0.0 | 0.0 | 0.0 | 0.0 | 0.6 | 0.0 | 0.0 | 0.0 | 0.0 | 0.0 | 0.0 |
| B60 | 6.0 | 1.6 | 2.2 | 0.5 | 1.9 | 6.2 | 1.9 | 7.7 | 1.0 | 0.5 | 3.3 | 0.0 | 2.5 |
| B61 | 0.0 | 0.8 | 1.8 | 2.2 | 1.7 | 0.0 | 1.2 | 1.5 | 2.0 | 3.1 | 0.0 | 21.3 | 12.9 |
| B62 | 3.0 | 4.4 | 2.7 | 0.5 | 3.7 | 4.7 | 5.5 | 3.1 | 3.1 | 3.6 | 5.7 | 1.3 | 5.6 |
| B63 | 3.0 | 0.8 | 0.5 | 0.5 | 1.1 | 4.2 | 1.8 | 0.5 | 0.5 | 2.4 | 0.8 | 0.0 | 1.5 |
| B67 | 0.0 | 0.0 | 0.0 | 0.0 | 0.0 | 0.0 | 0.6 | 0.0 | 0.0 | 0.0 | 0.0 | 0.0 | 0.0 |
| B70 | 0.0 | 2.4 | 0.0 | 0.0 | 0.4 | 0.0 | 0.0 | 0.0 | 0.0 | 0.0 | 0.8 | 0.7 | 0.0 |
| B73 | 0.0 | 0.0 | 0.0 | 0.0 | 0.0 | 0.0 | 0.0 | 0.0 | 0.0 | 0.0 | 0.0 | 0.0 | 0.5 |
| B75 | 0.0 | 0.0 | 0.0 | 0.5 | 0.0 | 0.5 | 0.5 | 4.1 | 0.0 | 0.0 | 1.6 | 0.0 | 0.5 |
| B76 | 0.0 | 0.0 | 0.0 | 0.0 | 0.0 | 0.0 | 0.0 | 0.0 | 0.0 | 0.0 | 0.0 | 0.0 | 0.0 |
| B77 | 0.0 | 0.0 | 0.0 | 0.0 | 0.2 | 0.0 | 0.0 | 0.5 | 0.0 | 0.0 | 0.0 | 0.0 | 0.0 |
| B5102 | 0.0 | 0.0 | 0.0 | 0.0 | 0.0 | 0.0 | 0.0 | 0.0 | 0.0 | 0.5 | 0.0 | 0.0 | 0.0 |
| B7801 | 0.0 | 0.0 | 0.0 | 0.0 | 0.0 | 0.0 | 0.0 | 0.0 | 0.0 | 0.0 | 0.0 | 0.0 | 0.0 |
| BX | 0.0 | 0.0 | 0.5 | 0.5 | 0.0 | 8.9 | 0.0 | 0.0 | 0.0 | 0.0 | 0.0 | 0.0 | 0.5 |
| BBL | 1.7 | 0.8 | 3.3 | 2.7 | 2.0 | 1.1 | 10.7 | 0.0 | 0.0 | 0.7 | 5.0 | 0.0 | 1.6 |

*FIG. 3F-2-1*

| Ethnic | 40 | 40 | 40 | 40 | 40 | 40 | 40 | 40 | 40 | 40 | 40 | 40 | 40 |
|---|---|---|---|---|---|---|---|---|---|---|---|---|---|
| code | 207 | 210 | 211 | 212 | 213 | 215 | 218 | 219 | 220 | 301 | 302 | 303 | 401 |
| N ~ | 70 | 60 | 99 | 187 | 73 | 165 | 87 | 79 | 104 | 89 | 138 | 59 | 242 |
| B53 | 0.0 | 1.7 | 0.5 | 0.0 | 0.0 | 0.0 | 1.1 | 1.3 | 0.0 | 1.1 | 0.4 | 13.3 | 0.0 |
| B54 | 1.4 | 1.7 | 1.5 | 2.9 | 2.1 | 0.0 | 1.7 | 3.2 | 2.4 | 2.8 | 1.4 | 1.7 | 0.6 |
| B55 | 5.9 | 0.8 | 5.6 | 1.9 | 0.7 | 9.3 | 4.0 | 8.2 | 4.3 | 2.2 | 2.2 | 0.8 | 2.5 |
| B56 | 1.4 | 0.0 | 1.0 | 0.3 | 0.0 | 0.6 | 0.0 | 5.5 | 1.9 | 0.0 | 0.7 | 0.8 | 1.4 |
| B57 | 1.5 | 0.0 | 0.5 | 1.3 | 0.0 | 0.0 | 0.0 | 1.3 | 1.0 | 3.9 | 1.8 | 4.3 | 5.2 |
| B58 | 3.6 | 2.5 | 0.0 | 2.9 | 0.0 | 0.9 | 4.8 | 8.2 | 5.5 | 5.8 | 5.1 | 3.4 | 2.9 |
| B59 | 0.0 | 0.0 | 0.0 | 0.3 | 0.0 | 0.0 | 0.0 | 0.0 | 0.0 | 0.0 | 0.4 | 0.0 | 0.0 |
| B60 | 11.8 | 2.5 | 6.4 | 5.4 | 11.6 | 32.3 | 3.6 | 5.1 | 12.8 | 3.4 | 4.0 | 6.2 | 8.3 |
| B61 | 2.3 | 0.9 | 9.0 | 4.8 | 9.6 | 2.8 | 5.2 | 0.6 | 2.4 | 4.7 | 6.9 | 4.3 | 4.3 |
| B62 | 4.5 | 0.9 | 12.6 | 9.8 | 11.6 | 4.2 | 3.8 | 8.2 | 3.4 | 2.8 | 5.4 | 4.3 | 5.0 |
| B63 | 0.0 | 3.3 | 5.2 | 0.3 | 0.0 | 0.0 | 8.3 | 0.6 | 0.0 | 1.8 | 3.3 | 1.7 | 0.4 |
| B67 | 0.7 | 0.0 | 0.0 | 0.5 | 0.0 | 0.3 | 2.3 | 0.0 | 0.0 | 0.0 | 0.7 | 0.0 | 0.0 |
| B70 | 0.0 | 0.0 | 0.5 | 0.5 | 1.4 | 0.0 | 1.7 | 0.0 | 0.5 | 0.0 | 0.4 | 0.8 | 0.0 |
| B73 | 0.0 | 0.0 | 0.0 | 0.0 | 0.0 | 0.0 | 0.0 | 0.0 | 0.0 | 0.0 | 0.0 | 0.0 | 0.0 |
| B75 | 10.0 | 0.9 | 0.5 | 4.2 | 3.4 | 0.3 | 4.6 | 0.0 | 3.0 | 1.7 | 0.0 | 0.9 | 8.3 |
| B76 | 0.7 | 0.0 | 0.0 | 0.0 | 0.0 | 0.0 | 0.0 | 0.7 | 0.0 | 0.0 | 0.0 | 0.0 | 0.0 |
| B77 | 0.7 | 0.0 | 0.0 | 0.0 | 0.7 | 0.0 | 0.0 | 0.0 | 0.0 | 0.0 | 0.0 | 0.0 | 0.4 |
| B5102 | 0.0 | 0.8 | 1.0 | 0.5 | 0.7 | 0.0 | 0.0 | 1.3 | 0.5 | 0.6 | 0.4 | 0.0 | 0.0 |
| B7801 | 0.0 | 0.0 | 0.0 | 0.0 | 0.0 | 0.0 | 0.0 | 0.0 | 0.0 | 0.0 | 0.0 | 0.8 | 0.0 |
| BX | 0.7 | 0.0 | 0.0 | 0.3 | 0.0 | 0.0 | 0.0 | 0.0 | 0.0 | 0.0 | 0.0 | 0.0 | 0.4 |
| BBL | 6.2 | 18.3 | 7.0 | 4.8 | 0.2 | 3.5 | 4.9 | 1.7 | 5.4 | 12.2 | 2.7 | 17.2 | 0.0 |

FIG. 3F-2-1

| Ethnic | 30 | 30 | 30 | 30 | 30 | 30 | 30 | 30 | 40 | 40 | 40 | 40 | 40 |
|---|---|---|---|---|---|---|---|---|---|---|---|---|---|
| code | 401 | 406 | 413 | 601 | 701 | 702 | 801 | 902 | 101 | 104 | 201 | 202 | 204 |
| *N* ~ | 50 | 73 | 50 | 63 | 246 | 197 | 114 | 351 | 1023 | 261 | 145 | 138 | 69 |
| B53 | 4.5 | 0.7 | 1.0 | 0.8 | 0.8 | 0.8 | 1.3 | 1.5 | 0.0 | 0.0 | 0.7 | 0.0 | 0.0 |
| B54 | 1.0 | 0.7 | 0.0 | 0.0 | 0.0 | 0.0 | 0.0 | 0.1 | 6.3 | 6.5 | 2.4 | 4.9 | 0.7 |
| B55 | 3.0 | 4.1 | 0.0 | 2.4 | 2.2 | 1.3 | 0.9 | 2.0 | 2.9 | 1.8 | 3.2 | 4.0 | 7.9 |
| B56 | 0.0 | 0.0 | 0.0 | 0.8 | 1.0 | 1.5 | 0.0 | 0.0 | 1.6 | 0.6 | 0.3 | 0.0 | 1.4 |
| B57 | 1.2 | 7.5 | 3.0 | 4.5 | 3.9 | 3.6 | 2.2 | 2.2 | 0.0 | 0.8 | 2.8 | 1.1 | 1.8 |
| B58 | 2.0 | 0.7 | 6.0 | 0.0 | 1.0 | 0.5 | 2.2 | 1.0 | 0.7 | 5.2 | 3.2 | 4.9 | 2.2 |
| B59 | 0.0 | 0.0 | 0.0 | 0.0 | 0.0 | 0.0 | 0.0 | 0.0 | 1.9 | 1.0 | 0.0 | 0.0 | 0.0 |
| B60 | 3.0 | 3.1 | 2.0 | 2.4 | 4.5 | 5.6 | 3.1 | 2.4 | 5.6 | 4.2 | 6.0 | 17.1 | 11.5 |
| B61 | 4.0 | 4.1 | 8.0 | 4.0 | 3.3 | 0.5 | 4.4 | 1.9 | 10.7 | 9.2 | 4.2 | 5.4 | 0.7 |
| B62 | 5.0 | 3.8 | 1.0 | 6.7 | 5.5 | 7.0 | 0.9 | 4.2 | 8.3 | 10.5 | 11.8 | 14.7 | 5.8 |
| B63 | 4.0 | 4.1 | 1.0 | 0.8 | 0.4 | 1.0 | 0.4 | 0.7 | 0.0 | 0.0 | 2.6 | 0.0 | 0.7 |
| B67 | 0.0 | 0.0 | 0.0 | 0.0 | 0.0 | 0.3 | 0.0 | 0.1 | 1.5 | 0.4 | 0.0 | 0.4 | 0.0 |
| B70 | 4.0 | 0.7 | 2.0 | 0.8 | 1.6 | 0.3 | 3.1 | 1.0 | 1.6 | 1.9 | 0.4 | 0.4 | 0.0 |
| B73 | 0.0 | 0.0 | 0.0 | 0.0 | 0.4 | 0.0 | 0.4 | 0.0 | 0.0 | 0.0 | 0.3 | 0.0 | 0.0 |
| B75 | 0.0 | 1.4 | 1.0 | 0.0 | 0.0 | 0.0 | 1.8 | 1.0 | 1.1 | 1.7 | 2.4 | 1.1 | 6.4 |
| B76 | 1.0 | 0.0 | 0.0 | 0.0 | 0.2 | 0.0 | 0.0 | 0.0 | 0.0 | 0.0 | 0.0 | 0.0 | 0.0 |
| B77 | 0.0 | 0.0 | 0.0 | 0.0 | 0.0 | 0.0 | 0.0 | 0.0 | 0.0 | 0.0 | 0.0 | 0.0 | 0.0 |
| B5102 | 0.0 | 0.7 | 1.0 | 0.0 | 0.0 | 0.0 | 0.0 | 0.9 | 0.3 | 0.0 | 0.3 | 0.4 | 0.0 |
| B7801 | 0.0 | 0.0 | 0.0 | 0.0 | 0.0 | 0.0 | 0.0 | 0.0 | 0.0 | 0.0 | 0.0 | 0.0 | 0.0 |
| BX | 0.0 | 0.0 | 0.0 | 0.8 | 0.4 | 0.3 | 0.4 | 2.0 | 0.0 | 0.0 | 0.0 | 0.4 | 0.0 |
| BBL | 2.5 | 1.5 | 2.8 | 4.4 | 0.0 | 0.6 | 0.0 | 3.0 | 1.3 | 1.3 | 4.8 | 1.6 | 0.8 |

FIG. 3F-2-2

| Ethnic | 40 | 40 | 40 | 40 | 40 | 40 | 40 | 40 | 40 | 40 | 40 | 40 | 40 |
|---|---|---|---|---|---|---|---|---|---|---|---|---|---|
| code | 207 | 210 | 211 | 212 | 213 | 215 | 218 | 219 | 220 | 301 | 302 | 303 | 401 |
| N ~ | 70 | 60 | 99 | 187 | 73 | 165 | 87 | 79 | 104 | 89 | 138 | 59 | 242 |
| B7 | 0.8 | 2.6 | 0.0 | 2.0 | 2.1 | 0.3 | 3.4 | 8.0 | 5.3 | 4.6 | 3.5 | 4.2 | 2.7 |
| B8 | 0.7 | 7.5 | 1.0 | 1.1 | 0.7 | 0.0 | 0.6 | 0.0 | 4.1 | 0.0 | 6.4 | 4.2 | 0.2 |
| B13 | 10.7 | 12.7 | 0.5 | 11.4 | 1.4 | 9.4 | 13.1 | 18.7 | 7.2 | 4.7 | 6.2 | 1.7 | 9.3 |
| B14 | 0.0 | 4.3 | 0.0 | 1.6 | 0.0 | 0.0 | 1.8 | 0.0 | 0.5 | 0.0 | 0.7 | 1.7 | 0.4 |
| B18 | 0.0 | 0.0 | 0.5 | 0.0 | 0.0 | 0.0 | 1.1 | 0.0 | 1.9 | 1.1 | 1.1 | 0.0 | 2.5 |
| B27 | 0.7 | 3.3 | 10.5 | 2.4 | 2.1 | 3.4 | 4.0 | 2.5 | 2.4 | 2.8 | 5.1 | 4.4 | 6.0 |
| B35 | 0.7 | 1.7 | 5.2 | 5.4 | 6.8 | 0.0 | 4.6 | 2.5 | 4.3 | 5.2 | 6.6 | 1.7 | 2.5 |
| B37 | 1.5 | 0.0 | 1.0 | 3.8 | 2.1 | 0.3 | 2.9 | 0.0 | 3.5 | 2.3 | 4.3 | 0.0 | 1.4 |
| B38 | 2.9 | 4.3 | 4.7 | 0.3 | 0.7 | 0.0 | 4.0 | 0.6 | 2.5 | 0.0 | 2.2 | 0.0 | 3.5 |
| B39 | 1.4 | 0.0 | 1.0 | 1.4 | 0.7 | 15.8 | 0.0 | 1.3 | 2.0 | 0.0 | 2.2 | 1.7 | 1.7 |
| B41 | 0.0 | 0.0 | 0.0 | 0.5 | 0.0 | 0.0 | 0.0 | 0.6 | 0.0 | 2.8 | 1.4 | 0.8 | 0.0 |
| B42 | 0.0 | 0.0 | 0.5 | 0.0 | 0.0 | 0.0 | 0.0 | 0.0 | 0.0 | 0.0 | 0.0 | 0.8 | 0.2 |
| B44 | 0.0 | 4.3 | 1.0 | 6.5 | 1.4 | 0.3 | 4.8 | 8.2 | 4.3 | 11.4 | 1.4 | 2.5 | 5.4 |
| B45 | 0.7 | 0.0 | 0.0 | 0.0 | 0.7 | 0.0 | 0.0 | 0.0 | 1.4 | 1.8 | 0.0 | 0.8 | 0.0 |
| B46 | 18.4 | 3.5 | 1.0 | 5.6 | 0.7 | 1.2 | 4.0 | 3.8 | 2.4 | 1.7 | 1.1 | 0.8 | 14.0 |
| B47 | 1.4 | 0.8 | 0.5 | 0.0 | 0.0 | 0.3 | 0.0 | 0.0 | 0.0 | 0.6 | 0.0 | 0.0 | 0.0 |
| B48 | 0.7 | 0.8 | 5.9 | 5.1 | 19.8 | 14.5 | 1.7 | 0.6 | 1.4 | 3.9 | 4.7 | 0.8 | 1.0 |
| B49 | 0.7 | 1.7 | 0.0 | 0.0 | 0.0 | 0.0 | 0.0 | 1.5 | 0.5 | 0.0 | 0.0 | 0.8 | 0.0 |
| B50 | 0.0 | 3.5 | 1.0 | 1.9 | 1.4 | 0.0 | 0.6 | 0.0 | 2.4 | 0.0 | 2.9 | 0.0 | 0.0 |
| B51 | 6.4 | 6.9 | 13.4 | 6.5 | 17.8 | 0.3 | 3.8 | 5.7 | 9.4 | 11.4 | 8.7 | 8.5 | 6.4 |
| B52 | 0.7 | 7.9 | 1.0 | 2.7 | 0.0 | 0.0 | 3.4 | 0.0 | 1.4 | 2.8 | 5.8 | 3.5 | 3.1 |

FIG. 3G-1-1

| Ethnic | 40 | 40 | 40 | 40 | 40 | 40 | 40 | 40 | 41 | 41 | 41 | 41 |
|---|---|---|---|---|---|---|---|---|---|---|---|---|
| code | 402 | 403 | 414 | 416 | 421 | 602 | 800 | 803 | 003 | 00A | 102 | 10A |
| *N* ~ | 71 | 149 | 68 | 51 | 73 | 53 | 51 | 56 | 61 | 72 | 156 | 79 |
| B7 | 3.5 | 12.2 | 1.5 | 2.0 | 2.1 | 3.8 | 3.9 | 5.8 | 0.8 | 3.3 | 2.2 | 3.2 |
| B8 | 0.0 | 0.3 | 0.0 | 0.0 | 0.7 | 0.9 | 5.6 | 1.8 | 0.8 | 1.4 | 2.2 | 0.0 |
| B13 | 9.9 | 7.4 | 2.3 | 10.5 | 6.8 | 1.9 | 1.0 | 0.9 | 0.8 | 0.0 | 0.0 | 3.8 |
| B14 | 0.0 | 0.7 | 0.0 | 0.0 | 0.0 | 0.9 | 2.9 | 0.9 | 5.9 | 0.7 | 0.0 | 0.0 |
| B18 | 1.4 | 1.3 | 6.4 | 2.0 | 0.0 | 1.9 | 1.0 | 1.8 | 0.0 | 1.4 | 0.0 | 0.6 |
| B27 | 4.9 | 3.2 | 3.8 | 6.2 | 3.7 | 0.9 | 2.9 | 10.1 | 0.0 | 0.0 | 10.7 | 9.2 |
| B35 | 3.5 | 5.0 | 12.0 | 5.9 | 2.1 | 0.9 | 18.6 | 12.7 | 29.0 | 29.8 | 4.7 | 6.6 |
| B37 | 0.7 | 0.7 | 0.0 | 0.0 | 0.0 | 0.0 | 0.0 | 2.7 | 0.0 | 0.0 | 0.6 | 7.6 |
| B38 | 1.4 | 4.2 | 0.0 | 2.0 | 4.1 | 0.9 | 0.0 | 0.0 | 0.8 | 5.6 | 0.0 | 1.9 |
| B39 | 1.4 | 2.7 | 0.0 | 0.0 | 2.9 | 9.4 | 17.4 | 0.0 | 18.3 | 17.9 | 1.0 | 0.0 |
| B41 | 0.0 | 0.3 | 0.0 | 2.0 | 0.0 | 0.0 | 0.0 | 0.0 | 0.0 | 0.0 | 0.3 | 0.0 |
| B42 | 0.0 | 0.0 | 0.0 | 0.0 | 0.0 | 0.0 | 0.0 | 0.0 | 0.0 | 0.0 | 0.0 | 0.0 |
| B44 | 2.8 | 3.4 | 6.9 | 0.0 | 0.7 | 0.9 | 3.9 | 0.0 | 0.0 | 2.8 | 1.3 | 4.4 |
| B45 | 0.0 | 0.7 | 0.0 | 0.0 | 0.0 | 0.0 | 0.0 | 0.0 | 0.0 | 0.0 | 0.3 | 0.0 |
| B46 | 7.7 | 13.2 | 2.9 | 2.0 | 15.1 | 0.0 | 0.0 | 0.0 | 0.0 | 0.0 | 0.0 | 0.0 |
| B47 | 0.0 | 0.0 | 0.0 | 0.0 | 1.5 | 0.0 | 0.0 | 0.9 | 0.0 | 0.0 | 1.3 | 0.6 |
| B48 | 1.4 | 1.3 | 0.0 | 3.9 | 6.2 | 3.8 | 6.6 | 4.5 | 2.5 | 3.5 | 9.9 | 6.3 |
| B49 | 0.0 | 0.0 | 0.0 | 1.0 | 0.0 | 0.0 | 2.0 | 0.0 | 0.0 | 2.1 | 0.0 | 0.0 |
| B50 | 0.0 | 0.3 | 0.0 | 0.0 | 0.0 | 0.0 | 0.0 | 0.0 | 0.0 | 0.0 | 0.3 | 3.2 |
| B51 | 4.2 | 1.3 | 4.4 | 5.0 | 4.1 | 0.0 | 11.8 | 1.8 | 13.3 | 3.5 | 14.8 | 5.9 |
| B52 | 2.1 | 1.0 | 9.8 | 1.0 | 0.7 | 0.0 | 2.9 | 0.0 | 0.8 | 3.5 | 0.0 | 0.0 |

FIG. 3G-1-2

| Ethnic | 40 | 40 | 40 | 40 | 40 | 40 | 40 | 40 | 41 | 41 | 41 | 41 |
|---|---|---|---|---|---|---|---|---|---|---|---|---|
| code | 402 | 403 | 414 | 416 | 421 | 602 | 800 | 803 | 003 | 00A | 102 | 10A |
| *N* ~ | 71 | 149 | 68 | 51 | 73 | 53 | 51 | 56 | 61 | 72 | 156 | 79 |
| B53 | 0.0 | 0.0 | 0.0 | 0.0 | 0.0 | 0.0 | 0.0 | 4.5 | 0.0 | 1.4 | 0.6 | 0.6 |
| B54 | 2.1 | 1.7 | 0.0 | 0.0 | 2.9 | 0.0 | 0.0 | 0.0 | 0.0 | 0.0 | 0.0 | 0.0 |
| B55 | 1.4 | 1.0 | 0.7 | 0.0 | 1.4 | 22.6 | 0.0 | 0.0 | 0.0 | 0.0 | 0.0 | 0.6 |
| B56 | 0.7 | 1.7 | 1.5 | 0.0 | 2.1 | 17.0 | 0.0 | 0.9 | 0.0 | 0.0 | 0.0 | 0.0 |
| B57 | 1.4 | 2.7 | 2.2 | 0.0 | 0.0 | 0.0 | 1.0 | 0.0 | 0.0 | 0.0 | 0.0 | 2.7 |
| B58 | 15.5 | 3.0 | 1.5 | 3.1 | 7.2 | 1.9 | 0.0 | 0.9 | 0.0 | 0.7 | 0.0 | 5.9 |
| B59 | 0.7 | 0.0 | 0.0 | 0.0 | 0.0 | 0.0 | 0.0 | 0.0 | 0.0 | 0.0 | 0.0 | 0.0 |
| B60 | 16.2 | 3.2 | 1.5 | 1.0 | 11.4 | 15.1 | 2.9 | 25.7 | 1.7 | 0.0 | 1.3 | 7.5 |
| B61 | 2.8 | 1.7 | 0.0 | 1.0 | 2.1 | 8.5 | 9.4 | 6.7 | 1.7 | 13.0 | 27.3 | 6.2 |
| B62 | 7.0 | 10.1 | 26.7 | 32.4 | 4.1 | 2.8 | 4.9 | 3.7 | 6.9 | 4.2 | 16.9 | 16.0 |
| B63 | 0.7 | 1.1 | 0.0 | 1.0 | 7.9 | 0.0 | 0.0 | 0.9 | 0.0 | 0.0 | 1.6 | 0.6 |
| B67 | 0.0 | 0.0 | 0.0 | 0.0 | 0.7 | 1.9 | 0.0 | 0.0 | 0.0 | 0.0 | 0.0 | 0.6 |
| B70 | 0.7 | 0.7 | 0.0 | 0.0 | 0.7 | 0.0 | 0.0 | 0.0 | 0.8 | 3.5 | 0.0 | 0.6 |
| B73 | 0.0 | 0.3 | 0.0 | 0.0 | 0.0 | 0.9 | 0.0 | 0.0 | 0.0 | 0.0 | 0.0 | 0.0 |
| B75 | 4.2 | 6.7 | 0.7 | 2.0 | 0.0 | 2.8 | 0.0 | 3.6 | 0.8 | 0.7 | 0.0 | 0.6 |
| B76 | 1.4 | 2.1 | 0.0 | 0.0 | 2.1 | 0.0 | 0.0 | 0.0 | 0.0 | 0.0 | 0.3 | 0.0 |
| B77 | 0.0 | 0.0 | 0.7 | 0.0 | 0.0 | 0.0 | 0.0 | 0.0 | 0.0 | 0.0 | 0.0 | 0.0 |
| B5102 | 0.0 | 1.3 | 0.0 | 0.0 | 3.4 | 0.0 | 0.0 | 0.0 | 0.0 | 0.7 | 0.0 | 0.0 |
| B7801 | 0.0 | 0.0 | 0.0 | 0.0 | 0.0 | 0.0 | 0.0 | 0.0 | 0.0 | 0.0 | 0.0 | 0.0 |
| BX | 0.0 | 1.7 | 0.0 | 0.0 | 0.0 | 0.0 | 0.0 | 0.0 | 0.0 | 0.0 | 0.6 | 0.0 |
| BBL | 0.0 | 1.8 | 14.4 | 16.1 | 3.6 | 0.0 | 1.2 | 9.4 | 14.9 | 0.6 | 1.7 | 4.5 |

FIG. 3G-2-2

| Ethnic | 10 | 10 | 10 | 10 | 10 | 10 | 10 | 10 | 10 | 10 | 10 | 20 | 20 |
|---|---|---|---|---|---|---|---|---|---|---|---|---|---|
| code | 100 | 102 | 200 | 201 | 202 | 204 | 206 | 207 | 210 | 400 | 600 | 100 | 202 |
| *N* ~ | 59 | 99 | 103 | 103 | 65 | 90 | 61 | 70 | 105 | 417 | 116 | 99 | 51 |
| Cw1 | 1.7 | 5.1 | 0.0 | 0.0 | 0.8 | 0.0 | 1.7 | 0.7 | 1.4 | 1.1 | 2.2 | 22.9 | 27.3 |
| Cw2 | 6.1 | 7.3 | 13.8 | 14.6 | 11.5 | 10.2 | 17.0 | 14.8 | 8.7 | 9.7 | 6.8 | 8.7 | 0.0 |
| Cw4 | 11.8 | 17.0 | 7.0 | 14.6 | 20.6 | 15.3 | 17.1 | 15.1 | 11.6 | 21.0 | 21.5 | 17.6 | 37.2 |
| Cw5 | 6.0 | 3.5 | 0.5 | 0.0 | 0.8 | 0.0 | 1.7 | 0.0 | 1.4 | 2.4 | 2.2 | 4.1 | 0.0 |
| Cw6 | 8.0 | 5.7 | 19.4 | 33.0 | 19.7 | 18.4 | 11.2 | 11.0 | 23.2 | 7.4 | 9.0 | 16.1 | 2.0 |
| Cw7 | 13.7 | 13.8 | 25.8 | 33.5 | 31.4 | 19.2 | 19.8 | 13.8 | 29.9 | 15.6 | 17.8 | 14.1 | 2.0 |
| Cw9 | 7.0 | 1.0 | 2.0 | 1.0 | 0.0 | 5.6 | 5.0 | 3.6 | 4.0 | 2.3 | 9.0 | 5.8 | 11.0 |
| Cw10 | 1.7 | 15.1 | 4.4 | 1.0 | 0.0 | 4.0 | 0.2 | 4.4 | 5.0 | 4.1 | 2.6 | 0.5 | 2.9 |
| Cw11 | 0.0 | 0.0 | 0.0 | 0.0 | 0.0 | 0.0 | 0.8 | 0.0 | 0.5 | 0.0 | 0.4 | 0.0 | 0.0 |
| CwX | 3.4 | 1.0 | 0.0 | 2.1 | 3.3 | 1.7 | 0.0 | 0.0 | 5.1 | 1.0 | 0.0 | 0.5 | 2.0 |
| CBL | 40.5 | 29.8 | 27.1 | 0.0 | 11.9 | 25.5 | 21.6 | 36.5 | 9.3 | 34.6 | 28.4 | 9.7 | 15.6 |

FIG. 3H-1

| Ethnic | 30 | 30 | 30 | 30 | 30 | 30 | 30 | 30 | 30 | 30 | 30 | 30 | 30 |
|---|---|---|---|---|---|---|---|---|---|---|---|---|---|
| code | 101 | 102 | 103 | 104 | 105 | 106 | 109 | 110 | 111 | 113 | 114 | 115 | 117 |
| *N* ~ | 208 | 141 | 98 | 60 | 64 | 117 | 101 | 96 | 150 | 321 | 295 | 231 | 551 |
| Cw1 | 2.9 | 4.4 | 3.6 | 5.9 | 5.6 | 3.5 | 4.2 | 4.7 | 4.0 | 4.2 | 3.3 | 2.6 | 3.1 |
| Cw2 | 5.5 | 2.5 | 5.6 | 4.3 | 1.6 | 4.3 | 2.0 | 4.8 | 6.9 | 5.2 | 7.2 | 6.5 | 4.0 |
| Cw4 | 14.2 | 9.6 | 14.1 | 8.7 | 11.5 | 11.4 | 7.8 | 13.1 | 9.2 | 11.1 | 11.2 | 16.2 | 17.1 |
| Cw5 | 2.2 | 1.4 | 5.3 | 6.8 | 5.5 | 3.1 | 12.4 | 4.9 | 4.4 | 5.8 | 4.7 | 2.4 | 5.7 |
| Cw6 | 5.4 | 10.2 | 13.1 | 6.1 | 5.6 | 12.1 | 0.8 | 12.9 | 9.9 | 8.9 | 14.2 | 6.7 | 10.1 |
| Cw7 | 18.4 | 19.7 | 38.8 | 24.5 | 28.3 | 25.5 | 35.9 | 24.3 | 20.0 | 20.8 | 28.0 | 15.1 | 22.1 |
| Cw9 | 2.9 | 3.3 | 4.6 | 5.3 | 5.7 | 6.6 | 10.0 | 7.1 | 7.0 | 7.4 | 5.3 | 4.5 | 2.1 |
| Cw10 | 2.9 | 0.7 | 5.3 | 0.8 | 2.4 | 4.5 | 6.6 | 4.2 | 9.6 | 2.7 | 4.8 | 2.6 | 0.7 |
| Cw11 | 0.5 | 0.4 | 0.0 | 0.0 | 0.0 | 0.0 | 0.0 | 0.0 | 0.0 | 0.0 | 0.3 | 0.0 | 0.1 |
| CwX | 0.2 | 2.5 | 0.0 | 0.0 | 1.6 | 1.7 | 0.0 | 0.0 | 0.7 | 0.8 | 1.7 | 0.0 | 1.7 |
| CBL | 45.0 | 45.3 | 9.6 | 37.5 | 32.2 | 27.3 | 12.4 | 24.0 | 28.3 | 30.2 | 19.3 | 43.5 | 32.7 |

*FIG. 3H-2*

| Ethnic | 30 | 30 | 30 | 30 | 30 | 30 | 30 | 30 | 30 | 30 | 30 | 30 | 30 |
|---|---|---|---|---|---|---|---|---|---|---|---|---|---|
| code | 119 | 120 | 121 | 122 | 124 | 125 | 127 | 128 | 129 | 130 | 131 | 141 | 400 |
| *N* ~ | 50 | 125 | 91 | 97 | 264 | 95 | 83 | 97 | 98 | 98 | 61 | 75 | 99 |
| Cw1 | 2.1 | 1.2 | 5.1 | 3.1 | 3.1 | 3.7 | 1.8 | 11.4 | 3.1 | 3.1 | 5.0 | 0.0 | 5.7 |
| Cw2 | 8.2 | 7.0 | 6.8 | 5.8 | 4.1 | 7.7 | 4.9 | 6.2 | 8.0 | 7.9 | 3.3 | 11.5 | 2.5 |
| Cw4 | 18.1 | 15.7 | 11.7 | 12.1 | 17.8 | 9.3 | 6.1 | 7.3 | 12.7 | 14.3 | 14.5 | 9.7 | 13.4 |
| Cw5 | 1.0 | 4.1 | 1.1 | 22.0 | 9.7 | 3.7 | 6.9 | 2.6 | 6.4 | 3.7 | 3.3 | 4.1 | 0.5 |
| Cw6 | 10.8 | 5.4 | 7.5 | 7.3 | 9.6 | 3.7 | 10.8 | 11.2 | 4.7 | 13.9 | 7.6 | 16.3 | 11.2 |
| Cw7 | 16.6 | 17.0 | 17.8 | 25.9 | 24.3 | 26.3 | 15.5 | 20.6 | 33.2 | 21.1 | 20.2 | 12.9 | 23.7 |
| Cw9 | 6.2 | 5.3 | 2.8 | 0.5 | 4.5 | 5.3 | 3.7 | 17.4 | 3.1 | 5.7 | 9.3 | 2.7 | 2.5 |
| Cw10 | 3.1 | 1.6 | 4.5 | 0.5 | 2.3 | 7.6 | 1.8 | 3.6 | 8.7 | 1.0 | 5.0 | 0.0 | 3.6 |
| Cw11 | 0.0 | 0.0 | 0.0 | 0.0 | 0.0 | 0.0 | 0.0 | 7.1 | 2.1 | 0.5 | 0.0 | 0.0 | 0.5 |
| CwX | 0.0 | 0.0 | 1.1 | 0.5 | 1.5 | 6.1 | 0.0 | 0.0 | 0.0 | 0.0 | 0.0 | 0.0 | 0.5 |
| CBL | 34.0 | 42.8 | 41.7 | 22.2 | 28.1 | 26.5 | 48.4 | 10.7 | 18.1 | 28.8 | 31.7 | 43.0 | 35.7 |

FIG. 3H-3

| Ethnic | 30 | 30 | 30 | 30 | 30 | 30 | 30 | 30 | 40 | 40 | 40 | 40 | 40 |
|---|---|---|---|---|---|---|---|---|---|---|---|---|---|
| code | 401 | 406 | 413 | 601 | 701 | 702 | 801 | 902 | 101 | 104 | 201 | 202 | 204 |
| *N* ~ | 50 | 73 | 50 | 63 | 246 | 197 | 114 | 351 | 1023 | 261 | 145 | 138 | 69 |
| Cw1 | 9.4 | 5.9 | 5.1 | 3.2 | 4.3 | 5.5 | 1.8 | 2.7 | 11.8 | 12.7 | 12.9 | 16.3 | 6.0 |
| Cw2 | 10.4 | 2.1 | 0.0 | 4.8 | 5.4 | 8.4 | 3.1 | 6.4 | 0.1 | 0.8 | 1.4 | 1.1 | 1.4 |
| Cw4 | 11.2 | 19.3 | 9.6 | 12.2 | 9.8 | 10.0 | 15.0 | 16.4 | 4.2 | 5.9 | 4.2 | 8.0 | 3.7 |
| Cw5 | 2.0 | 0.0 | 0.0 | 9.8 | 3.7 | 6.4 | 3.1 | 3.9 | 0.4 | 0.8 | 0.3 | 0.0 | 0.0 |
| Cw6 | 8.0 | 17.0 | 18.9 | 7.6 | 9.5 | 9.4 | 5.4 | 6.6 | 1.0 | 7.5 | 7.3 | 4.4 | 2.2 |
| Cw7 | 16.2 | 24.1 | 19.5 | 27.6 | 21.5 | 28.9 | 22.0 | 22.1 | 25.3 | 12.8 | 6.5 | 16.8 | 22.9 |
| Cw9 | 10.0 | 4.9 | 3.0 | 3.2 | 3.9 | 7.2 | 2.7 | 7.4 | 13.9 | 13.8 | 8.8 | 14.8 | 11.1 |
| Cw10 | 4.1 | 2.8 | 3.1 | 2.4 | 3.9 | 5.7 | 7.7 | 2.8 | 8.8 | 11.0 | 4.9 | 9.0 | 9.0 |
| Cw11 | 9.4 | 0.7 | 0.0 | 0.0 | 0.2 | 0.5 | 0.0 | 0.0 | 4.2 | 3.9 | 2.5 | 3.6 | 19.1 |
| CwX | 0.0 | 0.0 | 0.0 | 5.0 | 3.3 | 5.4 | 0.9 | 1.0 | 0.6 | 0.2 | 0.0 | 0.0 | 0.0 |
| CBL | 19.2 | 22.5 | 40.7 | 24.2 | 34.4 | 16.6 | 34.1 | 30.6 | 39.5 | 30.7 | 51.1 | 26.0 | 24.4 |

*FIG. 3H-4*

| Ethnic | 40 | 40 | 40 | 40 | 4 | 40 | 40 | 40 | 40 | 40 | 40 | 40 | 40 |
|---|---|---|---|---|---|---|---|---|---|---|---|---|---|
| code | 207 | 210 | 211 | 212 | 213 | 216 | 218 | 219 | 220 | 301 | 302 | 303 | 401 |
| *N* ~ | 70 | 60 | 99 | 187 | 73 | 165 | 87 | 79 | 104 | 89 | 138 | 59 | 242 |
| Cw1 | 14.3 | 2.5 | 9.7 | 7.5 | 4.2 | 11.1 | 8.5 | 13.2 | 12.5 | 5.7 | 9.1 | 6.9 | 3.3 |
| Cw2 | 1.4 | 3.4 | 1.5 | 0.8 | 2.1 | 0.6 | 1.2 | 28.9 | 1.4 | 1.7 | 2.9 | 4.3 | 2.7 |
| Cw4 | 0.7 | 9.6 | 16.1 | 4.4 | 6.2 | 7.4 | 5.3 | 14.6 | 5.0 | 11.6 | 4.3 | 8.7 | 3.6 |
| Cw5 | 0.0 | 4.3 | 0.0 | 2.4 | 0.0 | 0.0 | 1.2 | 5.2 | 1.5 | 0.0 | 0.0 | 8.8 | 0.6 |
| Cw6 | 3.6 | 9.7 | 2.5 | 13.3 | 4.2 | 0.0 | 15.8 | 5.9 | 16.4 | 8.8 | 13.6 | 4.3 | 7.2 |
| Cw7 | 15.9 | 7.9 | 16.8 | 15.1 | 15.2 | 21.5 | 5.3 | 10.3 | 13.1 | 8.1 | 17.2 | 5.2 | 25.5 |
| Cw9 | 18.7 | 0.8 | 8.9 | 15.2 | 20.9 | 14.2 | 9.7 | 6.3 | 22.1 | 8.1 | 7.6 | 9.1 | 14.2 |
| Cw10 | 6.6 | 4.2 | 7.9 | 8.4 | 15.3 | 17.2 | 7.3 | 6.1 | 5.4 | 13.0 | 17.1 | 18.6 | 6.9 |
| Cw11 | 5.2 | 1.7 | 2.6 | 3.9 | 0.7 | 1.2 | 2.9 | 2.5 | 2.4 | 3.4 | 1.8 | 0.0 | 13.2 |
| CwX | 0.0 | 0.0 | 0.0 | 0.0 | 0.0 | 1.5 | 0.0 | 0.0 | 0.0 | 0.0 | 0.0 | 0.0 | 0.6 |
| CBL | 33.5 | 55.8 | 34.0 | 29.1 | 31.1 | 25.2 | 43.0 | 7.1 | 20.2 | 39.6 | 26.4 | 34.2 | 22.1 |

FIG. 3H-5

| Ethnic | 40 | 40 | 40 | 40 | 40 | 40 | 40 | 40 | 41 | 41 | 41 | 41 |
|---|---|---|---|---|---|---|---|---|---|---|---|---|
| code | 402 | 403 | 414 | 416 | 421 | 602 | 800 | 803 | 003 | 00A | 102 | 10A |
| *N* ~ | 71 | 149 | 68 | 51 | 73 | 53 | 51 | 56 | 61 | 72 | 156 | 79 |
| Cw1 | 4.3 | 3.4 | 3.7 | 5.0 | 11.8 | 38.7 | 2.9 | 3.6 | 7.5 | 14.9 | 0.6 | 3.2 |
| Cw2 | 0.0 | 0.0 | 0.7 | 4.9 | 2.1 | 0.9 | 1.0 | 10.5 | 2.5 | 0.7 | 12.1 | 9.8 |
| Cw4 | 6.5 | 7.3 | 10.0 | 9.2 | 4.8 | 10.8 | 22.9 | 11.3 | 13.8 | 17.1 | 5.6 | 12.7 |
| Cw5 | 0.0 | 1.0 | 0.0 | 2.0 | 0.0 | 0.0 | 1.0 | 0.0 | 0.0 | 0.0 | 0.3 | 1.3 |
| Cw6 | 6.0 | 6.9 | 0.7 | 4.0 | 6.2 | 9.8 | 2.9 | 7.5 | 0.0 | 11.0 | 1.0 | 14.6 |
| Cw7 | 24.0 | 18.8 | 14.1 | 10.5 | 18.6 | 21.6 | 30.7 | 2.7 | 34.3 | 23.9 | 4.5 | 6.8 |
| Cw9 | 10.3 | 2.0 | 2.2 | 8.1 | 1.5 | 6.2 | 6.3 | 8.5 | 8.4 | 3.5 | 33.1 | 14.8 |
| Cw10 | 19.5 | 8.0 | 0.0 | 2.0 | 34.8 | 4.0 | 13.1 | 10.5 | 4.3 | 7.8 | 19.8 | 16.7 |
| Cw11 | 7.3 | 11.8 | 0.8 | 2.0 | 15.0 | 0.0 | 0.0 | 1.8 | 0.8 | 0.0 | 0.0 | 1.3 |
| CwX | 7.9 | 4.8 | 0.0 | 1.9 | 1.4 | 0.0 | 6.3 | 5.2 | 0.0 | 0.0 | 0.3 | 0.0 |
| CBL | 14.2 | 36.0 | 68.5 | 52.4 | 4.0 | 8.1 | 13.3 | 38.0 | 0.4 | - | - | - |

*FIG. 3H-6*

| Ethnic | 10 | 10 | 10 | 10 | 10 | 10 | 10 | 10 | 10 | 10 | 10 | 20 | 20 |
|---|---|---|---|---|---|---|---|---|---|---|---|---|---|
| code | 100 | 102 | 200 | 201 | 202 | 204 | 206 | 207 | 210 | 400 | 600 | 100 | 202 |
| *N* ~ | 59 | 99 | 103 | 103 | 65 | 90 | 61 | 70 | 105 | 447 | 116 | 99 | 51 |
| Cw1 | 1.7 | 5.1 | 0.0 | 0.0 | 0.8 | 0.0 | 1.7 | 0.7 | 1.4 | 1.1 | 2.2 | 22.9 | 27.3 |
| Cw2 | 6.1 | 7.3 | 13.8 | 14.6 | 11.5 | 10.2 | 17.0 | 14.8 | 8.7 | 9.7 | 6.8 | 8.7 | 0.0 |
| Cw4 | 11.8 | 17.8 | 7.0 | 14.6 | 20.6 | 15.3 | 17.1 | 15.1 | 11.6 | 21.0 | 21.5 | 17.6 | 37.1 |
| Cw5 | 6.0 | 3.5 | 0.5 | 0.0 | 0.8 | 0.0 | 1.7 | 0.0 | 1.4 | 2.4 | 2.2 | 4.1 | 0.0 |
| Cw6 | 8.0 | 5.7 | 19.4 | 33.0 | 19.7 | 18.4 | 11.2 | 11.0 | 23.2 | 7.4 | 9.0 | 16.1 | 2.0 |
| Cw7 | 13.7 | 13.8 | 25.8 | 33.5 | 31.4 | 19.2 | 19.8 | 13.8 | 29.9 | 15.6 | 17.8 | 14.1 | 2.0 |
| Cw9 | 7.1 | 1.0 | 2.0 | 1.0 | 0.0 | 5.6 | 5.0 | 3.6 | 4.0 | 2.3 | 9.0 | 5.8 | 11.0 |
| Cw10 | 1.7 | 15.1 | 4.4 | 1.0 | 0.0 | 4.0 | 4.2 | 4.4 | 5.0 | 4.1 | 2.6 | 0.5 | 2.9 |
| Cw11 | 0.0 | 0.0 | 0.0 | 0.0 | 0.0 | 0.0 | 0.8 | 0.0 | 0.5 | 0.0 | 0.4 | 0.0 | 0.0 |
| CwX | 3.4 | 1.0 | 0.0 | 2.4 | 3.3 | 1.7 | 0.0 | 0.0 | 5.1 | 1.8 | 0.0 | 0.5 | 2.0 |
| CBL | 40.5 | 29.8 | 27.1 | 0.0 | 11.9 | 25.5 | 21.6 | 36.5 | 9.3 | 34.6 | 28.4 | 9.7 | 15.6 |

*FIG. 3I-1*

| Ethnic | 30 | 30 | 30 | 30 | 30 | 30 | 30 | 30 | 30 | 30 | 30 | 30 | 30 |
|---|---|---|---|---|---|---|---|---|---|---|---|---|---|
| code | 101 | 102 | 103 | 104 | 105 | 106 | 109 | 110 | 111 | 113 | 114 | 115 | 117 |
| *N* ~ | 208 | 141 | 98 | 60 | 64 | 117 | 101 | 96 | 150 | 321 | 295 | 231 | 551 |
| Cw1 | 2.9 | 4.4 | 3.6 | 5.9 | 5.6 | 3.5 | 4.2 | 4.7 | 4.0 | 4.2 | 3.3 | 2.6 | 3.1 |
| Cw2 | 5.5 | 2.5 | 5.6 | 4.3 | 1.6 | 4.3 | 2.0 | 4.8 | 6.9 | 5.2 | 7.2 | 6.5 | 4.0 |
| Cw4 | 14.2 | 9.6 | 14.1 | 8.7 | 11.5 | 11.4 | 7.8 | 13.1 | 9.2 | 11.1 | 11.2 | 16.2 | 17.1 |
| Cw5 | 2.2 | 1.4 | 5.3 | 6.8 | 5.5 | 3.1 | 12.4 | 4.9 | 4.4 | 5.8 | 4.7 | 2.4 | 5.7 |
| Cw6 | 5.4 | 10.2 | 13.1 | 6.1 | 5.6 | 12.1 | 8.8 | 12.9 | 9.9 | 8.9 | 14.2 | 6.7 | 10.1 |
| Cw7 | 18.4 | 19.7 | 38.8 | 24.5 | 28.3 | 25.5 | 35.9 | 24.3 | 20.0 | 20.8 | 28.0 | 15.1 | 22.1 |
| Cw9 | 2.9 | 3.3 | 4.6 | 5.3 | 5.7 | 6.6 | 10.0 | 7.1 | 7.0 | 7.4 | 5.3 | 4.5 | 2.8 |
| Cw10 | 2.9 | 0.7 | 5.3 | 0.8 | 2.4 | 4.5 | 6.6 | 4.2 | 9.6 | 2.7 | 4.8 | 2.6 | 0.7 |
| Cw11 | 0.5 | 0.4 | 0.0 | 0.0 | 0.0 | 0.0 | 0.0 | 0.0 | 0.0 | 0.0 | 0.3 | 0.0 | 0.1 |
| CwX | 0.2 | 2.5 | 0.0 | 0.0 | 1.6 | 1.7 | 0.0 | 0.0 | 0.7 | 3.8 | 1.7 | 0.0 | 1.7 |
| CBL | 45.0 | 45.3 | 9.6 | 37.5 | 32.2 | 27.3 | 12.4 | 24.0 | 28.3 | 30.2 | 19.3 | 43.5 | 32.7 |

FIG. 3I-2

| Ethnic | 30 | 30 | 30 | 30 | 30 | 30 | 30 | 30 | 30 | 30 | 30 | 30 | 30 |
|---|---|---|---|---|---|---|---|---|---|---|---|---|---|
| code | 119 | 120 | 121 | 122 | 124 | 125 | 127 | 128 | 129 | 130 | 131 | 141 | 400 |
| *N* ~ | 50 | 125 | 91 | 97 | 264 | 95 | 83 | 97 | 98 | 98 | 61 | 75 | 99 |
| Cw1 | 2.1 | 1.2 | 5.1 | 3.1 | 3.1 | 3.7 | 1.8 | 11.4 | 3.1 | 3.1 | 5.0 | 0.0 | 5.7 |
| Cw2 | 8.2 | 7.0 | 6.8 | 5.8 | 4.1 | 7.7 | 4.9 | 8.2 | 8.0 | 7.9 | 3.3 | 11.5 | 2.5 |
| Cw4 | 18.1 | 15.7 | 11.7 | 12.1 | 12.8 | 9.3 | 6.1 | 7.3 | 12.7 | 14.3 | 14.5 | 9.7 | 13.4 |
| Cw5 | 1.0 | 4.1 | 1.1 | 22.0 | 9.7 | 3.7 | 6.9 | 2.6 | 6.4 | 3.7 | 3.3 | 4.1 | 0.5 |
| Cw6 | 10.8 | 5.4 | 7.5 | 7.3 | 9.6 | 3.7 | 10.8 | 11.2 | 4.7 | 13.9 | 7.6 | 16.3 | 11.2 |
| Cw7 | 16.6 | 17.0 | 17.8 | 25.9 | 24.3 | 26.3 | 15.5 | 20.6 | 33.2 | 21.1 | 20.2 | 12.9 | 23.7 |
| Cw9 | 6.2 | 5.3 | 2.8 | 0.5 | 4.5 | 5.3 | 3.7 | 17.4 | 3.1 | 5.7 | 9.3 | 2.7 | 2.5 |
| Cw10 | 3.1 | 1.6 | 4.5 | 0.5 | 2.3 | 7.6 | 1.8 | 3.6 | 8.7 | 1.0 | 5.0 | 0.0 | 3.6 |
| Cw11 | 0.0 | 0.0 | 0.0 | 0.0 | 0.0 | 0.0 | 0.0 | 7.1 | 2.1 | 0.5 | 0.0 | 0.0 | 0.5 |
| CwX | 0.0 | 0.0 | 1.1 | 0.5 | 1.5 | 6.1 | 0.0 | 0.0 | 0.0 | 0.0 | 0.0 | 0.0 | 0.5 |
| CBL | 34.0 | 42.8 | 41.7 | 22.2 | 28.1 | 26.5 | 48.4 | 10.7 | 18.1 | 28.8 | 31.7 | 43.0 | 35.7 |

FIG. 3I-3

| Ethnic | 30 | 30 | 30 | 30 | 30 | 30 | 30 | 30 | 40 | 40 | 40 | 40 | 40 |
|---|---|---|---|---|---|---|---|---|---|---|---|---|---|
| code | 401 | 406 | 413 | 601 | 701 | 702 | 801 | 902 | 101 | 104 | 201 | 202 | 204 |
| *N* ~ | 50 | 73 | 50 | 63 | 246 | 197 | 114 | 351 | 1023 | 261 | 145 | 138 | 69 |
| Cw1 | 9.4 | 5.9 | 5.1 | 3.2 | 4.3 | 5.5 | 1.8 | 2.7 | 11.8 | 12.7 | 12.9 | 16.3 | 6.0 |
| Cw2 | 10.4 | 2.1 | 0.0 | 4.8 | 5.4 | 4.4 | 3.1 | 6.4 | 0.1 | 0.8 | 1.4 | 1.1 | 1.4 |
| Cw4 | 11.2 | 19.3 | 9.6 | 12.2 | 9.8 | 10.0 | 19.0 | 16.4 | 4.2 | 5.9 | 4.2 | 8.0 | 3.7 |
| Cw5 | 2.0 | 0.0 | 0.0 | 9.8 | 3.7 | 6.4 | 3.1 | 3.9 | 0.4 | 0.8 | 0.3 | 0.0 | 0.0 |
| Cw6 | 8.0 | 17.8 | 18.9 | 7.6 | 9.5 | 9.4 | 5.4 | 6.6 | 1.0 | 7.5 | 7.3 | 4.4 | 2.2 |
| Cw7 | 16.2 | 24.1 | 19.5 | 27.6 | 21.5 | 28.9 | 22.0 | 22.1 | 15.3 | 12.8 | 6.5 | 16.8 | 22.9 |
| Cw9 | 10.0 | 4.9 | 3.0 | 3.2 | 3.9 | 7.2 | 2.7 | 7.4 | 13.9 | 13.8 | 8.8 | 14.8 | 11.1 |
| Cw10 | 4.1 | 2.8 | 3.1 | 2.4 | 3.9 | 5.7 | 7.7 | 2.8 | 8.8 | 11.0 | 4.9 | 9.0 | 9.0 |
| Cw11 | 9.4 | 0.7 | 0.0 | 0.0 | 0.2 | 0.5 | 0.0 | 0.0 | 4.2 | 3.9 | 2.5 | 3.6 | 19.1 |
| CwX | 0.0 | 0.0 | 0.0 | 5.0 | 3.3 | 5.4 | 0.9 | 1.0 | 0.6 | 0.2 | 0.0 | 0.0 | 0.0 |
| CBL | 19.2 | 22.5 | 40.7 | 24.2 | 34.4 | 16.6 | 34.4 | 30.6 | 39.5 | 30.7 | 51.1 | 26.0 | 24.4 |

| Ethnic | 40 | 40 | 40 | 40 | 4 | 40 | 40 | 40 | 40 | 40 | 40 | 40 | 40 |
|---|---|---|---|---|---|---|---|---|---|---|---|---|---|
| code | 207 | 210 | 211 | 212 | 213 | 216 | 218 | 219 | 220 | 301 | 302 | 303 | 401 |
| *N* ~ | 70 | 60 | 99 | 187 | 73 | 165 | 87 | 79 | 104 | 89 | 138 | 59 | 242 |
| Cw1 | 14.3 | 2.5 | 9.7 | 7.5 | 4.2 | 11.1 | 8.5 | 13.2 | 12.5 | 5.7 | 9.1 | 6.9 | 3.3 |
| Cw2 | 1.4 | 3.4 | 1.5 | 0.8 | 2.1 | 0.6 | 1.2 | 28.9 | 1.4 | 1.7 | 2.9 | 4.3 | 2.7 |
| Cw4 | 0.7 | 9.6 | 16.1 | 4.4 | 6.2 | 7.4 | 5.3 | 14.6 | 5.0 | 11.6 | 4.3 | 8.7 | 3.6 |
| Cw5 | 0.0 | 4.3 | 0.0 | 2.4 | 0.0 | 0.0 | 1.2 | 5.2 | 1.5 | 0.0 | 0.0 | 8.8 | 0.6 |
| Cw6 | 3.6 | 9.7 | 2.5 | 13.3 | 4.2 | 0.0 | 15.8 | 5.9 | 16.4 | 8.8 | 13.6 | 4.3 | 7.2 |
| Cw7 | 15.9 | 7.9 | 16.8 | 15.1 | 15.2 | 21.5 | 5.3 | 10.3 | 13.1 | 8.1 | 17.2 | 5.2 | 25.5 |
| Cw9 | 18.7 | 0.8 | 8.9 | 15.2 | 20.9 | 14.2 | 9.7 | 6.3 | 22.1 | 8.1 | 7.6 | 9.1 | 14.2 |
| Cw10 | 6.6 | 4.2 | 7.9 | 8.4 | 15.3 | 17.2 | 7.3 | 6.1 | 5.4 | 13.0 | 17.1 | 18.6 | 6.9 |
| Cw11 | 5.2 | 1.7 | 2.6 | 3.9 | 0.7 | 1.2 | 2.9 | 2.5 | 2.4 | 3.4 | 1.8 | 0.0 | 13.2 |
| CwX | 0.0 | 0.0 | 0.0 | 0.0 | 0.0 | 1.5 | 0.0 | 0.0 | 0.0 | 0.0 | 0.0 | 0.0 | 0.6 |
| CBL | 33.5 | 55.8 | 34.0 | 29.1 | 31.1 | 25.2 | 43.0 | 7.1 | 20.2 | 39.6 | 26.4 | 34.2 | 22.1 |

FIG. 3I-5

| Ethnic | 40 | 40 | 40 | 40 | 40 | 40 | 40 | 40 | 41 | 41 | 41 | 41 |
|---|---|---|---|---|---|---|---|---|---|---|---|---|
| code | 402 | 403 | 414 | 416 | 421 | 602 | 800 | 803 | 003 | 00A | 102 | 10A |
| *N* ~ | 71 | 149 | 68 | 51 | 73 | 53 | 51 | 56 | 61 | 72 | 156 | 79 |
| Cw1 | 4.3 | 3.4 | 3.7 | 5.0 | 11.8 | 38.7 | 2.9 | 3.6 | 7.5 | 14.9 | 0.6 | 3.2 |
| Cw2 | 0.0 | 0.0 | 0.7 | 4.9 | 2.1 | 0.9 | 1.0 | 10.5 | 2.5 | 0.7 | 12.1 | 9.8 |
| Cw4 | 6.5 | 7.3 | 10.0 | 9.2 | 4.8 | 10.8 | 22.9 | 11.3 | 13.8 | 17.1 | 5.6 | 12.7 |
| Cw5 | 0.0 | 1.0 | 0.0 | 2.0 | 0.0 | 0.0 | 1.0 | 0.0 | 0.0 | 0.0 | 0.3 | 1.3 |
| Cw6 | 6.0 | 6.9 | 0.7 | 4.0 | 6.2 | 9.8 | 2.9 | 7.5 | 0.0 | 11.0 | 1.0 | 14.6 |
| Cw7 | 24.0 | 18.8 | 14.1 | 10.5 | 18.6 | 21.6 | 30.7 | 2.7 | 34.3 | 23.9 | 4.5 | 6.8 |
| Cw9 | 10.3 | 2.0 | 2.2 | 8.1 | 1.5 | 6.2 | 6.3 | 8.5 | 8.4 | 3.5 | 33.1 | 14.8 |
| Cw10 | 19.5 | 8.0 | 0.0 | 2.0 | 34.8 | 4.0 | 13.1 | 10.5 | 4.3 | 7.8 | 19.8 | 16.7 |
| Cw11 | 7.3 | 11.8 | 0.8 | 2.0 | 15.0 | 0.0 | 0.0 | 1.8 | 0.8 | 0.0 | 0.0 | 1.3 |
| CwX | 7.9 | 4.8 | 0.0 | 1.9 | 0.0 | - | - | - | - | - | - | - |
| CBL | 14.2 | 36.0 | 68.5 | 52.4 | 4.0 | 8.1 | 13.3 | 38.0 | 28.4 | 18.1 | 22.6 | 18.9 |

FIG. 3I-6

| Ethnic | 10 | 10 | 10 | 10 | 10 | 10 | 10 | 30 | 30 | 30 | 30 | 30 | 30 |
|---|---|---|---|---|---|---|---|---|---|---|---|---|---|
| code | 100 | 200 | 201 | 204 | 210 | 400 | 600 | 101 | 102 | 103 | 104 | 105 | 106 |
| *N* ~ | 56 | 89 | 54 | 79 | 96 | 318 | 112 | 153 | 105 | 94 | 57 | 55 | 101 |
| DR1 | 6.3 | 2.8 | 0.0 | 9.2 | 4.7 | 6.3 | 8.9 | 5.8 | 8.6 | 10.1 | 10.5 | 10.9 | 10.7 |
| DR3 | 14.0 | 29.2 | 1.9 | 15.3 | 10.4 | 14.7 | 12.4 | 8.5 | 11.7 | 12.2 | 21.9 | 8.2 | 12.4 |
| DR4 | 5.4 | 2.8 | 43.5 | 1.9 | 10.4 | 3.4 | 6.2 | 10.5 | 17.8 | 10.1 | 7.9 | 12.7 | 13.9 |
| DR7 | 10.0 | 6.8 | 7.3 | 7.6 | 14.5 | 9.5 | 8.9 | 10.1 | 7.3 | 13.3 | 28.9 | 12.7 | 20.8 |
| DR8 | 8.9 | 1.1 | 5.6 | 3.8 | 1.9 | 8.3 | 4.0 | 2.0 | 1.0 | 3.2 | 3.5 | 1.8 | 3.7 |
| DR9 | 1.8 | 1.2 | 1.9 | 0.6 | 1.0 | 2.9 | 4.3 | 2.9 | 0.0 | 2.1 | 0.0 | 1.8 | 2.0 |
| DR10 | 0.9 | 1.7 | 0.0 | 3.8 | 2.6 | 1.1 | 4.0 | 0.0 | 1.4 | 0.5 | 0.9 | 0.9 | 1.5 |
| DR11 | 11.6 | 24.7 | 6.3 | 22.7 | 18.2 | 13.5 | 13.2 | 19.1 | 26.4 | 13.8 | 8.8 | 10.0 | 6.4 |
| DR12 | 4.5 | 5.1 | 1.9 | 4.8 | 8.3 | 3.8 | 2.7 | 3.3 | 2.1 | 1.1 | 0.9 | 2.7 | 4.0 |
| DR13 | 14.9 | 14.2 | 24.5 | 12.1 | 7.8 | 13.8 | 12.7 | 10.3 | 7.1 | 11.7 | 5.3 | 15.5 | 9.8 |
| DR14 | 2.9 | 2.8 | 0.0 | 0.0 | 2.1 | 2.4 | 0.9 | 5.6 | 3.3 | 6.4 | 0.9 | 3.6 | 3.2 |
| DR15 | 12.8 | 5.1 | 1.9 | 11.8 | 9.9 | 11.7 | 16.2 | 9.5 | 11.2 | 14.9 | 9.6 | 17.3 | 10.2 |
| DR16 | 1.8 | 0.0 | 0.0 | 0.0 | 2.1 | 2.0 | 3.4 | 6.7 | 0.5 | 0.5 | 0.9 | 1.8 | 0.0 |
| DRJ25 | 0.0 | 0.0 | 0.0 | 0.0 | 0.0 | 0.5 | 0.4 | 0.0 | 0.0 | 0.0 | 0.0 | 0.0 | 0.0 |
| DR2LU | 0.0 | 0.0 | 0.0 | 0.0 | 3.1 | 0.3 | 0.4 | 0.0 | 0.0 | 0.0 | 0.0 | 0.0 | 0.0 |
| DRX | 0.9 | 0.0 | 0.9 | 1.3 | 2.6 | 2.2 | 0.0 | 1.0 | 0.0 | 0.0 | 0.0 | 0.0 | 0.0 |
| DRBL | 3.4 | 2.5 | 4.5 | 5.1 | 0.4 | 3.7 | 1.2 | 4.8 | 1.6 | 0.0 | 0.0 | 0.0 | 1.6 |

FIG. 3J-1

| Ethnic | 30 | 30 | 30 | 30 | 30 | 30 | 30 | 30 | 30 | 30 | 30 | 30 | 30 |
|---|---|---|---|---|---|---|---|---|---|---|---|---|---|
| code | 109 | 110 | 111 | 113 | 114 | 115 | 117 | 120 | 121 | 122 | 124 | 128 | 129 |
| *N* ~ | 101 | 79 | 124 | 285 | 256 | 181 | 507 | 85 | 82 | 76 | 219 | 48 | 100 |
| DR1 | 5.0 | 12.7 | 8.9 | 10.8 | 9.5 | 12.7 | 8.5 | 10.5 | 8.5 | 9.1 | 10.9 | 8.3 | 9.3 |
| DR3 | 11.4 | 7.0 | 8.9 | 11.0 | 10.1 | 8.2 | 10.2 | 10.3 | 11.0 | 26.2 | 11.6 | 10.4 | 11.5 |
| DR4 | 24.8 | 8.2 | 17.2 | 10.8 | 13.4 | 5.2 | 7.1 | 8.2 | 8.7 | 11.8 | 16.0 | 16.4 | 10.3 |
| DR7 | 19.3 | 14.6 | 11.9 | 13.5 | 11.3 | 6.8 | 13.7 | 18.0 | 9.1 | 5.3 | 18.6 | 13.8 | 8.8 |
| DR8 | 2.0 | 5.7 | 3.6 | 5.2 | 4.2 | 4.4 | 3.2 | 5.9 | 1.2 | 1.3 | 3.0 | 7.3 | 4.5 |
| DR9 | 2.5 | 0.6 | 2.0 | 1.4 | 1.0 | 0.0 | 0.1 | 0.0 | 0.6 | 0.7 | 1.8 | 7.9 | 0.5 |
| DR10 | 0.0 | 0.6 | 2.0 | 2.5 | 1.2 | 2.9 | 1.5 | 1.2 | 1.8 | 0.7 | 0.9 | 0.0 | 1.5 |
| DR11 | 7.9 | 17.7 | 6.9 | 9.8 | 18.1 | 27.0 | 26.1 | 9.9 | 13.9 | 14.3 | 11.1 | 13.5 | 15.9 |
| DR12 | 2.0 | 3.2 | 4.0 | 0.4 | 3.9 | 1.9 | 1.1 | 2.4 | 3.7 | 0.7 | 0.9 | 4.2 | 2.0 |
| DR13 | 12.9 | 10.1 | 14.0 | 13.2 | 10.9 | 5.1 | 9.8 | 19.0 | 11.4 | 2.0 | 9.3 | 3.1 | 12.4 |
| DR14 | 1.0 | 2.5 | 3.0 | 3.8 | 3.3 | 3.0 | 2.3 | 0.0 | 2.7 | 3.3 | 2.1 | 3.6 | 2.0 |
| DR15 | 11.4 | 10.1 | 11.6 | 11.2 | 8.8 | 6.3 | 7.4 | 5.7 | 10.0 | 7.7 | 8.4 | 9.0 | 8.3 |
| DR16 | 0.0 | 6.3 | 1.2 | 2.1 | 2.3 | 10.4 | 3.6 | 2.9 | 14.9 | 16.3 | 1.0 | 0.0 | 8.3 |
| DRJ25 | 0.0 | 0.0 | 0.8 | 0.0 | 0.6 | 0.0 | 0.1 | 0.0 | 0.0 | 0.0 | 0.0 | 0.0 | 0.0 |
| DR2LU | 0.0 | 0.0 | 0.8 | 0.0 | 0.2 | 0.0 | 0.0 | 0.0 | 0.0 | 0.0 | 0.0 | 0.0 | 1.0 |
| DRX | 0.0 | 0.6 | 0.8 | 1.2 | 0.6 | 0.0 | 0.5 | 0.0 | 0.0 | 0.0 | 2.1 | 0.0 | 1.0 |
| DRBL | 0.0 | 0.0 | 2.4 | 3.1 | 0.7 | 6.0 | 4.9 | 6.1 | 2.4 | 0.8 | 2.3 | 2.4 | 2.6 |

FIG. 3J-2

| Ethnic | 30 | 30 | 30 | 30 | 30 | 30 | 30 | 40 | 40 | 40 | 40 | 40 | 40 |
|---|---|---|---|---|---|---|---|---|---|---|---|---|---|
| code | 130 | 400 | 601 | 701 | 702 | 801 | 902 | 101 | 104 | 201 | 202 | 212 | 216 |
| *N* ~ | 80 | 93 | 59 | 232 | 146 | 86 | 291 | 898 | 237 | 87 | 79 | 90 | 93 |
| DR1 | 10.9 | 5.6 | 11.4 | 10.1 | 12.0 | 5.2 | 8.5 | 5.5 | 5.1 | 0.6 | 1.3 | 3.3 | 0.0 |
| DR3 | 15.1 | 4.5 | 9.6 | 10.1 | 11.3 | 6.1 | 9.5 | 0.2 | 2.3 | 2.9 | 2.7 | 5.7 | 1.1 |
| DR4 | 10.3 | 10.6 | 22.5 | 12.8 | 18.2 | 16.8 | 11.0 | 22.8 | 21.4 | 14.4 | 15.8 | 9.1 | 8.7 |
| DR7 | 9.9 | 13.3 | 7.4 | 15.1 | 14.4 | 12.4 | 12.2 | 0.4 | 9.2 | 16.3 | 2.0 | 15.2 | 0.0 |
| DR8 | 5.0 | 1.6 | 1.7 | 3.0 | 2.7 | 9.5 | 5.5 | 13.3 | 9.4 | 4.3 | 3.2 | 8.5 | 7.9 |
| DR9 | 0.0 | 1.1 | 0.8 | 1.5 | 2.1 | 0.0 | 1.9 | 13.0 | 8.3 | 12.3 | 15.9 | 7.6 | 6.0 |
| DR10 | 1.3 | 5.6 | 1.7 | 1.7 | 0.7 | 0.6 | 2.1 | 0.6 | 2.1 | 1.2 | 1.9 | 0.6 | 0.0 |
| DR11 | 12.8 | 8.1 | 8.0 | 9.7 | 7.5 | 8.9 | 15.8 | 2.6 | 2.7 | 8.3 | 11.4 | 6.4 | 19.3 |
| DR12 | 3.1 | 1.6 | 3.4 | 1.6 | 0.7 | 1.8 | 3.7 | 7.0 | 7.0 | 7.7 | 13.6 | 7.8 | 23.6 |
| DR13 | 12.2 | 12.3 | 6.2 | 12.7 | 11.6 | 6.7 | 11.5 | 7.8 | 11.8 | 3.0 | 13.2 | 6.8 | 0.5 |
| DR14 | 0.0 | 6.5 | 5.3 | 1.5 | 2.1 | 9.1 | 2.1 | 5.5 | 5.6 | 0.0 | 1.3 | 3.5 | 12.2 |
| DR15 | 7.3 | 25.6 | 14.9 | 10.8 | 14.4 | 8.9 | 8.5 | 17.4 | 11.3 | 19.5 | 9.1 | 16.7 | 7.1 |
| DR16 | 4.7 | 0.0 | 0.8 | 1.3 | 2.1 | 2.9 | 2.8 | 0.8 | 0.2 | 2.4 | 1.3 | 0.0 | 0.0 |
| DRJ25 | 1.3 | 0.0 | 0.0 | 0.0 | 0.0 | 2.3 | 0.7 | 1.9 | 2.1 | 0.6 | 0.0 | 0.6 | 0.5 |
| DR2LU | 0.0 | 0.0 | 0.0 | 0.2 | 0.0 | 0.0 | 0.0 | 0.0 | 0.0 | 0.0 | 0.0 | 0.0 | 0.0 |
| DRX | 0.0 | 0.0 | 0.0 | 5.3 | 0.3 | 0.0 | 0.3 | 0.2 | 0.0 | 0.0 | 0.0 | 0.0 | 0.5 |
| DRBL | 6.1 | 3.6 | 6.2 | 2.5 | 0.0 | 8.6 | 3.8 | 1.0 | 1.5 | 6.6 | 7.4 | 8.3 | 12.4 |

| Ethnic | 40 | 40 | 40 | 40 | 40 | 40 | 40 | 40 | 40 | 40 | 40 | 41 | 41 |
|---|---|---|---|---|---|---|---|---|---|---|---|---|---|
| code | 219 | 220 | 302 | 401 | 402 | 403 | 414 | 416 | 421 | 602 | 803 | 00A | 102 |
| *N* ~ | 72 | 54 | 101 | 238 | 70 | 142 | 61 | 49 | 77 | 51 | 57 | 65 | 145 |
| DR1 | 16.1 | 7.7 | 4.0 | 0.2 | 0.0 | 1.4 | 0.0 | 1.0 | 0.6 | 2.9 | 0.9 | 2.3 | 0.7 |
| DR3 | 21.5 | 8.9 | 9.1 | 4.8 | 7.1 | 4.0 | 0.8 | 5.2 | 5.2 | 2.9 | 0.9 | 2.3 | 3.9 |
| DR4 | 9.0 | 12.4 | 13.4 | 9.0 | 16.4 | 8.7 | 4.1 | 5.2 | 19.5 | 20.0 | 10.9 | 41.7 | 38.3 |
| DR7 | 2.1 | 11.8 | 13.4 | 8.3 | 6.4 | 5.8 | 3.5 | 0.0 | 1.9 | 0.0 | 1.8 | 0.8 | 0.7 |
| DR8 | 2.8 | 4.6 | 7.9 | 4.0 | 4.3 | 6.7 | 6.9 | 3.2 | 6.5 | 9.8 | 7.0 | 4.7 | 3.8 |
| DR9 | 17.0 | 7.4 | 5.9 | 11.9 | 9.3 | 11.5 | 2.5 | 0.0 | 16.9 | 11.3 | 3.5 | 13.7 | 5.3 |
| DR10 | 1.4 | 2.9 | 2.0 | 2.5 | 2.1 | 5.7 | 0.0 | 1.0 | 1.3 | 0.0 | 0.9 | 0.0 | 0.0 |
| DR11 | 8.1 | 12.9 | 8.0 | 4.2 | 6.4 | 2.1 | 3.5 | 12.3 | 13.6 | 9.8 | 0.0 | 12.1 | 11.2 |
| DR12 | 2.1 | 2.8 | 8.4 | 13.7 | 12.1 | 29.7 | 49.7 | 7.5 | 13.6 | 21.2 | 1.8 | 0.8 | 0.7 |
| DR13 | 2.1 | 5.8 | 5.4 | 3.6 | 5.7 | 4.2 | 3.3 | 3.1 | 1.3 | 1.0 | 4.4 | 4.6 | 7.5 |
| DR14 | 3.5 | 0.9 | 2.0 | 7.1 | 6.4 | 5.6 | 0.8 | 3.1 | 3.2 | 9.8 | 60.2 | 1.5 | 10.8 |
| DR15 | 4.3 | 11.5 | 13.0 | 20.6 | 17.1 | 9.5 | 20.6 | 42.0 | 9.7 | 9.6 | 4.9 | 2.3 | 1.4 |
| DR16 | 2.9 | 0.0 | 2.8 | 4.5 | 2.9 | 2.1 | 0.0 | 0.0 | 3.2 | 0.0 | 0.0 | 0.8 | 1.4 |
| DRJ25 | 0.0 | 0.0 | 1.5 | 0.2 | 0.0 | 0.4 | 0.0 | 0.0 | 0.0 | 0.0 | 0.9 | 0.8 | 5.2 |
| DR2LU | 0.0 | 0.0 | 0.0 | 1.7 | 2.1 | 0.0 | 0.0 | 0.0 | 3.2 | 0.0 | 0.0 | 0.0 | 0.3 |
| DRX | 0.0 | 0.0 | 0.0 | 0.2 | 1.4 | 0.4 | 0.0 | 0.0 | 0.0 | 0.0 | 0.0 | 0.0 | 0.3 |
| DRBL | 7.1 | 10.6 | 3.3 | 3.4 | 0.1 | 2.1 | 4.2 | 16.2 | 0.0 | 1.6 | 2.1 | 11.5 | 8.4 |

FIG. 3J-4

| Ethnic | 10 | 10 | 10 | 10 | 10 | 10 | 10 | 30 | 30 | 30 | 30 | 30 |
|---|---|---|---|---|---|---|---|---|---|---|---|---|
| code | 100 | 200 | 201 | 204 | 210 | 400 | 600 | 101 | 102 | 103 | 104 | 105 |
| *N* ~ | 56 | 89 | 54 | 79 | 96 | 318 | 112 | 153 | 105 | 94 | 57 | 55 |
| DQ1 | 50.9 | 42.7 | 31.3 | 59.1 | 40.8 | 45.1 | 47.8 | 40.9 | 31.5 | 39.9 | 28.9 | 49.2 |
| DQ2 | 21.4 | 16.9 | 10.2 | 15.5 | 19.3 | 19.8 | 17.1 | 16.8 | 16.7 | 19.7 | 50.0 | 16.1 |
| DQ3 | 2.7 | 1.7 | 28.3 | 3.8 | 6.9 | 5.0 | 4.4 | 5.2 | 8.3 | 7.2 | 9.6 | 11.6 |
| DQ4 | 5.4 | 22.5 | 5.8 | 7.3 | 4.7 | 10.0 | 5.8 | 2.3 | 1.0 | 5.2 | 4.4 | 2.7 |
| DQ7 | 19.6 | 16.3 | 15.0 | 11.6 | 25.5 | 18.6 | 18.3 | 29.6 | 38.2 | 24.6 | 7.0 | 18.8 |
| DQX | 0.0 | 0.0 | 0.0 | 0.0 | 0.5 | 0.0 | 0.0 | 0.0 | 0.0 | 0.0 | 0.0 | 0.0 |
| DQBL | 0.0 | 0.0 | 9.4 | 2.7 | 2.4 | 1.5 | 6.5 | 5.3 | 4.2 | 3.4 | 0.0 | 1.6 |

| Ethnic | 30 | 30 | 30 | 30 | 30 | 30 | 30 | 30 | 30 | 30 | 30 | 30 |
|---|---|---|---|---|---|---|---|---|---|---|---|---|
| code | 106 | 109 | 110 | 111 | 113 | 114 | 115 | 117 | 120 | 121 | 122 | 124 |
| *N* ~ | 101 | 101 | 79 | 124 | 285 | 256 | 181 | 507 | 85 | 82 | 76 | 219 |
| DQ1 | 36.9 | 28.7 | 40.8 | 43.9 | 45.9 | 36.3 | 45.5 | 35.4 | 43.0 | 50.6 | 38.0 | 34.3 |
| DQ2 | 26.2 | 25.7 | 16.3 | 16.8 | 21.4 | 19.1 | 14.3 | 22.0 | 20.2 | 19.5 | 27.3 | 25.4 |
| DQ3 | 11.0 | 20.8 | 9.1 | 11.4 | 10.0 | 11.1 | 10.1 | 7.3 | 7.6 | 9.8 | 12.9 | 13.9 |
| DQ4 | 3.1 | 2.0 | 4.4 | 4.8 | 4.5 | 6.1 | 3.9 | 2.3 | 6.6 | 0.6 | 0.7 | 3.9 |
| DQ7 | 19.4 | 22.8 | 23.9 | 21.0 | 16.2 | 27.3 | 19.9 | 29.1 | 14.4 | 19.5 | 15.4 | 19.0 |
| DQX | 0.0 | 0.0 | 0.0 | 0.0 | 0.0 | 0.0 | 0.0 | 0.0 | 0.0 | 0.0 | 0.0 | 0.2 |
| DQBL | 3.2 | 0.0 | 5.5 | 2.2 | 2.1 | 0.0 | 6.2 | 3.9 | 8.2 | 0.0 | 5.7 | 3.4 |

FIG. 3K-1

| Ethnic | 30 | 30 | 30 | 30 | 30 | 30 | 30 | 30 | 30 | 40 | 40 | 40 |
|---|---|---|---|---|---|---|---|---|---|---|---|---|
| code | 128 | 129 | 130 | 400 | 601 | 701 | 702 | 801 | 902 | 101 | 104 | 201 |
| *N* ~ | 48 | 100 | 80 | 93 | 59 | 232 | 146 | 86 | 291 | 896 | 237 | 87 |
| DQ1 | 32.1 | 44.5 | 35.9 | 56.1 | 37.8 | 43.7 | 41.5 | 26.6 | 38.1 | 45.6 | 40.6 | 35.3 |
| DQ2 | 17.5 | 19.0 | 22.6 | 13.2 | 14.4 | 22.9 | 21.8 | 16.7 | 18.2 | 0.6 | 10.2 | 12.6 |
| DQ3 | 2.1 | 11.5 | 8.8 | 13.4 | 15.9 | 12.1 | 11.6 | 11.8 | 7.1 | 18.8 | 17.0 | 9.2 |
| DQ4 | 5.5 | 4.0 | 2.5 | 1.6 | 3.4 | 2.4 | 3.1 | 7.7 | 6.6 | 14.9 | 8.3 | 4.1 |
| DQ7 | 36.7 | 21.0 | 17.4 | 12.0 | 21.8 | 16.3 | 21.4 | 25.1 | 24.3 | 15.2 | 15.8 | 19.6 |
| DQX | 0.0 | 0.0 | 0.0 | 0.0 | 0.0 | 0.0 | 0.0 | 0.0 | 0.0 | 0.1 | 0.0 | 0.0 |
| DQBL | 6.2 | 0.0 | 12.8 | 3.7 | 6.7 | 2.7 | 0.6 | 12.2 | 5.7 | 4.8 | 8.1 | 19.3 |

| Ethnic | 40 | 40 | 40 | 40 | 40 | 40 | 40 | 40 | 40 | 40 | 40 | 40 |
|---|---|---|---|---|---|---|---|---|---|---|---|---|
| code | 202 | 212 | 216 | 219 | 220 | 302 | 401 | 402 | 403 | 414 | 416 | 421 |
| *N* ~ | 79 | 90 | 93 | 72 | 54 | 101 | 238 | 70 | 142 | 61 | 49 | 77 |
| DQ1 | 39.4 | 34.4 | 33.5 | 39.2 | 31.1 | 36.3 | 48.4 | 37.6 | 33.7 | 33.5 | 59.0 | 26.6 |
| DQ2 | 5.4 | 17.2 | 1.1 | 16.6 | 14.0 | 20.8 | 11.5 | 10.0 | 9.8 | 4.9 | 11.1 | 8.4 |
| DQ3 | 8.2 | 11.1 | 1.6 | 21.4 | 12.4 | 2.5 | 18.6 | 22.9 | 16.9 | 9.8 | 6.1 | 27.3 |
| DQ4 | 6.3 | 3.3 | 1.6 | 5.6 | 3.7 | 1.5 | 3.7 | 4.6 | 4.2 | 9.8 | 2.0 | 7.1 |
| DQ7 | 37.8 | 19.4 | 48.2 | 8.6 | 27.2 | 25.7 | 17.0 | 21.2 | 35.1 | 41.8 | 21.4 | 30.5 |
| DQX | 0.0 | 0.0 | 0.5 | 0.0 | 0.0 | 0.0 | 0.0 | 0.0 | 0.0 | 0.0 | 0.0 | 0.0 |
| DQBL | 2.9 | 14.5 | 13.4 | 8.6 | 11.5 | 13.3 | 0.8 | 3.7 | 0.3 | 0.2 | 0.3 | 0.0 |

*FIG. 3K-2*

| Ethnic | 40 | 40 | 41 | 41 |
|---|---|---|---|---|
| code | 602 | 803 | 00A | 102 |
| *N* ~ | 51 | 57 | 65 | 145 |
| DQ1 | 31.8 | 11.0 | 6.6 | 13.4 |
| DQ2 | 4.9 | 1.8 | 3.1 | 1.7 |
| DQ3 | 20.2 | 6.0 | 31.8 | 5.3 |
| DQ4 | 10.8 | 8.8 | 12.0 | 5.7 |
| DQ7 | 30.9 | 67.9 | 31.7 | 70.4 |
| DQX | 0.0 | 0.0 | 0.0 | 0.0 |
| DQBL | 1.4 | 4.6 | 14.9 | 3.5 |

*FIG. 3K-3*

PLURIPOTENT VACCINE AGAINST ENVELOPED VIRUSES

BACKGROUND OF THE INVENTION

I. Field of the Invention

The field of the invention relates to compositions and methods for the induction of immune responses against enveloped virus in mammals. In particular embodiments, the invention relates to vaccines comprising major and minor histocompatibility complex antigens, blood group antigens and other cell surface antigens exhibiting significant genetic polymorphism in mammalian populations, which may be picked up by enveloped viruses as they bud from the cell membrane and may therefore serve as a target for an immune attack.

II. Description of the Related Art

A. Enveloped Viruses

Eukaryotic viruses are a large and diverse group of infectious agents primarily known for the diseases they cause. These agents can be classified by a number of criteria including genome structure, mode of replication and host specificity. Another manner of grouping eukaryotic viruses is by the structure of the viral particle. "Non-enveloped" viral particles are made up of a proteinaceous capsid that surrounds and protects the viral genome. The capsid is formed by viral structural products encoded by the virus genome and synthesized within the host cell. "Enveloped" viruses also have a capsid structure surrounding the genetic material of the virus but, in addition, have a lipid bilayer "envelope" that surrounds the capsid. The envelope is acquired as the capsid buds through one of the host cell membranes—usually the plasma membrane but sometimes from the nuclear membrane, the Golgi apparatus or endoplasmic reticulum.

Exemplary enveloped virus families include Togaviridae, Flaviviridae, Coronaviridae, Rhabdoviridae, Filoviridae, Parantyxoviridae, Orthontyxoviridae, Bunyaviridae, Arenaviridae, Retroviridae, Herpesviridae, Poxviridae and Iridoviridae. These viruses and others are responsible for such diseases as encephalitis, intestinal infections, immunosuppressive disease, respiratory disease, hepatitis and pox infections.

The make-up of an enveloped virus membrane varies depending on the location in the host cells from which the virus acquired its envelope. In general, the envelope comprises a bilayer of lipids completely surrounding the virus capsid or nucleoprotein. In addition to various lipids, the envelope contains integral and transmembrane proteins. Many transmembrane proteins have sugar residues attached and are referred to as glycoproteins. Virally-encoded transmembrane proteins play important roles in the infectious process by acting as targeting ligands, as enzymes and as membrane fusion activators. Because host cells also express many membrane-bound proteins, it is possible for enveloped virus particles to contain host cell proteins as well as those that are virally-encoded. In some instances, the virus may pick up genes of normal cellular components from the host cell which are useful to its propagation in other hosts.

Considerable efforts have been expended toward the development of suitable vaccines designed to protect against infection by disease-causing enveloped viruses. Though some vaccines have proved successful, many others have failed to live up to expectations. Vaccine failures often are attributed to one or more of the following:

1. Enveloped viruses have a notorious reputation for a phenomenon called "antigenic drift." When antigenic drift occurs, viral antigens mutate and their antigenic profile is altered. If the drift is extensive enough, the immune response generated against the original antigenic profile is no longer able to recognize the mutated forms and, therefore, escape the protective immune mechanisms within the immunized host.
2. Another type of "variation" problem relates to viruses having multiple strains, such as rhinovirus, which may have more than 50 different antigenic strains. Therefore, it is impractical to develop vaccines against all of these viral strains. Yet another example of antigenic variation is exhibited by influenza viruses, which frequently have seasonal variations in the prevailing strains. Thus, it is necessary to redesign particular influenza vaccines on an annual basis, depending upon the prevalent strain of influenza virus that is infecting the population that particular year.
3. Unfortunately, cell mediated immunity or humoral antibody induced against virus-related envelope or nuclear protein antigens may be short-lived. As a result, most current vaccines are capable of inducing immunity only for a short time following immunization. Thus, to achieve ongoing protection, it often is necessary to immunize repeatedly, especially where the antigen is the inactivated virus or a subunit vaccine.
4. A problem with many viral vaccines is the cost-benefit analysis of choosing a "live" versus a "killed" vaccine. In general, immunization with live, attenuated viruses results in a much stronger immune response than with killed virus. In some instances, such as protection against smallpox maybe life long after immunization with live cowpox virus which induces cross reactive immunity to smallpox. While the mechanism behind this phenomena is not fully understood, it is likely that limited replication of attenuated viruses provides a more potent set of antigens with which to stimulate the immune system. Unfortunately, virus strains with sufficient attenuation levels are difficult to produce. In addition, one always runs a risk that the attenuated virus will revert to a pathogenic form following immunization, thereby causing full-blown infection and disease.

Because of many problems outlined above with respect to viral vaccines, effective vaccines have been developed against only a small minority of the many viruses that are capable of infecting the human population. Efforts have been directed primarily against viral vaccines causing potentially fatal illness, such as smallpox. Consequently, there are but a small number of effective vaccines developed against the large number of enveloped viruses which create diseases in humans and other mammals. Although there have been a few successes, such as vaccines against smallpox, measles, mumps, feline leukemia virus and canine distemper virus, humans and other mammal species remain largely unprotected against the vast majority of enveloped viruses.

B. HIV and MHC Antigens

Because of the devastating consequences of infection, and the rapidly growing number of infected individuals, there have been intense efforts directed at producing a vaccine against human immunodeficiency virus (HIV) infection. Because of the danger in using live retroviruses, these vaccines primarily have involved the use of viral subunits, such as the surface glycoprotein gp120/160, and antibodies thereto. For the most part, the results have been disappointing.

A variety of unique problems are presented when working with HIV vaccines. For example, the antigenic drift seen in HIV antigens virtually is unparalleled in other systems. In addition, the putative identification of the CD4 molecule as a receptor, while constituting a major step towards understanding the virus life cycle, has proved to be a problematic complication. Interactions between host molecules and CD4, as well as those between host molecules and gp120/160, appear to hinder the effects of anti-gp120/160-based vaccines.

Another disadvantages in using specific immunization against HIV is that one of the primary methods for detecting infection is by the presence of serological reactivity with HIV in the serum of the individuals, indicating that infection with HIV has occurred. Consequently, immunization with HIV or antigenic subunits thereof will induce similar antibodies, making it difficult to differentiate infection from protection.

One area of research that has developed in response to these and other problems involves the use of major histocompatibility (MHC) antigens. The general principle behind this work is that an infecting HIV particle, either as free enveloped virus or as virally-infected cells, will be associated with MHC antigens that are potentially distinct from those of the recipient. The literature as a whole is, at best, confused with respect to how such an immune response might function if, in fact, it would function at all.

For example, Clerici et al. (1990) discuss the use of alloantigen immunization to bolster the flagging T-helper functions in HIV patients. Clerici, as had others, observed that despite the inability of the T cells of AIDS patients to "recall" antigens, these cells remained responsive to alloantigens. Clerici found that when the alloantigen response was still present, T cells of $HIV^+$ individuals could be "taught" to recall influenza antigens when primed with influenza antigen in combination with alloantigen and challenged with influenza antigen alone. The ability of alloantigen alone to encourage recall of influenza antigen by T cells in AIDS patients was negligible, suggesting a contribution by the influenza antigen in the role of both a stimuli and a target.

Another study that looked at the effects of cellular antigens (xenoantigens) on responses to immunodeficiency viruses was reported by Stott (1991). Stott and his colleagues observed that macaques immunized with uninfected human cells were resistant to infection by simian immunodeficiency virus (SIV) grown in those cells. Macaques were not resistant to infection by SIV grown in simian cells. When the challenge virus was HIV, the immunized macaques were not resistant, suggesting some correlation of protection with the nature of the viral antigen. Stott also identified the anti-MHC response as directed against Class II determinants in the human cells but it is unclear whether these were species specific or xenogenic antigenic determinants of class II picked up by the viruses grown in human cells or truly cross-reactive allotypic antigens also present in the monkey.

Kion and Hoffman (1991) demonstrated a similar phenomenon in alloimmunized mice. When immunized with cells from another murine strain, mice made antibodies against gp120 and p24 of HIV. In addition, an autoimmune mouse strain made antibodies against gp120. In both autoimmune and autoimmune mice, antibodies against anti-MHC antibodies (MHC-image) were found. The authors concluded that the presence of both these kinds of antibodies "supports the idea of synergy between immune response to allogeneic cells and HIV antigenic stimuli."

Langlois et al. (1992), using SIV grown in human cells, were able to elicit responses against human cellular determinants in macaques. Cranage et al. (1992) also reported that human-specific responses develop when macaques are immunized with SIV grown in human cells. While initially reporting that the predominant response was against class I antigens, later studies were able to find no correlation between class I titers and protection. Cranage et al. (1993) reported that macaques vaccinated with SIV grown in human cells generate a class II-specific response not seen in control animals. Interestingly, infected macaques were shown to have antibodies specific for rhesus MHC, raising the possibility that SIV mimics rhesus MHC or alters macaque recognition of self-MHC.

Kiprov et al. (1994) took advantage of their earlier, unrelated studies on alloimmunization to look at anti-cellular/anti-HIV response. A group of women previously had been immunized with peripheral blood lymphocytes from their husbands in an effort to prevent spontaneous abortion. Twelve out of fourteen women immunized developed antilymphocyte antibodies (ALAs). Of these, two were found to neutralize HIV-1 in vitro in a complement dependent manner, one patient to a relatively high titer. Because addition of anti-HIV sera resulted in additive neutralization, Kiprov suggested that the test sera was directed to nonviral target antigens. The authors could not explain the absence of neutralizing activity from the other ALA+subjects, however, and the mechanism for high titers of neutralizing antibodies in the one patient remains unexplained since subsequently it has been shown not to be related to MHC class I or II antigens.

Thus, it remains unclear whether MHC stimulates the immune system in a non-specific manner, or specifically increases immune responses against viral targets. It also is unclear whether xeno or alloimmune effects on SIV/HIV are, in any way, attributable to the MHC-like character of gp120 and thus limited by the particular viral antigen. Thus, despite considerable speculation and some interesting results with an SIV model, the role played by alloimmunity in antiviral defense remains unclear.

For all the above reasons, there is a great need for more efficient viral vaccines against enveloped viruses. When one considers all of the possible antigenic strains and frequency of antigenic drift of various viruses which may affect various mammalian species, it is impractical with present methodology to comprehend a universal viral vaccine which has as it target the viral antigens themselves. On the other hand, a vaccine which has as its target cellular membrane antigens which are expressed by genes controlling genetic diversity in the animal species could be pluripotent. The enveloped viruses must pick up genetically controlled antigens from the cell membrane as they bud from the host cell which provide a much more stable and practical target for the induction of protective immunity against membrane viruses. The alloantigens which the enveloped viruses pick up when they bud from the host cell membrane provide a potential target in the development of a pluripotent viral vaccine protective against the majority of these viruses.

III. SUMMARY OF THE INVENTION

It is, therefore, an object of the present invention to provide a composition suitable for administration to a subject that induces protective immunity to infection by an enveloped virus.

It is another object of the present invention to provide a composition suitable for administration to a subject that induces protective immunity to infection by human immunodeficiency virus.

It is yet another object of the present invention to provide a method of immunizing a subject with a composition that induces protective immunity to infection by an enveloped virus such as rhinoviruses or influenza viruses.

It is still yet another object of the present invention to provide a method of immunizing a subject with a composition that induces protective immunity to infection by human immunodeficiency virus.

In satisfying these objectives, there is provided a composition comprising intact cells, wherein said cells express major histocompatibility antigens with at least four common allotypes from a given mammalian species.

There also is provided a composition wherein said allotypes each are present in 80% or more of individuals. There further is provided composition wherein any given cell expresses only a single allotype.

In another embodiment, there is provided a composition wherein at least one cell expresses at least two allotypes. There also is provided a composition wherein said antigens are Class I antigens, and there is provided a composition wherein said antigens are Class II antigens.

In yet another embodiment, there is provided a composition wherein said antigens are both Class I and Class II antigens or other alloantigens coded by polymorphic genes. There further is provided a composition wherein said plurality is representative of all known allotypes of said mammalian species. Further embodiments include a composition further comprising at least one recombinant major or minor allotypic antigen for the mammalian species. And in yet a further embodiment, there is provided a composition this recombinant antigen is produced in a host selected from the group consisting of bacteria, fungi, insect cells and mammalian cells.

In a further embodiment the allotypes of the composition include at least one of the following human allotypes:

HLAA$_1$, A$_2$, A$_3$, A$_{11}$, A$_{24}$, A$_{29}$, A$_{32}$,
B$_7$, B$_8$, B$_{13}$, B$_{35}$, B$_{38}$, B$_{44}$, B$_{55}$, B$_{60}$, B$_{62}$,
CW$_1$, CW$_2$, CW$_4$, CW$_5$, CW$_6$, CW$_7$, CW$_9$, CW$_{10}$, CW$_{11}$,
DR$_1$, DR$_3$, DR$_4$, DR$_7$, DR$_8$, DR$_{11}$, DR$_{12}$, DR$_{13}$, DR$_{15}$,
ABO Blood Groups.

In still yet another embodiment, there is provided a composition wherein said cells further express an antigen from an enveloped virus. In further embodiments, the virus is a herpesvirus and/or a retrovirus. And in still yet further embodiments, the composition comprises intact cells further express a cytokine. The cytokine can be IL-1, IL-2, IL-4, IL-7, IL-12, γ-interferon or GMCSF. Other embodiments provide intact cells further expressing a costimulatory molecule. The costimulatory molecule may be B-7.

In another embodiment, the cells of the composition are rendered incapable of growth; this may be accomplished by lethal irradiation. The composition further may comprise a pharmaceutically acceptable carrier, diluent or excipient.

In an alternative embodiment, there is provided a method for generating an immune response in a given mammal comprising:

(a) providing a composition comprising
  (i) intact cells, wherein said cells express major histocompatibility antigens with at least four allotypes from the species of said given mammal; and
  (ii) a pharmaceutically acceptable carrier, diluent or excipient,
(b) administering said composition to said given mammal.

In another alternative embodiment, there is provided a method for eliciting an immune response in a given mammal against an enveloped virus comprising:

(a) identifying a given mammal at risk of infection with said virus;
(b) providing a composition comprising
  (i) intact cells, wherein said cells express major histocompatibility antigens with a plurality of allotypes from the species of said given mammal;
  (ii) a pharmaceutically acceptable carrier, diluent or excipient,
(b) administering said composition to said given mammal in an amount effective to elicit said immune response.

In still yet another alternative embodiment, there is provided a composition comprising intact, non-malignant cells, wherein said cells express major histocompatibility antigens with a plurality of allotypes from a given mammalian species.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

IV. BRIEF DESCRIPTION OF THE DRAWINGS

FIG. 1,2, and 3A–K provide a list of HLA allotypes and their frequency of distribution by ethnic groups.

V. DETAILED DESCRIPTION OF THE INVENTION

For every cell that is present in a mammal, that mammal must determine whether that cell is "self" or "non-self." If "self," the mammal does not want to mount an immune response. If non-self, the mammal (host, in this case) usually wants to respond and eliminate the cell. A host further distinguishes two subsets of non-self cells—cells that the host has seen previously and cells that are new to the host. Biological mechanisms have evolved that permit a rapid and more substantial response to cells that previously have been encountered by the host.

Thus, when a virus or virally-infected cell is exposed to a host for the first time, it is unlikely that a significant immune response will be mounted against the infectious agent before infection of host cells occurs. In contrast, a host immune system that has been "primed," i.e., made sensitive to a particular virus or viral antigen, can mount a rapid and significant immune response that will prevent or limit infection. This is the rationale behind vaccines, which are designed to sensitize the immune system of the host to one or more antigens of a given virus. The following is a detailed explanation of the immune response as it applies to the instant invention.

A. Humanity to Viruses Via Recognition of Antigen and Alloantigen by Antibody and by T Cells Major and minor histocompatibility complex (MHC) glycoproteins were studied intensively for many years without investigators having a good understanding of their function. These cell-surface antigens, exhibiting a high degree of genetic polymorphism in human and other mammalian populations, were subject to analysis using alloantibodies raised by tissue immunizations between individuals of the same species. Since they also were major targets for specific immunological rejection of transplanted tissues and organs and, in the absence of a specified function, they were called "transplantation antigens."

Transplant rejection involves the recipient's T lymphocytes (T cells) and B lymphocytes (B cells) responding to antigenic determinants caused by structural differences in the MHC molecules of the donor and recipient. Such determinants are called alloantigenic determinants, or "allodeterminants," and the responding T cells are termed "alloreactive." In the 1970's, cellular immunologists discovered the physiologic function of MHC molecules, showing that they were instrumental in stimulating T cell responses to all antigens, not just alloantigens. Continuing study through the 1980's provided a mechanistic understanding of this relationship facilitated by the discovery that α/β and γ/δ T cell receptors, unlike B cell receptors (immunoglobulins), do not recognize native proteins but, rather, require that they be unfolded and broken down into small fragments. This antigen "processing" takes place within cells and, as far as is known, exploits enzymes and intracellular compartments that are, in general, used for the transport, turnover, maturation and processing of normal cellular proteins.

Thus, the role of MHC molecules is threefold: (1) to bind peptides within the cell; (2) to transport them to the plasma membrane; and (3) to retain them at the cell surface in a complex which can interact with the receptors of the T lymphocytes. The ligand recognized by a T cell receptor is thus a complex of a peptide, usually 8–25 amino acids in size, bound to an MHC molecule. The MHC glycoproteins are said to "present" the peptide to the T cell and are aptly described as "antigen-presenting" molecules. Townsend and Bodmer, *Ann. Rev. Immunol.* 7:601–624 (1989).

Two types of protein antigens can be presented by healthy mammalian cells—those within the cell (e.g., viral proteins made after viral infection of the cell) and those made elsewhere which then enter the cell by endocytosis (e.g., bacterial toxins). Two homologous classes of MHC molecules have evolved as specialized with regard to intracellular movement and antigen presentation. Class I MHC molecules primarily present peptides derived from endogenously made proteins such as those induced by intracellular viral infection, while class II MHC molecules specialize in the presentation of peptides derived from endocytosed antigens. Although this is the most common situation, there can be exceptions in which the conditions of antigen presentation by MHC molecules are reversed.

Two types of T cells are thought to interact with the two classes of MHC molecules. CD4 lymphocytes are helper T cells thought to receive instructions from the MHC class II antigen, which presents processed antigen peptides in the MHC class II grove. On the other hand, CD8 lymphocytes (cytotoxic T cells) recognize antigenic peptides bound to MHC class I antigens. Antigen processing also occurs in B cells, which can endocytose and fragment the antibody/antigen complex. This complex is formed when the antigen reacts with B cell receptor, membrane-bound immunoglobulin antibody directed against the antigen. In addition, macrophages can endocytose antigen-antibody complexes via $F_c$ receptors, leading to enhanced processing and presentation to T cells. It is important to emphasize that in order for the T cell to recognize an antigen presented by either a class I or class II MHC molecule, there must be a direct HLA match between the lymphocyte and the cell presenting the antigen or there must be recognition of a cross reacting epitope on the MHC molecule by the T cell receptors of the T cell. Thus, a cytotoxic T cell of MHC class I A2 usually cannot recognize and kill a cell bearing the same antigen which has been processed and presented by MHC class I A1 human cells.

It is important to emphasize that the two arms of the immune system (humoral and cell-mediated) recognize antigen in different forms. Antibody, produced by B cells, recognizes predominantly conformational epitopes on the surface of large antigen molecules. T cells, via their antigenic specific receptor, recognize linear sequences of peptides produced by processing of antigens by enzymatic breakdown of the native protein. Thus, most T cell epitopes are not recognized in proteins in their natural state and must be actively created, either during protein synthesis (i.e., before the molecule has folded into its correct final shape) or by a reductive enzymatic process that involves some form of protein degradation. T cell epitopes are therefore generally independent of the native conformation (secondary and tertiary structure) and, thus, their recognition invariably has less discriminatory power than B cell epitopes which depend upon surface conformational structures. However, antigen processing exposes the immune system to a set of structures that are normally buried within the native confirmation of macromolecules and, therefore, would otherwise be invisible to immune recognition. This double ability to recognize both internal structure by T cell receptors and external configuration by B cell antibodies is integrated into the overall protective scheme of the immune system.

The second major difference between the two arms of the adaptive immune system is that T cell recognition does not occur with antigen alone. The two molecules, T cell receptor and epitope, only interact on the surface of a separate cell, the antigen processing cell. Further, this cell is required to express a third molecule, either class I or class II, of the major histocompatibility complex glycoprotein. These cell-surface glycoproteins have been shown to directly bind T cell epitopes. This binding step is the essential screening process by which appropriately processed antigen is selected from the unprocessed majority. The majority of evidence suggests that correct T cell recognition can only occur if the appropriate antigen epitope is positioned within a relatively small molecular groove at the distal end of a MHC molecule.

Thus, the molecular and cellular mechanisms by which T cell epitopes are created from complex macromolecules, and are then expressed by antigen presenting cells in a form that can be recognized together, constitute antigen processing. Antigen presentation is defined as the subsequent interaction between antigen presenting cell and T cell in the presence of peptide antigen. Therefore, antigen processing is a crucial step in the overall series of events leading to T cell stimulation and, hence, in the development of an effective immunological response.

B. Two Pathways of Antigen Processing

The presence of two separate classes of MHC molecules on the surface of cells has long been known. This class division is related to the separation of mature T lymphocytes into two distinct groups. The mutually exclusive T cell surface antigens CD8 and CD4 provide specificity for MHC classes I and II, respectively. In contrast, it has been shown that antigen- specific T cell receptors use the same pool of germline elements for recognition of antigen bound to both classes of MHC. The class I-associated antigens are derived predominantly from internal antigens (such as viral antigens) synthesized endogenously by the antigen processing cells, while class II-associated antigens typically are external, acquired exogenously by endocytosis from the extracellular environment. MHC class I antigens can be expressed in all nucleated cells. Therefore, via the class I processing pathway, the immune system can recognize and react to a whole array of intracellular antigens that, in their native state, may never be exposed to the extracellular environment. This is consistent with the function of CD8+T cells, to scan all cells in the body for viral antigens that may be presented with MHC class I molecules, thereby protecting the host from intracellular viral infection. MHC class II antigens are found mainly on specialized cells within the immune system, in particular B cells, macrophages, and dendritic cells. See *Critical Reviews in Biochemistry and Molecular Biology*, 26:439–473 (1991) by T. P. Levine and B. M. Chain, "The Cell Biology of Antigen Processing."

C. Viral Infection and Implications for Immunity Against Enveloped Viruses

A viral protein antigen thus may be broken down into different peptides which are presented as distinct peptide sequences in the groove of different MHC molecules, depending upon the genetics of host's MHC allele expression. Processing and presentation are key steps in the development of an effective immune response.

Transmission of envelope viruses may occur by infection with the free viral particle itself, such as occurs by aerosol transmission of respiratory viruses like rhinoviruses or influenza virus due to coughing or sneezing by affected individuals. In addition, transmission can occur by transfer of infected cells, such as transfer of HIV-infected lymphocytes via the semen. These cells may carry the HIV viral genome, yet little or no free virus may be present at the moment of transmission. Although viral related peptide T cell epitopes may be expressed by the MHC class I molecules on the surface of the infected cell, these viral peptides cannot be recognized by the T cell receptors of a recipient host unless there happens to be an allotype match between the MHC class I or II of the donor and recipient. Thus, even though the recipient may already have ongoing long-term T cell memory against peptides associated with the infecting virus, this memory will be ineffective against the peptide sequences presented by the MHC glycoprotein molecules on the incoming cell surface or viral membrane because they cannot be recognized by the host T cells given the MHC mismatch.

The foreign protein viral antigens may be picked up by MHC class II antigen presenting cells of the host and presented to the CD4 helper cells. In addition, once the virus gains entry into the host's cells and begins to replicate and synthesize proteins, the new host's MHC antigens will present these different peptide sequences to cytotoxic T cells, which then act to inhibit further viral proliferation by killing the viral infected cells in the new host. This type of specific viral immunity does not, however, prevent transmission of infection either by free viral particles or infected cells, although it may limit the degree of viral replication in the new host.

On the other hand, preexisting antibody directed against antigens on the surface of the viral particle may react directly with the viral particle and prevent the initial infection. It is our hypothesis that the presence of preexisting allotypic antibody or T cell immunity against the predominant HLA antigens may trigger an immediate recognition of the foreign alloantigens present on the enveloped lipid membrane of the invading virus which, in turn, may trigger an immediate recognition and attack of the foreign virus if the level of immunity is sufficiently high. If low level immunity is present, it may trigger recognition of the foreign alloantigen which would lead to cytokine release, accelerated specific antigen processing and rejection of the virus via induction of specific immunity. This is an example of a secondary "helper" or bystander effect in the induction of specific immunity which may inhibit the growth of virus in the new host to a pathogenic level.

D. Viruses As Tissue Transplants: Possible Role in Evolution of the Allograft Response and Imunity to Enveloped Viruses Organs can be freely transplanted between humans that are identical twins or within strains of laboratory rodents where genetic homogeneity essentially eliminates the problem of diversity at the major histocompatibility complex. However, where genetic differences exist due to diversity in HLA class I antigens at the A, B, and C locus, there is rapid rejection of transplanted tissues by the new host due to a strong, potent and long-lasting allograft response. Since organ transplantation does not naturally occur in nature, it is tempting to hypothesize that the origin of this allograft response arose as an evolutionary mechanism to protect against allogeneic invasion by external agents. In other words, the MHC is a code that determines what is self and what is non-self; non-self should be attacked and destroyed. One kind of natural, non-self, MHC-bearing agent would be enveloped viruses.

Genetic stability of indigenous native peoples in primitive tribes is considerably greater than that seen in urban populations. Thus, limited HLA diversity of native peoples would be expected. Where viral infection occurs between individuals within the tribe, survivors will gain the ability to respond against the tribes limited repertoire of MHC antigens, in addition to the viral antigens. Eventually, this kind of limited exposure would permit development of alloreactive T cell responses against all the MHC allotypes present in that tribe. These strong alloreactive T cell responses against a limited number of alloantigens would be as effective, or perhaps even more effective, than immunity directed against the specific viral epitopes. At a minimum, this kind of response benefits from its universality, i.e., it is not virus specific. Moreover, in those situations where there was by chance an MHC class I match between the infecting envelope virus and the new host, the peptide sequence presented in the MHC groove of the envelope virus would be more rapidly recognized by the cytotoxic T cells of the new host and thus trigger a rapid T cell response.

As modern, urban populations were formed by migration of individuals from many different tribes, the diversity of MHC antigens in a given population increased dramatically. It was impossible for isolated tribes to develop allotypic immunity against such large numbers of different HLA types given the lack of exposure. When brought into contact with larger civilizations, the chances of an infecting virus or virus-infected cell carrying either (i) the same allotype as the small tribe recipient or (ii) an allotype to which the small tribe recipient had previously been exposed, was greatly reduced. Consequently, it is not surprising how devastating were the viral epidemics that occurred when European sailors came in contact with isolated native peoples of island communities.

Thus, from an evolutionary standpoint, the strong allograft immune response, which certainly did not evolve to protect humans against tissue transplantation, is more likely to have evolved as a protection against infection from transfer of cellular antigens picked up from the host cell by enveloped viruses. This may be thought of as nature's version of graft-versus-host rejection. As further support for this hypothesis, it is not unusual to find naturally occurring anti-HLA antibodies to various loci in human males and females who have never undergone transplant, blood transfusion or become pregnant. It is possible that these antibodies were induced by infection with enveloped viruses having foreign HLA antigens.

Although the emphasis in this discussion has been on MHC class I genes coded by the A, B, C loci, there are also less well characterized D, E, and F alleles and class II MHC antigens consisting of HLA DR, DP, and DQ which might serve as targets for an alloimmune response. In addition, due to genetic diversity in populations, other membrane antigens that are under genetic control such as blood group antigens of the ABO and RH types could also conceivably serve as targets for an alloimmunization against envelope viruses.

E. Rationale

Because enveloped viruses acquire host cell membranes as they are synthesized, virus particles are expected to contain host cell MHC components as well as other cell surface antigens coded by diverse genes such as ABO blood groups. Intact infected cells will carry MHC components and other polymorphic antigens as well. MHC components in viral particles and infected cells provide a class of antigens in addition to viral antigens that could be the target of a protective immune response. Again, however, an unprimed immune response against foreign MHC likely would not be able to prevent infection. Thus, it would be necessary to prime the host immune system to respond against foreign MHC components and other alloantigens.

The present invention operates on the premise that, in fact, an effective vaccine can be designed around the use of MHC antigens and, perhaps, other allotypic antigens, more particularly, cells expressing MHC antigens. By priming an individual to response to foreign MHC antigens, it is believed that each enveloped virus particle or virus infected cell will be subject to a rapid and substantial immune response with activation of both the antibody mediated B cell and T cell arms of the immune response, and thereby prevent infection of host cells.

In its most basic form, the present invention is a vaccine comprising a plurality of MHC allotypes. If the vaccine comprises a single allotype, that vaccine will not stimulate any immune response in those individuals having the same allotype. This is unlikely except between identical twins because of the great genetic diversity present at the HLA A, B, and C allotypes, as well as, class II allotypes of modern civilization. Thus, a vaccine representing at least one or more allotypes will be of some benefit to every individual. The MHC antigens that make up various allotypes are expressed on the surface of intact cells or are part of membrane preparations derived from cells expressing MHC antigens. In addition, in some embodiments the vaccine also will contain viral encoded antigens and/or adjuvants. The following discussion will further describe the attributes of such vaccines and their use.

F. MHC Antigen Profiles

In order for an effective MHC-based vaccine to protect an individual against all infecting virus particles, that vaccine must provide the full spectrum of MHC antigens. For humans, this would mean that a single vaccine would have to include sufficient allotypes of MHC antigens to guarantee that at least one of the allotypes present on the virus envelope would be perceived as foreign by the vaccine recipient. FIG. 1 provides a list of HLA allotypes and their frequency of distribution by ethnic groups. Statistical analysis will yield appropriate combinations of antigens permitting maximal protection. This kind of vaccine would not be specific for a given virus.

In many cases, however, it is unnecessary for the vaccine to represent all possible MHC allotypes. Rather, substantial benefit will be achieved by use of a vaccine that contains antigens representing only the most common allotypes or allotypes that are regionally prevalent. For example, if an individual would be protected from virus arising from a majority of the population using only select allotypes, such a vaccine would have significant utility and might cost far less to produce than a vaccine with maximal efficacy, i.e., with antigens representative of every allotype. In fact, so long as more than one allotype is represented in the vaccine, the recipient of the vaccine will be immunized against at least one other allotype than his or her own. Again, such a vaccine would induce protection regardless of the nature of the infecting virus. Thus, the present invention comprises vaccines having two, three, four, five, six, seven, eight, nine, ten or more MHC allotypes.

The allotypic antigens used according to the present invention can be any of the major or minor histocompatability antigens or blood group antigens. In one embodiment, these antigens are provided in a cell free form. Such antigens may be purified from appropriate cells sources or, preferably, are produced by recombinant means following cloning of the corresponding gene. Methods by which cloning of allotypic antigens may be accomplished are well known to those of skill in the art. See Finney, "Molecular Cloning of PCR Products" in CURRENT PROTOCOLS INMOLECULAR BIOLOGY, Ausubel et al. Eds., John Wiley & Sons, New York (1987), p. 15.7.1.

Once the entire coding sequence of an allotypic gene has been determined, the gene can be inserted into an appropriate expression system. The gene can be expressed in any number of different recombinant DNA expression systems to generate large amounts of the polypeptide product. Examples of expression systems known to the skilled practitioner in the art include bacteria such as *E. coli*, yeast such as *Pichia pastoris*, baculovirus, and mammalian expression systems such as in Cos or CHO cells. In a preferred embodiment, polypeptides are expressed in *E. coli* and in baculovirus expression systems. A complete gene can be expressed or, alternatively, fragments of the gene encoding portions of polypeptide can be produced.

The gene sequence encoding the antigen is analyzed to detect putative transmembrane sequences. Such sequences are typically very hydrophobic and are readily detected by the use of standard sequence analysis software, such as MacVector (IBI, New Haven, Conn.). The presence of transmembrane sequences is often deleterious when a recombinant protein is synthesized in many expression systems, especially *E. coli*, as it leads to the production of insoluble aggregates which are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Antibodies to these sequences will not, therefore, prove useful in vaccines. Deletion of transmembrane-encoding sequences from the genes used for expression can be achieved by standard techniques. See Ausubel et al., supra, Chapter 8. For example, fortuitously-placed restriction enzyme sites can be used to excise the desired gene fragment, or PCR-type amplification can be used to amplify only the desired part of the gene. If these transgenes are to be used as part of a whole cell vaccine, however, retention of the transmembrane sequences is desired.

The gene or gene fragment encoding an can be inserted into an expression vector by standard subcloning techniques.

For example, an *E. coli* expression vector is used which produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.).

Some of these systems produce recombinant polypeptides bearing only a small number of additional amino acids, which are unlikely to affect the antigenic ability of the recombinant polypeptide. For example, both the FLAG system and the 6xHis system add only short sequences, both of which are known to be poorly antigenic and which do not adversely affect folding of the polypeptide to its native conformation. Other fusion systems produce polypeptide where it is desirable to excise the fusion partner from the desired polypeptide. In a preferred embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

In a preferred embodiment, the expression system used is one driven by the baculovirus polyhedrin promoter. The gene encoding the polypeptide can be manipulated by standard techniques in order to facilitate cloning into the baculovirus vector. A preferred baculovirus vector is the pBlueBac vector (Invitrogen, Sorrento, CA). The vector carrying the gene for the polypeptide is transfected into *Spodoptera frugiperda* (Sf9) cells by standard protocols, and the cells are cultured and processed to produce the recombinant antigen.

As an alternative to recombinant polypeptides, synthetic peptides corresponding to the antigens can be prepared. Such peptides are at least six amino acid residues long, and may contain up to approximately 35 residues, which is the approximate upper length limit of automated peptide synthesis machines, such as those available from Applied Biosystems (Foster City, Calif.). Use of such small peptides for vaccination typically requires conjugation of the peptide to an immunogenic carrier protein such as hepatitis B surface antigen. Methods for performing this conjugation are well known in the art.

G. Supplementing an MHC Vaccine With Viral Antigens and Adjuvants

One significant limitation exists, however, with respect to a vaccine based solely on MHC antigens. As stated above, a mammalian immune system is able to differentiate self from non-self cells and the mechanism by which self/non-self distinction is made involves MHC antigens. Thus, where an infecting virus or virus-infected cell happens to have arisen in an individual whose allotype is similar to the newly infected host, the MHC antigens on the infecting virus or virus-infected cell may not be seen as foreign and, hence, will not elicit an immune response regardless of whether or not the newly infected host was immunized with self-MHC antigens. Thus, an additional immune mechanism is required to provide immunity against virus and virus-infected cells arising from individuals of the same allotype.

One way in which this problem may be overcome is by adding antigens from the virus. Thus, where the infecting virus was generated in an individual with the same allotype as the individual being infected, an additional non-self recognition mechanism will be provided. Unlike an MHC-directed response, immunization with viral antigens would result in a immune response that was specific for a given virus.

Selection of viral antigens for use in supplementing the MHC-based vaccine of the present invention will be based on the following considerations. First, the selected antigens should be commonly and stably expressed in the envelope of the virus and the membrane of infected cells for induction of protective immunity. These antigens will be accessible to the antigen processing cells of the immune system of the individual being infected. Second, it is desirable that the selected antigens are the immunodominant species for the virus in question. Third, it is preferred that the selected antigens do not have any toxic or pathogenic function in and of themselves. Fourth, stable and immunodominant antigens presented by MHC class I complex following endogenous processing may be most effective in limiting spread of virus once infection of the new host has been successful. And fifth, it will be most expedient if the corresponding genes for the selected antigens have been cloned.

In other situations, it will be desireable to provide adjuvants that enhance the immune response to allotypes that are perceived as similar to, but distinct from, self. Such adjuvants include all acceptable immunostimulatory compounds such as cytokines, toxins or synthetic compositions. Examples of these are IL-1, IL-2, IL4, IL-7, IL-12, γ-interferon, GMCSP, BCG, aluminumhydroxide, N-acetyl-muramyl-L-threonyl-D-isoglutamine(thur-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2- (1'-2 '-dipalmityol-sn-glycero-3-hydroxyphosphoryloxy)-ethylamin (CGP) 1983A, referred to as MTP-PE), lipid A, MPL and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies or cytotoxic T cells with T cell receptors directed against an immunogenic polypeptide containing viral antigens resulting from administration of this polypeptide in vaccines which are also comprised of the various adjuvants. In some embodiments, it will prove beneficial to include both viral antigens and adjuvants, along with MHC antigens, in a single vaccine preparation. Where the adjuvants are polypeptides, it is possible to include the genes for these polypeptides in a suitable expression vector in a cellular version of the vaccine.

In addition to adjuvants, it may be desirable to coadminister biologic response modifiers (BRM), which have been shown to upregulate T cell immunity or downregulate suppressor cell activity. Such BRM's include, but are not limited to, Cimetidine (CIM; 1200 mg/d) (Smith/Kline, Pa.); or low-dose Cyclophosphamide (CYP; 300 mg/m$^2$) (Johnson/Mead, N.J.) and Cytokines such as γ-interferon, IL-2, or IL-12 or genes encoding proteins involved in immune helper functions such as B-7.

H. Cell Lines

As stated above, one problem with the use of subunit vaccines, comprised of either recombinant antigens or antigens isolated from a natural source, is that the antigens may have lost their "native" character. Usually, this change results from the loss of higher order structure. Because the factors affecting secondary and tertiary structure of proteins are manifold, it is difficult, if not sometimes impossible, to generate effective subunit vaccines. This may explain, in part, why live, attenuated vaccines have generally proved more effective at generating high level responses and long-lived immunity.

In order to address this problem, the present invention relies, in one embodiment, on intact cells to carry the MHC antigens. Conveniently, appropriate cell lines can be selected that represent major MHC allotypes. Various cell lines may be mixed together to achieve the necessary MHC profile. Regardless of the precise make-up, a significant advantage should accrue with the use of intact cells as the MHC antigens will be expressed and presented to the host in their native milieu. In fact, such cells should be analogous to live, attenuated vaccines.

It is conceivable that a single cell line can be genetically engineered to express multiple allotypes or, at least, multiple alleles of MHC antigens. It is a matter of routine skill for those in the field to clone genes corresponding to various allotypes of different MHC antigens, given the existing sequence homology of these molecules and knowledge of their tissue distribution. In this way, it is possible to increase the number of allotypes expressed in a given vaccine without increasing the number of cell types required. In fact, it may be possible to engineer a single cell that expresses a sufficient number of allotypes that significant protection is afforded thereby. This also is a way to generate a vaccine with higher levels of MHC expression or to provide an allotypic profile that is not available from a readily propagated cell line.

In certain embodiments, it will prove useful to treat the cells comprising the vaccine so that they do not replicate within the vaccinated host. This may be accomplished by a variety of means including irradiation, formaldehyde fixation, heating or freeze-thawing. Any other method in which the cells are rendered non-replicative, but left intact will, in theory, be useful. A preferred embodiment is irradiation since it has the ability to prevent replication of the living cells in the immunized person, yet the cells remain alive and capable of presenting alloantigenic, as well as, specific viral related peptide sequences as T cell epitopes appropriate for each of the MHC class I allotypes.

Where viral antigens are included in the vaccine, it is contemplated that a cell line is stably transformed with one or more viral antigens or the antigens may be isolated from various sources and simply mixed with the existing vaccine. In a preferred embodiment, an immunizing cell of the vaccine is stably transformed with an expression vector comprising a regulatory region that is functional in the cell operably linked to one or more viral antigen genes. These antigens are believed to be more stable than coat protein antigens and are less susceptible to antigenic drift. As stated above, this will permit protection of subjects where an infecting virus or virus-infected cell carries the same MHC allotype as the subject being infected. An additional benefit also may arise from the expression of viral antigens by cells. In certain cells, the viral antigen will be proteolytically "processed" and expressed in the context of the cells MHC molecules. This MHC "presentation" of antigen is an important part of antigen recognition and the use of living irradiated cells that temporarily survive in the individual being immunized and permit such presentation may result in improved priming of the immune response.

In another embodiment, it is contemplated that the cells will be transformed with genes encoding immunostimulatory compounds such as IL-1, IL-2, IL-4, IL-7, IL-12, γ-interferon or GMCSF. These products may act locally in enhancing the recognition of vaccine cells by the immune system. They also may provide a more systemic effect that enhances other aspects of the immune response.

DNA sequences useful for the transformation of cells can be recloned from standard plasmids into expression vectors with characteristics that permit higher levels of, or more efficient expression of the polypeptide encoded therein. At a minimum, this would require a eukaryotic promoter sequence which initiates transcription of the inserted DNA sequences. A preferred expression vector is one where the expression is inducible to high levels. This is accomplished by the addition of a regulatory region which provides increased transcription of downstream sequences under appropriate stimulation. Expression vectors may be integrative (retrovirus) or episomal (bovine papilloma virus).

Expression vectors are transferred into cells by any standard DNA transfer techniques. Calcium phosphate transformation, protoplast fusion, lipofection or electroporation are the preferred mechanisms for transfer of the vector into cells. In most situations, it will be desirable to include a selectable marker gene when transforming cells. When grown under selective conditions, surviving cells are much more likely to have taken up and expressed the gene of interest along with the selectable marker. All above methods are well known in the art.

The DNA's used to transform host cells preferably comprise a sequence that is optimized for expression of the encoded product in a given cell. Thus, in some instances, it will be desired that the nucleotide sequence to be expressed is a cDNA, while in other situations, it will be preferred to use genomic sequences. Degeneracy in codons for most amino acids means that nucleotide sequences other than the cDNA or genomic sequences for a given gene may encode the desired polypeptide.

It is possible that the use of MHC and viral antigens together will prove to be the best mechanism for induction of a protective immune response generally, and not merely a mechanism to ensure protection of subjects from virus or cells derived from individuals with similar allotypes. In such a case, it will be preferred that cell lines expressing one or more viral antigens be produced for each allotype desired in the vaccine. Alternatively, it may be possible to generate cells expressing multiple allotypes as well as viral antigens.

It also is contemplated that cell membrane preparations can be used as the vaccine substance. Because many MHC molecules are membrane bound, the use of membrane preparations could be used as an alternative source of MHC antigen that is delivered to the subject nor would be it be expected to substantially alter the higher order structure of such membrane bound molecules. Furthermore, since many of the MHC antigens have been cloned, the MHC molecules may also be produced by recombinant genetic engineering techniques.

In theory, any cell type may be used. Preferred characteristics for cells include ability to grow well in tissue culture, exhibit high amounts of MHC class I and II antigens, easily transducible with viral antigen genes and susceptible to irradiation which will make them incapable of prolonged growth in the new host. They must be free from extraneous adventitious viruses.

As a general proposition, cells are selected such that the representative HLA types of the target population will be present in the cells. Cells can be obtained by punch biopsies from patients in the target population and typed by standard protocols. Alternatively, malignant cells from patient biopsies within the target population may be employed for their superior growth in culture. Another possible source of normal or malignant cells is a cell depository such as the American Type Culture Collection (Rockville, Md.).

Selected cells lines are screened for adventitious infection by viral pathogens by standard assays (immunocytochemistry, electron microscopy, etc.). Cells are cultured using standard techniques adapted to the particular cell lines. When sufficient numbers of cells are available, the cells are irradiated with about 10,000 to 15,000 rads to inactivate the cells, preventing replication following administration. A suitable number of cells is between 8 and 10 million per administration.

FIGS. 1 through 3 provide lists of HLA allotypes and their frequency of distribution by ethnic group. It is a matter of routine experimentation to identify the needed allotypes and to select appropriate cells lines that provide the proper antigens. For most populations, it is estimated that no more than three or four cell lines will be required to provide a vaccine that encompasses 100% of the HLA antigen of the target population.

In a preferred embodiment, a vaccine according to the present invention comprises whole melanoma cells that have been irradiated. In a particularly preferred embodiment, the melanoma cells include three human melanoma cell lines (M-10VACC, M-24VACC, and M-101VACC), which were selected from a series of melanoma cell lines after careful examination for the high expression of certain MHC antigens, grown and prepared for administration as described in Hoon et al. (1990), incorporated herein by reference.

I. Methods for Administration

Administration of vaccine compositions according to the present invention will be via any common route including oral, nasal, buccal, rectal, vaginal, or topical. Alternatively, administration will be by intradermal subcutaneous, intramuscular, intraperitoneal, or intravenous injection. Vaccine compositions would normally be administered as pharmaceutically acceptable compositions that include physiologically acceptable carriers, buffers or other excipients.

The pharmaceutical compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations which are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

The term "unit dose" refers to physically discrete units suitable for use in humans, each unit containing a predetermined-quantity of the vaccine composition calculated to produce the desired immune response in association with its administration, i.e., the appropriate carrier, route and treatment regimen. The quantity to be administered, both according to number of treatments and unit dose, depends on the subject to be treated, capacity of the subject's immune system to respond and protection desired. Precise amounts of vaccine composition also depend on the judgment of the practitioner and are peculiar to each individual. Suitable dosage ranges are of the order of 0.001 to 10 mg of the active ingredient. Suitable regimes for initial administration and booster shots also vary, but are typified by immunization at day 0, 14, 28, and every 6 to 12 months thereafter.

J. A Prototype Vaccine

A model vaccine according to the present invention is melanoma cell vaccine, also referred to as "MCV." This vaccine consists of three melanoma cell lines that are known to contain effective concentrations of MHC antigens capable of inducing responses against a variety of HLA allotypes which are representative of a large proportion of human MHC class I genes. In addition, the MCV contains six melanoma associated antigens, also referred to here as "MAA." These MAA's, including three gangliosides (GD2, GM2 and O-acetyl GD3) and three protein antigens (a lipoprotein M-TAA, M-fetal antigen and M-urinary antigen) have been demonstrated to be immunogenic in melanoma patients. These antigens are located on the cell surface, and antibodies to them have been shown to bind with complement and kill melanoma cells in vitro. Morton et al., Prolongation of Survival in Metastatic Melanoma After Active Specific Immunotherapy With a New Polyvalent Melanoma Vaccine, *Annals of Surgery*, 216:463–482 (1992). Immunization of patients with MCV containing these antigens induces specific immune responses to the MAA.

A Phase II trial was undertaken to evaluate use of MCV in patients with advanced metastatic melanoma. Patients receiving this vaccine have survived significantly longer than patients previously treated with other regimens of immunotherapy or chemotherapy. The vaccine was administered to patients for melanoma metastatic to regional skin and subcutaneous sites (AJCC Stage IIIA) as well as to distant sites (AJCC Stage IV). Compared to previous trials, the new vaccine was significantly more effective at eliciting specific humoral and cell-mediated immune responses. Those patients who were treated with the new polyvalent MCV and developed high levels of humoral antibody and/or cell-mediated immune responses exhibited prolonged survival compared to non-responding patients.

J. EXAMPLES

Example 1

Melanoma Cell Vaccine

The active specific immunotherapy protocol involves immunization of subjects with irradiated whole cell MCV. MCV consists of three human melanoma cell lines (M-10VACC, M-24VACC, and M-101VACC), which were selected from a series of melanoma cell lines after careful examination for the high expression of melanoma associated antigens, grown and prepared for administration as described in Hoon et al. (1990), incorporated herein by reference.

The HLA types of the three cell lines in the MCV are given in Table V. It will be noted that the cross reacting alleles for the A locus are likely to be present in 120% of the caucasian population and for the B locus 70% of the population.

An outside laboratory screened the MCV for viral (HIV, hepatitis), bacterial and fungal infectious organisms. Equal amounts of each line were pooled to a total of $24\times10^6$ cells in serum-free medium containing 10% dimethyl sulfoxide and cryopreserved in liquid nitrogen. After cryopreservation, the cells were irradiated to 100 GY.

TABLE V

HLA Types of MCV

| CELL LINE | HLA TYPE | APPROX. FREQUENCY OF HLA TYPE IN CAUCASIAN POPULATION |
|---|---|---|
| M-10 | A 3 | 24.7% |
| | A 11 | 20.5% |
| | B 7 | 23.6% |
| | B 55 | 8.2% |
| M-24 | A 1 | 26.7% |
| | A 29 | 9.6% |
| | B 38 | 4.1% |
| | B 42 | |
| M101 | A 2 | 48.6% |
| | A 29 | 9.6% |
| | B 44 | 25.5% |

Prior to treatment, MCV was thawed and washed three times in media RPMI 1640. MCV was injected intradermally in axillary and inguinal regions on a schedule of every 2 wk for three times, then monthly for one year. For the first two treatments, MCV was mixed with tice strain BCG ($8\times10^6$ organisms). After one year, the immunization interval was increased to every 3 months for four times, then every 6 months. Follow-up clinical and laboratory evaluations were repeated monthly.

The antibody response to melanoma cell surface antigens following MCV immunization are evaluated by the indirect membrane immunofluorescence (IMIF) assay, as described in Morton et al., *Surgery* 64:233–240 (1968); Jones et al., *J. Nat'l Cancer Inst.* 66:249–254 (1981).

Delayed Cutaneous Hypersensitivity (DCH) are measured by intradermal skin tests with MCV before and during therapy. One-tenth of the pooled MCV ($2.4\times10^6$ cells) are administered at a remote site on the forearm. After 48 hours, the average diameter of the induration is recorded as the DCH response. The student t-test was used to compare the absolute values of DCH from wk 0 to 4 and to 16.

General immunocompetence is evaluated by sensitization and challenge to DNCB and response to common skin test antigens such as mumps and candida. The responses to purified protein derivative (PPD) antigen to which the patient becomes sensitized as result of immunization with BCG in the vaccine serves as additional controls. Mixed Lymphocyte Tumor Cell Reaction (MLTR) is used to evaluate the in vitro response to immunization. PBL's from weeks 0, 4 and 16 are isolated and cryopreserved. Assays are performed on cryopreserved lymphocytes to ensure reproducibility. Serial bleed PBL are simultaneously thawed, washed, and resuspended in culture medium (RPMI 1640 with 10% human AB serum (heat-inactivated) (Irvine Scientific, Calif.)).

MCV, when administered alone, is very well tolerated, with virtually no significant toxicity when administered up to 5 years at 3-month intervals. Mild erythema and itching are noted in the treatment sites by a majority of patients. This is transient, lasting only 2–3 days. About 15% of patients report low grade fever of <99° F. for 12 to 24 hr. A similar proportion of patients report mild fatigue on the day or two following treatment with MCV alone. Myalgia and arthralgia are rarely reported. When mixed with BCG, ulcerations at the injection sites are commonly seen.

Example 2

Induction of Antibodies Reactive with Influenza A and B

We have tested the coded sera from patients immunized with this MCV for antibodies reactive in a blinded ELISA assay with influenza A and influenza B using the preimmunization sera as a control. The data are summarized in Table I. We have found that 81 % of the patients after immunization with MCV showed increased serological reactivity by ELISA to influenza A of at least 0.5 antigen units and 38% had similar increased serologic activity to influenza B. This increased activity is believed secondary to cross-reacting cellular antigens in MCV.

TABLE I

Induction of Antibodies Reactive with Influenza A and B

| PATIENT | | ELISA UNITS | |
|---|---|---|---|
| INITIALS | BLEED DATE | INFLUENZA A | INFLUENZA B |
| D. D. | 10/15/92 | 1.78 | 4.86 |
| D. D. | 11/16/92 | 2.84 | 6.56 |
| D. D. | 12/21/92 | 3.67 | 6.89 |
| R. S. | 07/27/94 | 2.1 | 2.99 |
| R. S. | 08/25/94 | 3.0 | 2.72 |
| R. S. | 09/29/94 | 3.16 | 2.72 |
| R. K. | 03/23/88 | 5.39 | 5.89 |
| R. K. | 05/05/88 | 6.95 | 8.05 |
| R. K. | 08/25/88 | 5.74 | 6.73 |
| C. G. | 08/03/94 | 4.62 | 9.09 |
| C. G. | 09/15/94 | 8.10 | 5.50 |
| P. O. | 01/30/86 | 5.58 | 1.73 |
| P. O. | 02/27/86 | 5.80 | 1.73 |
| P. O. | 06/19/86 | 5.80 | 1.58 |
| C. C. | 05/22/89 | 3.1 | 1.32 |
| C. C. | 08/14/89 | 3.23 | 1.31 |
| C. C. | 04/24/89 | 3.65 | 1.51 |
| J. S. | 08/06/85 | 5.8 | 8.36 |
| J. S. | 10/29/85 | 6.37 | 8.39 |
| D. H. | 10/13/86 | 2.22 | 7.6 |
| D. H. | 11/14/86 | 2.32 | 9.04 |
| D. H. | 02/06/87 | 2.23 | 8.45 |
| J. H. | 07/08/92 | 8.80 | 6.82 |
| J. H. | 08/05/92 | 7.47 | 5.59 |
| J. H. | 10/29/92 | 8.59 | 6.95 |
| F. A. | 11/26/86 | 6.84 | 3.94 |
| F. A. | 01/12/87 | 7.39 | 3.43 |
| F. A. | 05/07/87 | 7.93 | 3.58 |
| M. H. | 09/24/85 | 6.84 | 13.9 |
| M. H. | 10/18/85 | 7.9 | 13.8 |
| M. H. | 02/25/86 | 7.6 | 13.6 |
| P. R. | 12/02/85 | 9.05 | 1.97 |
| P. R. | 01/06/86 | 9.96 | 2.69 |
| P. R. | 03/25/86 | 8.55 | 2.1 |
| P. R. | 05/12/86 | 9.75 | 2.12 |
| D. H. | 07/17/85 | 10.3 | 6.50 |
| D. H. | 08/13/85 | 12.0 | 7.12 |
| D. H. | 01/03/86 | 8.88 | 5.38 |
| S. V. H. | 09/09/85 | 3.02 | 1.74 |
| S. V. H. | 10/10/85 | 4.55 | 2.34 |
| S. V. H. | 02/10/86 | 3.74 | 1.90 |
| J. W. | 04/09/93 | 2.59 | 1.01 |
| J. W. | 05/18/93 | 3.25 | 1.04 |
| J. W. | 11/16/93 | 3.30 | 0.75 |
| I. B. | 12/03/91 | 6.10 | 7.18 |
| I. B. | 01/10/92 | 7.45 | 7.11 |
| I. B. | 04/22/92 | 6.01 | 6.63 |

Example 3

Induction of Cytotoxic Antibodies Reactive with Cell Surface Antigens on the Surface of Peripheral Blood Lymphocytes Taken from a Panel of 106 Normal Donors The sera from 10 of the 16 immunized patients formed sufficient titers of antibodies to induce cytotoxicity to allogenic lymphocytes from at least 20% of the test population of 116 normal lymphocyte donors (Table II) when tested by a standard Terasaki assay for cytotoxic antibodies. Six of the 16 individuals or 38% formed antibodies that were cytotoxic to >50% of the normal donor lymphocyte population. The frequency of cytotoxic antibodies varied from 20% to 97% against lymphocytes from individuals in the test panel.

Thus, in summary, it is clear that immunization with MCV was successful in inducing antibodies reactive with cellular antigens present on influenza A and B viruses by ELISA and capable of inducing lysis of allogenic lymphocytes in 63% of immunized subjects. These same antibodies which were capable of causing lysis of lymphocytes in the presence of complement would be capable of causing lysis of the viral membranes of enveloped viruses which contained the same MHC alloantigens.

TABLE II

Induction of Cytotoxic Antibodies Reactive with Peripheral Blood Lymphocytes taken from a Panel of 116 Normal Donors

| PATIENT INITIALS | SERUM CODE | BLEED DATE | CYTOTOXIC ANTIBODY TO PHERIPHERAL BLOOD LYMPHOCYTES* |
|---|---|---|---|
| D. D. | JWHLA-01 | 10/15/92 | 0 |
| D. D. | JWHLA-17 | 11/16/92 | 0 |
| D. D. | JWHLA-48 | 12/21/92 | 0 |
| R. S. | JWHLA-02 | 07/27/92 | 0 |
| R. S. | JWHLA-25 | 08/25/92 | 0 |
| R. S. | JWHLA-40 | 09/29/94 | 28% |
| R. K. | JWHLA-03 | 03/23/88 | 0 |
| R. K. | JWHLA-26 | 05/05/88 | 0 |
| R. K. | JWHLA-39 | 08/25/88 | 80% |
| C. G. | JWHLA-04 | 08/03/94 | 0 |
| C. G. | JWHLA-18 | 09/15/94 | 0 |
| P. O. | JWHLA-05 | 01/30/86 | 0 |
| P. O. | JWHLA-19 | 02/27/86 | 0 |
| P. O. | JWHLA-46 | 06/19/86 | 0 |
| C. C. | JWHLA-06 | 05/22/89 | 0 |
| C. C. | JWHLA-27 | 08/14/89 | 6% |
| C. C. | JWHLA-38 | 04/24/89 | 0 |
| J. S. | JWHLA-20 | 08/06/85 | 15% |
| J. S. | JWHLA-45 | 10/29/85 | 56% |
| D. H. | JWHLA-08 | 10/13/86 | 0 |
| D. H. | JWHLA-28 | 11/14/86 | 0 |
| D. H. | JWHLA-37 | 02/06/87 | 0 |
| J. H. | JWHLA-09 | 07/08/92 | 0 |
| J. H. | JWHLA-29 | 08/05/92 | 0 |
| J. H. | JWHLA-36 | 10/29/92 | 20% |
| F. A. | JWHLA-10 | 11/26/86 | 56% |
| F. A. | JWHLA-21 | 01/12/87 | 68% |
| F. A. | JWHLA-44 | 05/07/87 | 65% |
| M. H. | JWHLA-11 | 09/24/85 | 0 |
| M. H. | JWHLA-22 | 10/18/85 | 0 |
| M. H. | JWHLA-43 | 02/25/66 | 0 |
| P. R. | JWHLA-12 | 12/02/85 | 0 |
| P. R. | JWHLA-30 | 01/06/86 | 0 |
| P. R. | JWHLA-35 | 03/25/86 | 97% |
| P. R. | JWHLA-47 | 05/12/86 | 90% |
| D. H. | JWHLA-13 | 07/17/85 | 0 |
| D. H. | JWHLA-23 | 08/13/85 | 70% |
| D. H. | JWHLA-42 | 01/03/86 | 87% |
| S. V. H. | JWHLA-14 | 09/09/85 | 0 |
| S. V. H. | JWHLA-24 | 10/10/85 | 0 |
| S. V. H. | JWHLA-41 | 02/10/86 | 29% |
| J. W. | JWHLA-15 | 04/09/93 | 0 |
| J. W. | JWHLA-31 | 05/18/93 | 0 |
| J. W. | JWHLA-34 | 11/16/93 | 70% |

TABLE II-continued

Induction of Cytotoxic Antibodies Reactive with Peripheral Blood Lymphocytes taken from a Panel of 116 Normal Donors

| PATIENT INITIALS | SERUM CODE | BLEED DATE | CYTOTOXIC ANTIBODY TO PHERIPHERAL BLOOD LYMPHOCYTES* |
|---|---|---|---|
| I. B. | JWHLA-16 | 12/03/91 | 0 |
| I. B. | JWHLA-32 | 01/10/92 | 0 |
| I. B. | JWHLA-33 | 04/22/92 | 30% |

*= % of donors lymphocytes killed by test sera using standard Terasaki tissue typing assay.

Example 4

Prevention of Upper Respiratory Infections and Chest "Colds" in Patients Receiving the Melanoma Vaccine To determine whether these in vitro immunologic reactions had any in vivo significance in regard to preventing infectivity with envelope viruses, a questionnaire was prepared which was filled out by 53 melanoma patients who developed 1 or more episodes of upper respiratory or chest "colds" per year and who had been receiving immunotherapy with the melanoma cell vaccine for 9 months or more (a length of time which is necessary to adequately sensitize against MHC alloantigens) (Table III). We wanted to judge whether this immunization had affected the incidence of upper respiratory infections or chest colds during immunotherapy versus their usual incidence of infections before immunotherapy. It was found that these patients exhibited an average of 1.74 respiratory infections per year before immunotherapy, compared to 1.11 after immunotherapy. Twenty-eight (53%) of these individuals reported no change in their incidence of such illness, whereas 4/53 (8%) reported an increase in frequency of "colds." However, 21 of the 53 or approximately 40% of the individuals, particularly those who had 2 or more upper respiratory infections per year, reported a diminution in frequency and severity of such illnesses which are usually caused by enveloped viruses such as rhinoviruses, influenza, parainfluenza viruses. Some individuals, particularly those who had three or more viral infections per year prior to immunotherapy showed a dramatic reduction in the frequency of colds and bouts of flu. Of the 12 patients who reported experiencing such frequent colds, 10 (83%) reported a decrease in the incidence of colds, one person reported no change, and only one reported an increase in number of colds. For the group that experienced a decrease in colds and flu, the average number of colds before immu-

TABLE III

Subset of Subjects with Three or More Colds/Flu Per Year

| PATIENT INITIALS | BEFORE IMMUNOTHERAPY | AFTER IMMUNOTHERAPY | CHANGE |
|---|---|---|---|
| S. B. | 4 | 1 | −3 |
| B. C. | 3 | 0 | −3 |
| D. H. | 6 | 2 | −4 |
| J. H. | 4 | 0 | −4 |
| M. M. | 4 | 1 | −3 |
| M. M. | 3 | 1 | −2 |
| M. N. | 3 | 5 | 2 |
| R. P. | 3 | 3 | 0 |
| L. S. | 3 | 0 | −3 |
| M. W. | 3 | 1 | −2 |
| R. B. | 5 | 1 | −4 |
| D. R. | 5 | 3 | −2 |

notherapy was 4; the average number of episodes experienced after immunotherapy was 1. See Table IV.

TABLE IV

Summary of All Immunized Subjects

| PATIENT INITIALS | NUMBER OF COLDS/FLU PER YEAR BEFORE IMMUNOTHERAPY | AFTER IMMUNOTHERAPY | CHANGE |
|---|---|---|---|
| R. B. | 5 | 1 | −4 |
| R. B. | 2 | 0 | −2 |
| S. B. | 4 | 1 | −3 |
| J. B. | 1 | 1 | 0 |
| S. C. | 2 | 1 | −1 |
| B. C. | 3 | 0 | −3 |
| G. D. | 1 | 1 | 0 |
| D. H. | 6 | 2 | −4 |
| J. H. | 4 | 0 | −4 |
| R. H. | 1 | 1 | 0 |
| N. K. | 1 | 0 | −1 |
| L. L. | 1 | 1 | 0 |
| W. M. | 1 | 0 | −1 |
| M. M. | 4 | 1 | −3 |
| M. M. | 3 | 1 | −2 |
| J. M. | 1 | 0 | −1 |
| R. P. | 1 | 0 | −1 |
| M. R. | 1 | 1 | 0 |
| L. S. | 3 | 0 | −3 |
| A. W. | 2 | 1 | −1 |
| M. W. | 3 | 1 | −2 |
| M. N. | 3 | 5 | 2 |
| B. S. | 1 | 3 | 2 |
| B. T. | 1 | 1 | 0 |
| C. W. | 1 | 3 | 2 |
| D. A. | 1 | 1 | 0 |
| G. B. | 1 | 1 | 0 |
| C. B. | 1 | 1 | 0 |
| P. B. | 1 | 1 | 0 |
| J. C. | 1 | 1 | 0 |
| B. D. | 1 | 1 | 0 |
| O. D. | 1 | 1 | 0 |
| T. W. D. | 5 | 3 | −2 |
| T. H. D | 1 | 2 | 1 |
| C. D. | 1 | 0 | −1 |
| S. E. | 1 | 1 | 0 |
| E. F. | 1 | 1 | 0 |
| S. G. | 1 | 1 | 0 |
| W. G. | 1 | 1 | 0 |
| M. H. | 1 | 0 | −1 |
| C. H. | 2 | 2 | 0 |
| D. H. | 1 | 1 | 0 |
| P. H. | 2 | 2 | 0 |
| R. L. | 1 | 1 | 0 |
| M. M. | 1 | 1 | 0 |
| M. M. | 1 | 1 | 0 |
| R. P. | 3 | 3 | 0 |
| D. R. | 1 | 1 | 0 |
| D. S. | 1 | 1 | 0 |
| J. T. | 1 | 1 | 0 |
| C. T. | 1 | 1 | 0 |
| M. V. | 1 | 1 | 0 |
| K. W. | 1 | 1 | 0 |
| MEAN: | 1.74 | 1.11 | −0.63 |

*Mean = 0 −3.26134 Prob > [T] 0.0020
*P = .002 by T-test for noll hypothesis

REFERENCES

The following references, to the extent that they provide exemplary procedural or other details supplementary to those set forth herein, are specifically incorporated herein by reference.

Ausubel et al. CURRENT PROTOCOLS IN MOLECULAR BIOLOGY, Chapter 8. John Wiley & Sons (1990)

Cranage, M. et al. Symposium for Nonhuman Primate Models in AIDS (PUERTO RICO), Nov. 17–20, 1992, 10pabstract no. 113

Cranage, M. et al. Symposium for Nonhuman Primate Models in AIDS (UNITED STATES), Sept. 19–22, 1993, 11 pabstract no. 27

Finney. CURRENT PROTOCOLS IN MOLECULAR BIOLOGY, Chapter 15. John Wiley & Sons, New York (1987)

Hoon et al. *Cancer Research* 50:5358–5364 (1990)

Jones et al. *J. Nat'l Cancer Inst.* 66:249–254 (1981)

Kion, Tracy A. and Geoffrey W. Hoffmann. *Science*, 253:1138–1140 (1991)

Kiprov, D. D., et al. *Science*, 263:737–738 (1994)

Langlois, Alphonse J., et al. *Science*, 255:292–293 (1992)

Levine, T. P. and B. M. Chain. *Critical Reviews in Biochemistry and Molecular Biology* 26:439–473 (1991)

Morton et al. *Surgery*, 64:233–240 (1968)

Morton et al. *Annals of Surgery*, 216:463–482 (1992)

Stott, E. J. *Nature*, 353:393 (1991)

Townsend and Bodmer. *Ann. Rev. Immnunol.* 7:601–624 (1989)

What is claimed is:

1. A method for generating an anti-major histocompatibility complex (MHC) immune response in a given mammal comprising:

(a) providing a composition comprising (i) intact cells, wherein said cells express MHC molecules representing at least four different MHC profiles from the species of said given mammal; and (ii) a pharmaceutically acceptable carrier, diluent or excipient, (b) administering said composition to said given mammal.

2. The method of claim 1, wherein at least one of said intact cells further expresses an antigen from an enveloped virus.

3. The method of claim 2, wherein each of said cells further expresses an antigen from an enveloped virus.

4. The method of claim 3, wherein said virus is a herpesvirus.

5. The method of claim 2, wherein said virus is a retrovirus.

6. The method of claim 2, wherein said virus is a togavirus.

7. The method of claim 2, wherein said virus is a rhabdovirus.

8. The method of claim 2, wherein said virus is a flavivirus.

9. The method of claim 2, wherein said virus is a coronavirus.

10. The method of claim 2, wherein said virus is a filovirus.

11. The method of claim 2, wherein said virus is a paramyxovirus.

12. The method of claim 2, wherein said virus is a orthomyxovirus.

13. The method of claim 2, wherein said virus is a bunyavirus.

14. The method of claim 2, wherein said virus is a arenavirus.

15. The method of claim 2, wherein said virus is a poxvirus.

16. The method of claim 2, wherein said virus is a iridovirus.

17. The method of claim 1, wherein step (a) is followed, and step (b) is preceded, by lethal irradiation of said cells.

18. The method of claim 1, wherein said profiles represent 80% or more of MHC alleles found in individuals of said mammalian species.

19. The method of claim 1, wherein any given cell expresses only a single MHC profile.

20. The method of claim 1, wherein at least one cell expresses at least two MHC profiles.

21. The method of claim 1, wherein said MHC molecules are Class I antigens.

22. The method of claim 1, wherein said MHC molecules are Class II antigens.

23. The method of claim 1, wherein said MHC molecules are both Class I and Class II antigens.

24. The method of claim 1, wherein said different MHC profiles are representative of all known MHC alleles of said mammalian species.

25. The method of claim 1, wherein said mammal is a human.

26. The method of claim 25, wherein said MHC profiles include at least one of the following human allotypes:

HLA$A_1$, $A_2$, $A_3$, $A_{11}$, $A_{24}$, $A_{29}$, $A_{32}$, $B_7$, $B_8$, $B_{13}$, $B_{35}$, $B_{38}$, $B_{44}$, $B_{55}$, $B_{60}$, $B_{62}$, $CW_1$, $CW_2$, $CW_4$, $CW_5$, $CW_6$, $CW_7$, $CW_9$, $CW_{10}$, $CW_{11}$, $DR_1$, $DR_3$, DR4, $DR_7$, $DR_8$, $DR_{11}$, $DR_{12}$, $DR_{13}$, $DR_{15}$,

ABO Blood Groups.

27. The method of claim 1, wherein said intact cells further express a cytokine.

28. The method of claim 27, wherein said cytokine is selected from the group consisting of IL-1, IL-2, IL4, IL-7, IL-12, γ-interferon and GMCSF.

29. The method of claim 1, wherein said intact cells farther express a costimulatory molecule.

30. The method of claim 29, wherein said costimulatory molecule is B-7.

* * * * *

UNITED STATES PATENT AND TRADEMARK OFFICE

CERTIFICATE OF CORRECTION

PATENT NO. : 6,168,787

DATED : January 2, 2001

INVENTOR(S) : Morton

It is certified that error appears in the above-identified patent and that said Letters Patent is hereby corrected as shown below:

In the title, item [54], please insert --A-- before 'PLURIPOTENT' therefor.

In the specification, column 1, before the background of the invention, please insert -- The government may own rights in the present invention pursuant to grant number CA 12582 from The National Institutes of Health.--

In claim 4, column 24, line 35, please delete "claim 3," and insert -- claim 2, -- therefor.

In claim 28, column 26, line 9, please delete "IL4" and insert -- IL-4 -- therefor.

In claim 29, column 26, line 12, please delete "farther" and insert --further -- therefor.

Signed and Sealed this

Eighth Day of May, 2001

*Attest:*

NICHOLAS P. GODICI

*Attesting Officer*

*Acting Director of the United States Patent and Trademark Office*